US010799505B2

(12) United States Patent
Arrigo et al.

(10) Patent No.: US 10,799,505 B2
(45) Date of Patent: Oct. 13, 2020

(54) CRYSTALLINE FORM OF (S)-N-(5-((R)-2-(2,5-DIFLUOROPHENYL)-PYRROLIDIN-1-YL)-PYRAZOLO[1,5-A] PYRIMIDIN-3-YL)-3-HYDROXY-PYRROLIDINE-1-CARBOXAMIDE HYDROGEN SULFATE

(71) Applicant: Array BioPharma, Inc., Boulder, CO (US)

(72) Inventors: Alisha B. Arrigo, Boulder, CO (US); Derrick Juengst, Boulder, CO (US); Khalid Shah, South San Francisco, CA (US)

(73) Assignee: Array BioPharma, Inc., Boulder, CO (US)

( * ) Notice: Subject to any disclaimer, the term of this patent is extended or adjusted under 35 U.S.C. 154(b) by 273 days.

(21) Appl. No.: 14/943,014

(22) Filed: Nov. 16, 2015

(65) Prior Publication Data

US 2016/0137654 A1 May 19, 2016

Related U.S. Application Data

(60) Provisional application No. 62/080,374, filed on Nov. 16, 2014, provisional application No. 62/169,545, filed on Jun. 1, 2015.

(51) Int. Cl.
*C07D 487/04* (2006.01)
*A61K 31/519* (2006.01)
*C12Q 1/48* (2006.01)

(52) U.S. Cl.
CPC .......... *A61K 31/519* (2013.01); *C07D 487/04* (2013.01); *C12Q 1/485* (2013.01); *C12Y 207/10001* (2013.01); *G01N 2333/91205* (2013.01); *G01N 2800/52* (2013.01); *Y02A 50/414* (2018.01)

(58) Field of Classification Search
CPC .............................. A61K 31/519; C07D 487/04
USPC ........................................ 514/259.3; 544/281
See application file for complete search history.

(56) References Cited

U.S. PATENT DOCUMENTS

| | | |
|---|---|---|
| 5,374,659 A | 12/1994 | Gowan |
| 5,430,021 A | 7/1995 | Rudnic et al. |
| 5,760,068 A | 6/1998 | Talley et al. |
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,534,085 B1 | 3/2003 | Zeligs |
| 7,384,632 B2 | 6/2008 | Devaux et al. |
| 7,491,794 B2 | 2/2009 | Blatt et al. |
| 7,550,470 B2 | 6/2009 | Fraley |
| 7,612,067 B2 | 11/2009 | Barbosa et al. |
| 7,615,383 B2 | 11/2009 | Devaux et al. |
| 8,106,167 B2 | 1/2012 | Wild, Jr. et al. |
| 8,114,989 B2 | 2/2012 | Wang et al. |
| 8,119,592 B2 | 2/2012 | Beigelman et al. |
| 8,148,107 B2 | 4/2012 | MacDonald et al. |
| 8,299,021 B2 | 10/2012 | Blatt et al. |
| 8,299,057 B2 | 10/2012 | Lombardi Borgia et al. |
| 8,338,417 B2 | 12/2012 | Li et al. |
| 8,450,322 B2 | 5/2013 | Andrews et al. |
| 8,513,263 B2 | 8/2013 | Haas et al. |
| 8,568,998 B2 | 10/2013 | Mani |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,691,221 B2 | 4/2014 | Pavone et al. |
| 8,791,123 B2 | 7/2014 | Allen et al. |
| 8,865,698 B2 | 10/2014 | Haas et al. |
| 8,911,734 B2 | 12/2014 | Latham et al. |
| 8,912,194 B2 | 12/2014 | Ciomei |
| 8,933,084 B2 | 1/2015 | Andrews |
| 8,946,226 B2 | 2/2015 | Ciomei et al. |
| 9,102,671 B2 | 8/2015 | Molteni et al. |
| 9,127,013 B2 | 9/2015 | Haas et al. |
| 9,187,489 B2 | 11/2015 | Takeda et al. |
| 9,242,977 B2 | 1/2016 | Takeuchi et al. |
| 9,346,788 B2 | 5/2016 | Wu et al. |
| 9,469,876 B2 | 10/2016 | Kuslich |
| 9,493,476 B2 | 11/2016 | Andrews et al. |

(Continued)

FOREIGN PATENT DOCUMENTS

| | | |
|---|---|---|
| AU | 2015/101722 | 5/2016 |
| CN | 1938311 | 3/2007 |

(Continued)

OTHER PUBLICATIONS

JoVE Science Education Database. Organic Chemistry. Purifying Compounds by Recrystallization. JoVE, Cambridge, MA, (2019).*

(Continued)

*Primary Examiner* — Jeffrey H Murray
(74) *Attorney, Agent, or Firm* — Meunier Carlin & Curfman LLC

(57) ABSTRACT

A novel crystalline form of (S)-N-(5-((R)-2-(2,5-difluorophenyl)pyrrolidin-1-yl)-pyrazolo[1,5-a]pyrimidin-3-yl)-3-hydroxypyrrolidine-1-carboxamide, pharmaceutical compositions containing said crystalline form and the use of said crystalline form in the treatment of pain, cancer, inflammation, neurodegenerative disease or *Trypanosoma cruzi* infection are disclosed. In some embodiments, the novel crystalline form comprises a stable polymorph of (S)-N-(5-((R)-2-(2,5-difluorophenyl)pyrrolidin-1-yl)-pyrazolo[1,5-a] pyrimidin-3-yl)-3-hydroxypyrrolidine-1-carboxamide hydrogen sulfate. The present invention is further directed to a process for the preparation of the novel crystalline form.

15 Claims, 30 Drawing Sheets

Specification includes a Sequence Listing.

(56) References Cited

U.S. PATENT DOCUMENTS

| | | |
|---|---|---|
| 9,670,207 B2 | 6/2017 | Sasmal et al. |
| 9,682,979 B2 | 6/2017 | Allen et al. |
| 9,701,681 B2 | 6/2017 | Kim et al. |
| 9,782,400 B2 | 10/2017 | Yao et al. |
| 9,782,414 B2 * | 10/2017 | Arrigo ............... C07D 487/04 |
| 9,782,415 B2 | 10/2017 | Allen et al. |
| 9,796,724 B2 | 10/2017 | Allen et al. |
| 9,902,741 B2 | 2/2018 | Andrews et al. |
| 10,137,127 B2 | 11/2018 | Reynolds et al. |
| 10,172,861 B2 * | 1/2019 | Arrigo ............... C07D 487/04 |
| 10,285,993 B2 * | 5/2019 | Arrigo ............... C07D 487/04 |
| 2003/0118654 A1 | 6/2003 | Santos |
| 2006/0089362 A1 | 4/2006 | Seno et al. |
| 2006/0094699 A1 | 5/2006 | Kampen et al. |
| 2006/0128725 A1 | 6/2006 | Guzi |
| 2006/0211696 A1 | 9/2006 | Hibi et al. |
| 2007/0025540 A1 | 2/2007 | Travis |
| 2007/0042941 A1 | 2/2007 | Hirashima et al. |
| 2007/0082900 A1 | 4/2007 | Guzi et al. |
| 2007/0082902 A1 | 4/2007 | Paruch et al. |
| 2007/0184117 A1 | 8/2007 | Gregory et al. |
| 2007/0225270 A1 | 9/2007 | Guzi et al. |
| 2007/0281951 A1 | 12/2007 | Guzi et al. |
| 2009/0041717 A1 | 2/2009 | Macdonald et al. |
| 2010/0029633 A1 | 2/2010 | Allen et al. |
| 2010/0152219 A1 | 6/2010 | Block et al. |
| 2010/0297115 A1 | 11/2010 | Blaustein |
| 2011/0166122 A1 | 7/2011 | Andrews et al. |
| 2011/0195948 A1 | 8/2011 | Haas et al. |
| 2011/0268725 A1 | 11/2011 | Shelton |
| 2012/0108568 A1 | 5/2012 | Allen et al. |
| 2013/0029925 A1 | 1/2013 | Vandier et al. |
| 2013/0203776 A1 | 8/2013 | Andrews et al. |
| 2013/0217662 A1 | 8/2013 | Andrews et al. |
| 2014/0194403 A1 | 7/2014 | Haas et al. |
| 2014/0227287 A1 | 8/2014 | Kamohara et al. |
| 2014/0243332 A1 | 8/2014 | Davare |
| 2014/0315199 A1 | 10/2014 | Rhodes et al. |
| 2014/0336236 A1 | 11/2014 | Cronin et al. |
| 2015/0005499 A1 | 1/2015 | Haas et al. |
| 2015/0051222 A1 | 2/2015 | Barbugian et al. |
| 2015/0166564 A1 | 6/2015 | Allen et al. |
| 2015/0218652 A1 | 8/2015 | Doebele et al. |
| 2015/0283132 A1 | 10/2015 | Lim et al. |
| 2015/0306086 A1 | 10/2015 | Wilcoxen |
| 2016/0000783 A1 | 1/2016 | Takeuchi et al. |
| 2016/0010068 A1 | 1/2016 | Bastian |
| 2016/0032396 A1 | 2/2016 | Diehn |
| 2016/0032402 A1 | 2/2016 | Jagani et al. |
| 2016/0032404 A1 | 2/2016 | Schweighofer et al. |
| 2016/0108123 A1 | 4/2016 | Freeman et al. |
| 2016/0108380 A1 | 4/2016 | Iavarone et al. |
| 2016/0145237 A1 | 5/2016 | Hu et al. |
| 2016/0228441 A1 | 8/2016 | Haas et al. |
| 2016/0251357 A1 | 9/2016 | Andrews et al. |
| 2016/0263086 A1 | 9/2016 | Toretsky |
| 2016/0272725 A1 | 9/2016 | Stransky et al. |
| 2016/0305943 A1 | 10/2016 | Takeuchi et al. |
| 2016/0367547 A1 | 12/2016 | Yao et al. |
| 2017/0107232 A1 | 4/2017 | Andrews et al. |
| 2017/0112842 A1 | 4/2017 | Andrews et al. |
| 2017/0112849 A1 | 4/2017 | Andrews et al. |
| 2017/0114059 A1 | 4/2017 | Andrews et al. |
| 2017/0114067 A1 | 4/2017 | Haas et al. |
| 2017/0114068 A1 | 4/2017 | Andrews et al. |
| 2017/0114069 A1 | 4/2017 | Allen et al. |
| 2017/0114415 A1 | 4/2017 | Doebele et al. |
| 2017/0119770 A1 | 5/2017 | Allen et al. |
| 2017/0165267 A1 | 6/2017 | Arrigo et al. |
| 2017/0224662 A1 | 8/2017 | Motheram et al. |
| 2017/0260589 A1 | 9/2017 | Nanda et al. |
| 2017/0281632 A1 | 10/2017 | Cox et al. |
| 2017/0296544 A1 | 10/2017 | Reynolds et al. |
| 2018/0021342 A1 | 1/2018 | Arrigo et al. |
| 2018/0030548 A1 | 2/2018 | Nanda et al. |
| 2018/0030549 A1 | 2/2018 | Nanda et al. |
| 2018/0119228 A1 | 5/2018 | Nanda et al. |
| 2018/0127427 A1 | 5/2018 | Haas et al. |
| 2018/0133222 A1 | 5/2018 | Cox et al. |
| 2018/0140604 A1 | 5/2018 | Tuch et al. |
| 2018/0142306 A1 | 5/2018 | Nanda et al. |
| 2018/0207162 A1 | 7/2018 | Arrigo et al. |
| 2018/0263984 A1 | 9/2018 | Allen et al. |
| 2019/0031684 A1 | 1/2019 | Andrews |
| 2019/0076436 A1 | 3/2019 | Andrews |
| 2019/0076437 A1 | 3/2019 | Andrews |
| 2019/0151322 A1 | 5/2019 | Andrews |
| 2019/0169193 A1 | 6/2019 | Andrews et al. |
| 2019/0211017 A1 | 7/2019 | Haas et al. |
| 2019/0216814 A1 | 7/2019 | Reynolds et al. |
| 2019/0218222 A1 | 7/2019 | Reynolds et al. |
| 2019/0247398 A1 | 8/2019 | Zhao et al. |
| 2019/0365763 A1 | 12/2019 | Allen et al. |
| 2020/0000807 A1 | 1/2020 | Arrigo et al. |

FOREIGN PATENT DOCUMENTS

| | | |
|---|---|---|
| CN | 101119996 | 2/2008 |
| CN | 101208093 | 6/2008 |
| EA | 009517 | 2/2008 |
| EP | 0810217 | 12/1997 |
| EP | 1873157 | 1/2008 |
| EP | 1948633 | 8/2011 |
| EP | 2986736 | 2/2016 |
| EP | 2558490 | 12/2016 |
| EP | 3266795 | 10/2018 |
| JP | H10120683 | 5/1998 |
| JP | 2004-087707 | 3/2004 |
| JP | 2004-277337 | 10/2004 |
| JP | 2005-008581 | 1/2005 |
| JP | 2006-518364 | 8/2006 |
| JP | 2007-504276 | 3/2007 |
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| JP | 2014-082984 | 5/2014 |
| WO | WO 1998/49167 | 11/1998 |
| WO | WO 00/59929 | 10/2000 |
| WO | WO 2003/080064 | 10/2003 |
| WO | WO 2004/022561 | 3/2004 |
| WO | WO 2004/052286 | 6/2004 |
| WO | WO 2004/052315 | 6/2004 |
| WO | WO 2004/074290 | 9/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |
| WO | WO 2005/049033 | 6/2005 |
| WO | WO 2005/077954 | 8/2005 |
| WO | WO 2006/052913 | 5/2006 |
| WO | WO 2006/061417 | 6/2006 |
| WO | WO 2006/087538 | 8/2006 |
| WO | WO 2006/115452 | 11/2006 |
| WO | WO 2006/123113 | 11/2006 |
| WO | WO 2006/131051 | 12/2006 |
| WO | WO 2006/131952 | 12/2006 |
| WO | WO 2007/013673 | 2/2007 |
| WO | WO 2007/015824 | 2/2007 |
| WO | WO 2007/022999 | 3/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |

(56) References Cited

FOREIGN PATENT DOCUMENTS

| WO | WO 2007/062805 | 6/2007 | | |
|---|---|---|---|---|
| WO | WO 2007/084815 | 7/2007 | | |
| WO | WO 2007/102679 | 9/2007 | | |
| WO | WO 2007/103308 | 9/2007 | | |
| WO | WO 2007/113000 | 10/2007 | | |
| WO | WO 2007/129161 | 11/2007 | | |
| WO | WO 2008/016131 | 2/2008 | | |
| WO | WO 2008/021924 | 2/2008 | | |
| WO | WO 2008/030579 | 3/2008 | | |
| WO | WO 2008/037477 | 4/2008 | | |
| WO | WO 2008/052734 | 5/2008 | | |
| WO | WO 2008/058126 | 5/2008 | | |
| WO | WO 2008/115974 | 9/2008 | | |
| WO | WO 2008/116898 | 10/2008 | | |
| WO | WO 2008/155421 | 12/2008 | | |
| WO | WO 2009/013126 | 1/2009 | | |
| WO | WO 2009/052145 | 4/2009 | | |
| WO | WO 2009/053442 | 4/2009 | | |
| WO | WO 2009/060197 | 5/2009 | | |
| WO | WO 2009/070567 | 6/2009 | | |
| WO | WO 2009/092049 | 7/2009 | | |
| WO | WO 2009/140128 | 11/2009 | | |
| WO | WO 2010/012733 | 2/2010 | | |
| WO | WO 2010/033941 | 4/2010 | | |
| WO | WO 2010/048314 | 4/2010 | | |
| WO | WO2010048314 | * 4/2010 | ............ | C07D 471/04 |
| WO | WO 2010/051549 | 5/2010 | | |
| WO | WO 2010/058006 | 5/2010 | | |
| WO | WO 2010/093928 | 8/2010 | | |
| WO | WO 2011/006074 | 1/2011 | | |
| WO | WO 2011/130340 | 10/2011 | | |
| WO | WO 2011/133637 | 10/2011 | | |
| WO | WO 2011/146336 | 11/2011 | | |
| WO | WO 2012/024650 | 2/2012 | | |
| WO | WO 2012/034091 | 3/2012 | | |
| WO | WO 2012/034095 | 3/2012 | | |
| WO | WO 2012/116217 | 8/2012 | | |
| WO | WO 2012/158413 | 11/2012 | | |
| WO | WO 2013/059740 | 4/2013 | | |
| WO | WO 2013/074518 | 5/2013 | | |
| WO | WO 2013/174876 | 11/2013 | | |
| WO | WO 2013/183578 | 12/2013 | | |
| WO | WO 2014/016433 | 1/2014 | | |
| WO | WO 2014/036387 | 3/2014 | | |
| WO | WO 2014/047572 | 3/2014 | | |
| WO | WO 2014/078322 | 5/2014 | | |
| WO | WO 2014/078323 | 5/2014 | | |
| WO | WO 2014/078325 | 5/2014 | | |
| WO | WO 2014/078328 | 5/2014 | | |
| WO | WO 2014/078331 | 5/2014 | | |
| WO | WO 2014/078372 | 5/2014 | | |
| WO | WO 2014/078408 | 5/2014 | | |
| WO | WO 2014/078417 | 5/2014 | | |
| WO | WO 2014/078454 | 5/2014 | | |
| WO | WO 2014/083567 | 6/2014 | | |
| WO | WO 2014/130975 | 8/2014 | | |
| WO | WO 2014/134096 | 9/2014 | | |
| WO | WO 2014/152777 | 9/2014 | | |
| WO | WO 2015/017533 | 2/2015 | | |
| WO | WO 2015/064621 | 5/2015 | | |
| WO | WO 2015/112806 | 7/2015 | | |
| WO | WO 2015/124697 | 8/2015 | | |
| WO | WO 2015/175788 | 11/2015 | | |
| WO | WO 2015/183837 | 12/2015 | | |
| WO | WO 2016/027754 | 2/2016 | | |
| WO | WO 2016/097869 | 6/2016 | | |
| WO | WO 2016/187508 | 11/2016 | | |
| WO | WO 2016/196141 | 12/2016 | | |
| WO | WO 2016/196671 | 12/2016 | | |
| WO | WO 2017/001491 | 1/2017 | | |
| WO | WO 2017/004342 | 1/2017 | | |
| WO | WO 2017/075107 | 5/2017 | | |
| WO | WO 2017/155018 | 9/2017 | | |
| WO | WO 2017/184597 | 10/2017 | | |
| WO | WO 2017/201156 | 11/2017 | | |
| WO | WO 2017/201241 | 11/2017 | | |
| WO | WO 2018/081417 | 5/2018 | | |
| WO | WO 2018/170381 | 9/2018 | | |
| WO | WO 2019/005796 | 1/2019 | | |
| WO | WO 2019/084285 | 5/2019 | | |

OTHER PUBLICATIONS

Adriaenssens et al., "Nerve Growth Factor Is a Potential Therapeutic Target in Breast Cancer," Cancer Res., 2008, 68(2):346-351.
American Cancer Society," Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.
Asaumi et al., "Expression of neurotrophins and their receptors (TRK) during fracture healing," Bone, 2000, 26(6):625-633.
Bardelli, "Mutational analysis of the tyrosine kinome in colorectal cancers," Science, 2003, 300:949.
Brodeur, "Neuroblastoma: biological insights into a clinical enigma," Nat. Rev. Cancer, 2003, 3:203-216.
Brzezianska et al., "Rearrangements of NTRK1 oncogene in papillary thyroid carcinoma," Neuroendocrinology Letters, 2007, 28(3):221-229.
Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.
Campos et al., "Enantioselective, palladium-catalyzed alpha-arylation of N-Boc-pyrrolidine," J. Am. Chem Soc., 2006, 128:3538-3539.
Caria et al., "Cytogenetic and molecular events in adenoma and well-differentiated thyroid follicular-cell neoplasia," Cancer Genet. Cytogenet., 2010, 203:21-29.
Chang-Qi et al., "Brain derived neurotrophic factor (BDNF) contributes to the pain hypersensitivity following surgical incision in the rats," Molecular Pain, 2008, 4:27.
Chinese Office Action in Chinese Patent Application No. CN 201180025013.9, dated Apr. 28, 2014, 11 pages.
Chinese Office Action in Chinese Patent Application No. CN201080040095.X, dated Feb. 27, 2015, 8 pages (English translation).
Cho et al., "Expression of mRNA for brain-derived neurotrophic factor in the dorsal root ganglion following peripheral inflammation," Brain Research, 1997, 749:358-362.
Colombian Office Action in Colombian Application No. CO 12-022-116-4, dated Feb. 14, 2014, 8 pages.
Colombian Office Action in Colombian Application No. CO 12-229421-4, dated Jan. 21, 2014, 6 pages.
Dang et al., "Expression of nerve growth factor receptors is correlated with progression and prognosis of human pancreatic cancer," J. Gastroenterology and Hepatology, 2006, 21(5): 850-858.
Davidson et al., "Expression and activation of the nerve growth factor receptor TrkA in serous ovarian carcinoma," Clin. Cancer Res., 2003, 9(6):2248-2259.
Davies et al., "Resistance to ROS1 inhibition mediated by EGFR pathway activation in non-small cell lung cell," PLoS One, 2013, 8(12):e82236, 13 pages.
Delafoy et al., "Role of nerve growth factor in the trinitrobenzene sulfonic acid-induced colonic hypersensitivity," Pain, 2003, 105:489-497.
Di Mola et al., "Nerve growth factor and Trk high affinity receptor (TrkA) gene expression in inflammatory bowel disease," Gut, 2000, 46(5):670-678.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "Phase II Trial of Stereotactic Body Radiation Therapy Combined with Erlotinib for Patients With Limited but Progressive Metastatic Non-Small-Cell Lung Cancer," J. Clin. Oncol., 2014, 32:9 pages.

(56) References Cited

OTHER PUBLICATIONS

Doebele et al., "An oncogenic NTRK fusion in a soft tissue sarcoma patient with response to the tropomysin-related kinase (TRK) inhibitor LOXO-101," Cancer Discovery, Jul. 2015, 5(10):1049-1057.

Dolle et al., "Nerve growth factor-induced migration of endothelial cells," J. Pharmacol Exp Ther, 2005, 315(3):1220-1227.

Dou et al., "Increased nerve growth factor and its receptors in atopic dermatitis: an immunohistochemical study," Archives of Dermatological Research, 2006, 298(1):31-37.

Du et al., "Expression of NGF family and their receptors in gastric carcinoma: a cDNA microarray study," World Journal of Gastroenterology, http://www.wjgnet.com/1007-9327/full/v9/i7/1431.htm, Jul. 2003, 9(7):1431-1434.

Duranti et al., "Homologation of Mexiletine alkyl chanin and stereoselective blockade of skeletal muscle sodium channels," Euro. J. Med. Chem., 2000, 35:147-156.

Eguchi et al., "Fusion of ETV6 to neurotrophin-3 receptor TRKC in acute myeloid leukemia with t(12;15)(p13;q25)," Blood, 1999, 93(4):1355-1363.

European Search Report in European Application No. 13197815.7, dated Apr. 1, 2014, 5 pages.

Euthus et al., "ETV6-NTRK3—Trk-ing the primary event in human secretory breast cancer," Cancer Cell, 2002, 2(5):347-348.

Frattini et al., "The integrated landscape of driver genomic alterations in glioblastoma," Nature Genet., 2013, 45:1141-1149.

Freund-Michel and Frossard, "The nerve growth factor and its receptors in airway inflammatory diseases," Pharmacology & Therapeutics, 2008, 117(1):52-76.

Frey et al., "7-Aminopyrazolo[1,5-a]pyrimidines as potent multitargeted receptor tyrosine kinase inhibitors," J. Med. Chem, Jul. 2008, 51(13):3777-3787.

Greco et al., "Rearrangements of NTRK1 gene in papillary thyroid carcinoma," Molecular and Cellular Endocrinology, 2010, 321(1):44-49.

Gruber-Olipitz et al., "Neurotrophin 3/TrkC-regulated proteins in the human medulloblastoma cell line DAOY," J. Proteome Research, 2008, 7(5):1932-1944.

Gwak et al., "Attenuation of mechanical hyperalgesia following spinal cord injury by administration of antibodies to nerve growth factor in the rat." Neurosci. Lett., 2003, 336:117-120.

Hansen et al., "Autophagic cell death induced by TrkA receptor activation in human glioblastoma cells," J. of Neurochemistry, 2007, 103:259-275.

Harwood et al., "Experimental organic chemistry—Principles and practice," Experimental Chemistry—Organic Chemistry and Reaction, Jan. 1, 1989, 127-132.

Herzberg et al., "NGF involvement in pain induced by chronic constriction injury of the rat sciatic nerve," Neuroreport, 1997, 8:1613-1618.

Hong et al., "Clinical Safety and activity inhibitor from a Phase 1 study of LOXO-101, a selective TRKA/B/C inhibitor, in solid-tumor patients with NTRK gene fusions," 2016 AACR Annual Meeting, Apr. 17, 2016, 32 pages.

Hu et al., "Decrease in bladder overactivity with REN1820 in rats with cyclophosphamide induced cystitis," J. Urology, 2005, 173(3):1016-1021.

Hu et al., "Identification of brain-derived neurotrophic factor as a novel angiogenic protein in multiple myeloma" Cancer Genetics and Cytogenetics, 2007, 178:1-10.

Igaz et al., "Biological and clinical significance of the JAK-STAT pathway; lessons from knockout mice," Inflamm. Res., 2001, 50:435-441.

Ihle et al., "The Roles of Jaks and Stats in Cytokine Signaling," Canc. J. Sci. Am., 1998, 4(1):84-91.

International Preliminary Report on Patentability in International Application No. PCT/US2009/057729, dated Mar. 22, 2011, 7 pages.

International Preliminary Report on Patentability in International Application No. PCT/US2009/061519, dated Apr. 26, 2011, 6 pages.

International Preliminary Report on Patentability in International Application No. PCT/US2010/041538, dated Jan. 10, 2012, 7 pages.

International Preliminary Report on Patentability in International Application No. PCT/US2011/036452, dated Nov. 29, 2012, 6 pages.

International Search Report and Written Opinion in International Application No. PCT/US2009/0161519, dated Feb. 2, 2010, 8 pages.

International Search Report and Written Opinion in International Application No. PCT/US2009/057729, dated Feb. 4, 2010, 10 pages.

International Search Report and Written Opinion in International Application No. PCT/US2010/041538, dated Oct. 1, 2010, 10 pages.

International Search Report and Written Opinion in International Application No. PCT/US2015/060953, dated Feb. 8, 2016, 12 pages.

International Search Report and Written Opinion in International Application No. PCT/US2011/036452, dated Aug. 18, 2011, 9 pages.

Jaggar et al., "Inflammation of the rat urinary bladder is associated with a referred thermal hyperalgesia which is nerve growth factor dependent," Br. J. Anaesth, 1999, 83:442-448.

Japanese Office Action in Japanese Application No. JP 2013-511239, dated Mar. 4, 2015, 2 pages (English translation).

Jin et al., "TrkC plays an essential role in breast tumor growth and metastasis," Carcinogenesis, 2010, 31(11):1939-1947.

Jones et al., "Recurrent somatic alterations of FGFR1 and NTRK2 in pilocytic astrocytoma," Nature Genetics, 2013, 45:927-932.

Keysar et al., "A patient tumor transplant model of Squamous cell cancer identifies PI3K inhibitors as candidate therapeutics in defined molecular bins," Molecular Oncology, 2013, 7(4):776-790.

Kim et al., "NTRK1 fusion in glioblastoma multiforme," PloS ONE, 2014, 9(3):e91940.

Klijn et al., "A comprehensive transcriptional portrait of human cancer cell lines," Nat Biotechnol., 2015, 33(3):306-312.

Kolokythas et al., "Nerve growth factor and tyrosine kinase A receptor in oral squamous cell carcinoma: is there an association with perineural invasion?" J. Oral Maxillofacial Surgery, 2010, 68(6):1290-1295.

Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.

Kruettgen et al., "The dark side of the NGF family: neurotrophins in neoplasias," Brain Pathology, 2006, 16:304-310.

Lamb et al., "Nerve growth factor and gastric hyperalgesia in the rat," Neurogastrenterol. Motil., 2003, 15:355-361.

Leukemia, Wikipedia The Free Encylopedia, Dec. 8, 2001, https://en.wikipedia.org/wiki/Leukemia, 15 pages.

Li et al., "Brain derived neurotrophic factor (BDNF) contributes to the pain hypersensitivity following surgical incision in the rats," Molecular Pain, 2008, 4(28):1-11.

Li et al., "Correlation of expressions of GFAP, NT-3, Trk and NCAM with neurotropic molecular mechanism and clinical factors in adenoid cystic carcinoma of salivary gland," Chinese Journal of Cancer Prevention and Treatment, 2009, 16(6): 428-430 (with English abstract).

Li et al., "Lumbar 5 ventral root transection-induced upregulation of nerve growth factor in sensory neurons and their target tissues: a mechanism in neuropathic pain," Mol. Cell. Neurosci., 2003, 23:232-250.

Linch et al., "Systemic treatment of soft-tissue sarcoma [mdash] gold standard and novel therapies," Nature Reviews Clinical Oncology, 2014, 11(4):187-202.

Lorigan et al., "Phase III trial of two investigational schedules of ifosfamide compared with standard-dose doxorubicin in advanced or metastatic soft tissue sarcoma: a European Organisation for Research and Treatment of Cancer Soft Tissue and Bone Sarcoma Group Study," J. Clin Oncol., 2007, 25(21):3144-3150.

(56) References Cited

OTHER PUBLICATIONS

Lovly et al., "Inflammatory myofibroblastic tumors harbor multiple potentially actionable kinase fusions," Cancer Discov., 2014, 4(8):889-895.
Ma and Woolf, "The progressive tactile hyperalgesia induced by peripheral inflammation is nerve growth factor dependent," Neuroreport, 1997, 8:807-810.
Marchetti et al., "Frequent mutations in the neurotrophic tyrosine receptor kinase gene family in large cell neuroendocrine carcinoma of the lung," Human Mutation, 2008, 29(5):609-616.
Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McMahon et al., "The biological effects of endogenous nerve growth factor on adult sensory neurons revealed by a trkA-IgG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Corp., 27 pages.
Melo-Jorge et al., The Chagas' disease parasite Trypanosoma cruzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, deltaTrkA," Leukemia, 2007, 21:2171-2180.
Nagasubruamanian et al., "Brief Report: Infantile Fibrsarcoma With NTRK3-ETV6 Fusion Successfully Treated With the Tropomyosin-Related Kinase Inhibitor LOXO-101," Pediatric Blood & Cancer, 2016, DOI 10.1002, 3 pages.
Nakagawara, "Trk receptor tyrosine kinases a bridge between cancer and neural development," Cancer Letters, 2001, 169(2):107-114.
National Cancer Institute at the National Institutes of Health, posted on or before Jan. 5, 2000, retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
NCT02122913, "Oral TRK Inhibitor LOXO-101 for Treatment of Advanced Adult Solid Tumors," ClinicalTrials.gov, First received Apr. 16, 2014, Last Updated Dec. 7, 2015, https://clinicaltrials.gov/ct2/show/NCT02122913.
NCT02050919, "Sorafenib Tosylate, Combination Chemotherapy, Radiation Therapy, and Surgery in Treating Patients With High-Risk Stage IIB-IV Soft Tissue Sarcoma," ClinicalTrials.gov, First received Jan. 29, 2014, Last Updated Dec. 16, 2015, https://www.clinicaltrials.gov/ct2/show/NCT02050919, 5 pages.
Ni et al., "siRNA interference with a proliferation-inducing ligand gene in the Sgr-7901 gastric carcinoma cell line," Asian Pacific Journal of Cancer Prevention, 2012, 13:1511-1514.
O'Shea, "Jaks, STATs, cytokine signal transduction, and immunoregulation: are we there yet?" Immunity, 1997, 7:1-11.
Papatsoris et al., "Manipulation of the nerve growth factor network in prostate cancer," Exper Opin Invest Drugs, 2007, 16(3):303-309.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Perez-Pinera et al., "The Trk tyrosine kinase inhibitor K252a regulates growth of lung adenocarcinomas, " Molecular and Cellular Biochemistry, 2007, 295(1&2):19-26.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
Philippines Office Action in Philippines Application No. PH 1/2012/500048, dated May 30, 2014, 2 pages.

Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.
Pulciani et al., "Oncogenes in solid human tumours," Nature, 1982, 300(5892):539-542.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.
Raychaudhuri et al., "K252a, a high-affinity nerve growth factor receptor blocker, improves psoriasis: an in vivo study using the severe combined immunodeficient mouse-human skin model," J. Investigative Dermatology, 2004, 122(3):812-819.
Reuther et al., "Identification and characterization of an activating TrkA deletion mutation in acute myeloid leukemia," Mol. Cell. Biol. 2000, 20:8655-8666.
Ricci et al., Neurotrophins and neurotrophin receptors in human lung cancer, Am. J. Respiratory Cell and Molecular Biology, YR, 25(4): 439-446.
Ro et al., "Effect of NGF and anti-NGF on neuropathic pain in rats following chronic constriction injury of the sciatic nerve," Pain, 1999, 79:265-274.
Ross et al., "New routes to targeted therapy of intrahepatic cholangiocarcinomas revealed by next-generation sequencing," Oncologist, 2014, 19:235-242.
Rutkowski et al., "Treatment of advanced dermatofibrosarcoma protuberans with imatinib mesylate with or without surgical resection.," J. Eur. Acad. Dermatol. Venereol., 2011, 25:264-270.
Santoro et al., "Doxorubicin versus CYVADIC versus doxorubicin plus ifosfamide in first-line treatment of advanced soft tissue sarcomas: a randomized study of the European Organization for Reasearh and Treatment of Cancer Soft Tissue and Bone Sarcoma Group," J. Clin Oncol., 1995, 13(7):1537-1545.
Shelton et al., "Nerve growth factor mediates hyperalgesia and cachexia in auto-immune arthritis," Pain, 2005, 116:8-16.
Silverman, The Organic Chemistry of Drug Design and Drug Action, Second Edition, 2007, 20-21.
Sleijfer et al., "Prognastic and predictive factors for outcome to firs-line ifosfamide-containing chemotherapy for adult patients with advanced soft tissue sarcomas:an exploratory, retrospective analysis on large series from the European Organization for Research and Treatment of Cancer-Soft Tissue and Bone Sarcoma Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.
Smith et al., "Annotation of human cancers with EGFR signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.
Stephens et al., "Trk receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.
Tacconelli et al., "TrkA alternative splicing: a regulated tumor-promoting switch in human neuroblastoma," Cancer Cell, 2004, 6:347-360.
TAFINLAR, Highlights of Prescribing Information, GlaxoSmithKline, Jan. 2014, 41 pages.
Taipale et al., "Chaperones as thermodynamic sensors of drug-target interactions reveal kinase inhibitor specifities in living cells," Nat Biotech, 2013, 31(7):630-637.
Taiwan Office Action in Taiwan Application No. 098135670, dated Jan. 20, 2014, 7 pages (with English Translation).
Taiwan Search Report in Taiwan Application No. 098132033, dated Dec. 13, 2013, 1 page (English translation only).

(56) References Cited

OTHER PUBLICATIONS

Theodosiou et al., "Hyperalgesia due to nerve damage: role of nerve growth factor," Pain, 1999, 81:245-255.
Thiele, "On Trk—the TrkB signal transduction pathway is an increasingly important target in cancer biology," Clinical Cancer Research, 2009, 105(19):5962-5967.
Thompson et al., "Brain-derived neurotrophic factor is an endogenous modulator of nociceptive responses in the spinal cord," Proc.Natl. Acad. Sci. USA, 1999, 96:7714-7718.
Truzzi et al., "Neurotrophins and their receptors stimulate melanoma cell proliferation and migration," J. Investigative Dermatology, 2008, 128(8):2031-2040.
Truzzi et al., "Neurotrophins in healthy and diseased skin ," Dermato-Endrocrinology, 2008, 3(1):32-36.
Vaishnavi et al., "TRKing Down an Old Oncogene in a New Era of Targeted Therapy," Cancer Discovery, Jan. 2015, 5(1):25-34.
Vaishnavi et al., Oncogenic and drug-sensitive NTRK1 rearrangements in lung cancer, Nature Med., 2013, 19:1469-1472.
Van Gurp et al., "Phase 1 dose-escalation study of CP-690 550 in stable renal allograft recipients: preliminary findings of safety, tolerability, effects on lymphocyte subsets and pharmacokinetics,"Am. J. Transpl., 2008, 8:1711-1718.
Van Noesel et al., "Pediatric neuroblastomas: genetic and epigenetic 'danse macabre'," Gene, 2004, 325:1-15.
Wadhwa et al., "Expression of the neurotrophin receptors Trk A and Trk B in adult human astrocytoma and glioblastoma," Journal of Biosciences, 2003, 28(2):181-188.
Walch et al., "Role of neurotrophins and neurotrophins receptors in the in vitro invasion and heparanase production of human prostate cancer cells," Clin. Exp. Metastasis, 1999, 17:307-314.
Wang et al., "Trk kinase inhibitors as new treatments for cancer and pain," Expert Opin. Ther Patents, Mar. 2009, 19(3):305-319.
Wiesner et al., "Kinase fusions are frequent in Spitz tumours and spitzoid melanomas," Nature Comm., 2014, 5:3116.
Winski et al., "LOXO-101, a pan-TRK inhibitor, for the treatment of TRK-driven cancers," 26th EORTC-NCI-AACR Symposium on Molecular Targets and Cancer Therapeutics, Barcelona, Spain, 2014, 175.
Woolf et al., "Letter to Neuroscience: Nerve Growth Factor Contributes to the Generation of Inflammatory Sensory Hypersensitivity," Neuroscience, 1994, 62:627-331.
Wu et al., "The genomic landscape of diffuse intrinsic pontine glioma and pediatric non-brainstem high-grade glioma," Nature Genetics, 2014, 444-450.
XALKORI, Highlights of Prescribing Information, Pfizer Labs, Initial approval 2011, revised Mar. 2016, 20 pages.
Yilmaz et al., "Theraputic targeting of Trk supresses tumor proliferation and enhances cisplatin activity in HNSCC," Cancer Biology and Therapy, 2010, 10(6):644-653.
Zahn et al., "Effect of blockade of nerve growth factor and tumor necrosis factor on pain behaviors after plantar incision," J. Pain, 2004, 5:157-163.
Zelboraf, Highlights of Prescribing Information, Genentech USA, Initial Approval 2011, revised Aug. 2015, 18 pages.
Zhang et al., "Expression of nerve growth factor receptors and their prognostic value in human pancreatic cancer," Oncology Reports, 2005, 14:161-171.
Zheng et al., "Anchored multiplex PCR for targeted next-generation sequencing," Nature Med., Dec. 2014, 20(12):1479-1486.
Agaram et al., "Recurrent NTRK1 gene fusions define a novel subset oflocally aggressive lipofibromatosis-like neural tumors," Am. J. Surg. Pathol, Oct. 2016, 40(10): 1407-1416.
Agaram, et al., "Abstract 33: NTRK1 Associated Gene Fusions in Pediatric Fibroblastic Myofibroglastic Neoplasms: A Molecular Study of 58 Cases," 105th Annual Meeting of the United States and Canadian Academy of Pathology, 2016, 12A.
Aisner et al., "ROSI and ALK fusions in colorectal cancer, with evidence of intra-tumoral heterogeneity for molecular drivers.", Mal. Cancer Res., 12(1): 111-8, 2014.

Albaugh et al., "Discovery of GNF-5837, a Selective TRK Inhibitor with Efficacy in Rodent Cancer Tumor Models," ACS Medicinal Chemistry Letters, 2012, 3(2):140-145.
Ali et al., "Comprehensive Genomic Profiling Identifies a Subset of Crizotinib-Responsive ALK-Rearranged Non-Small Cell Lung Cancer Not Detected by Fluorescence In Situ Hybridization.", Oncologist, 21(6): 762-70, 2016.
Alvarez-Breckenridge et al., "Clinical and radiographic response following targeting ofBCAN-NTRK1 fusion in glioneuronal tumor," NPJ Precision Oncology, Mar. 2017, 5 pages.
Amatu et al., "NTRK gene fusions as novel targets of cancer therapy across multiple tumour types", ESMD Open, 1-9, 2016.
American Association for Cancer Research, "TRK Inhibitor Shows Early Promise," Cancer Discovery, 6(1), Jan. 1, 2016, XP009194480.
Andreason et al., "ETV6 Gene Rearrangements Characterize a Morphologically Distinct Subset of Sinonasal Low-grade Non-intestinal-type Adenocarcinoma," Am. J. Surg. Pathol, Nov. 2017, 41(11):1552-1560.
Arce et al., "Secretory carcinoma of the breast containing the ETV6-NTRK3 fusion gene in a male: case report and review of the literature," World J. Surg. Oncol, Jun. 2005, 3:35.
Ardini et al., "The TPM3-NTRK1 rearrangement is a recurring event in colorectal carcinoma and is associated with tumor sensitivity to TRKA kinase inhibition," Mol. Oncol. 8(8): 1495-1507, 2014.
Awad et al., "Acquired resistance to crizotinib from a mutation in CD74-ROS1. ", N Engl. J Med, 368(25): 2395-401, 2013.
Bailey, Justin J., et al. "Tropomyosin receptor kinase inhibitors: an updated patent review for 2010-2016—Part II." Expert opinion on therapeutic patents 27.7 (2017): 831-849.
Bartenstein et al., "Lipofibromatosis-like neural tumor: Case report of a unique infantile presentation," JAAD Case Reports, 4(2):185-188, 2018.
Baughn et al., "Abstract 5115: Whole-Genome Mate Pair Sequencing Reflex Test to Characterize Chromosome Rearrangements in Hematologic Neoplasia," Blood, 2017, 130: 5115.
Bavle et al., "Abstract GENE-04: Pediatric Malignant Epithelioid Glioneuronal Tumor: Pathological, Clinical, and Molecular Characterization of a Rare and Deadly Malignancy," Neuro-Oncology, Jun. 2017, ivl8-ivl9.
Bender et al., Abstract HG-024: Multiple Novel Fusion Genes with the RTK-RAS-PBK Signalling Axis Highlight its Central Role in the Turmorigenesis of Pediatric Gioblastoma, Neuro-oncology, Jun. 2014, 145.
Bensinger et al., "Transplantation of allogeneic peripheral blood stem cells mobilized by recombinant human granulocyte colony stimulating factor," Stem Cells, Jan. 1996;14(1):90-105.
Bensinger et al., "Transplantation of allogeneic peripheral blood stem cells mobilized by recombinant human granulocyte colony-stimulating factor [see comments].," Blood, Mar. 15, 1995;85(6):1655-8.
Bertrand et al., "The crystal structures of TrkA and TrkB suggest key regions for achieving selective inhibition," Journal of molecular biology, Oct. 26, 2012;423(3):439-53.
Birch et al., "Chromosome 3 anomalies investigated by genome wide SNP analysis of benign, low malignant potential and low grade ovarian serous tumours.", PLoS One, 6(12): e28250, 2011.
Braga, Dario, et al. "Crystal polymorphism and multiple crystal forms." Struct Bond (2009) 132:25-50. Springer-Verlag Berlin Heidelberg.
Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.
Brastianos et al., "Abstract OS06.4: Identification of Novel NTRK Fusion in Glioneuronal Tumors and Radiographic Response Following Therapy with an NTRK Inhibitor," Neuro-Oncology, May 2017, iii1 1, 1 page, Meeting Info: 5th Quadrennial Meeting of the World Federation of Neuro-Oncology Societies, WFNOS. Zurich, Switzerland, 2017.
Brenca et al., "Transcriptome sequencing identifies ETV6-NTRK3 as a gene fusion involved in GIST," J. Pathol. 238(4):543-549, 2016.

(56) References Cited

OTHER PUBLICATIONS

Brinner et al., "A rapid and general method for asymmetric synthesis of 2-substituted pyrrolidines using ter-butanesulfinamide," Organic & Biomolecular Chemistry, Jan. 2005, 3(11): 2019.

Bruse et al., "Improvements to Bead Based Oligonucleotide Ligation SNP Genotyping Assays," Biotechniques, Nov. 2008, 45:559-571.

Butti et al., "A sequence analysis of the genomic regions involved in the rearrangements between TPM3 and NTRK1 genes producing TRK oncogenes in papillary thyroid carcinomas," Genomics. 28(1):15-24, 1995.

Caira, "Crystalline Polymorphism of Organic Compounds, Topics in Current Chemistry," Feb. 1999, 198: 163-208.

Cajaiba et al., "Expanding the spectrum of ALK-rearranged renal cell carcinomas in children: Identification of a novel HOOK1-ALK fusion transcript.", Genes Chromosomes Cancer, 55(10): 814-7, 2016.

Calabresi and Chabner, Goodman & Gilnnan's The Pharmacological Basis of Therapeutics, 10th ed., 2001, ne: 1388, para 2, lines 4-5.

Calero et al., "Sunitinib suppress neuroblastoma growth through degradation of MYCN and inhibition of angiogenesis," PLoS One, Apr. 23, 2014;9(4):e95628. doi: 10.1371/iournal.pone.0095628. eCollection 2014.

Camidge, D. Ross, William Pao, and Lecia V. Sequist. "Acquired resistance to TKIs in solid tumours: learning from lung cancer." Nature reviews Clinical oncology 11.8 (2014): 473.

Camoratto et al., "CEP-751 inhibits TRK receptor tyrosine kinase activity in vitro exhibits anti-tumor activity," Int. J Cancer, Aug. 1997, 72:673-679.

Capparelli et al., "Stromal neuregulin-1 modulates the response to MEK inhibitors in WT BRAF/WTNRAS (WT/WT) melanomas", Pigment Cell Melanoma Res. vol. 30, No. 5, pp. e61, 2017.

Carpinelli et al., "PHA-739358, a potent inhibitor of Aurora kinases with a selective target inhibition profile relevant to cancer," Mol Cancer Ther, Dec. 2007;6(12 Pt 1):3158-3168.

Catic et al., "A novel cytogenetic and molecular characterization of renal metanephric adenoma, identification of partner genes involved in translocation t(9;15)(p24;q24)," Cancer Genet. 214-215:9-15, doi: 10.1016/j.cancergen.2017.03.001, 2017.

Catic et al., "Abstract 1537: the frequency of a novel KANK1 and NTRK3translocation and BRAFV600E mutation in patients diagnosed with metanephric adenoma utilizing molecular mechanisms," 2017 Annual Meeting of the American Society of Clinical Oncology, 2017, 1 page.

Center for Drug Evaluation and Research. https://www.accessdata.fda.gov/drugsatfda_docs/nda/2018/210861Orig1s000_211710Origls000ChemR.pdf, 2017.

Chaudhuri et al., "Early Detection of Molecular Residual Disease in Localized Lung Cancer by Circulating Tumor DNA Profiling," Cancer Discov, Dec. 2017, 7(12):1394-1403.

Chen et al.," 40: The landscape of kinase fusions in 445 Chinese NSCLC patients," Annals of Oncology, Oct. 2017, 28(7): viil6, 1 page.

Cherry et al., "Recent kinase and kinase inhibitor X-ray structures: mechanisms of inhibition and selectivity insights," Curr Med Chem. Mar. 2004;ll(6):663-73.

Chiang et al., "NTRK Fusions Define a Novel Uterine Sarcoma Subtype with Features of Fibrosarcoma," Am. J. Surg. Pathol. doi: 10.1097IPAS.0000000000001055, 2018.

Chmielecki et al., "Abstract LB-178: Genomic profiling of 1239 diverse pediatric cancers identifies novel discoveries across tumors", Cancer Research, vol. 76, No. 14, Supp. Supplement. Abstract Number: LB-178. 107th Annual meeting of the American Association for Cancer Research, AACR. New Orleans, LA Apr. 16-20, 2016.

Chmielecki et al., "Genomic Profiling of a Large Set of Diverse Pediatric Cancers Identifies Known and Novel Mutations across Tumor Spectra.", Cancer Research, 77(2): 509-519, 2017.

Choi et al., "(R)-2-Phenylpyrrolidine Substituted Irnidazopy ridazines: A New Class of Potent and Selective Pan-TRK Inhibitors," ACS medicinal chemistry letters, Mar. 2015 I 9;6(5):562-7.

Church et al., "Abstract ST16: A Novel EML4-NTRK3 Translocation in Infantile Fibrosarcoma and Congenital Mesoblastic Nephroma Requires a New Approach to Conventional Diagnostic Algorithms," J Molecular Diag, 2015, 816.

Church et al., "Recurrent EML4-NTRK3 fusions in infantile fibrosarcoma and congenital mesoblastic nephroma suggest a revised testing strategy," Mod. Pathol. 31(3), 463-473, 2018.

Cocce et al., "Identification of ZCCHC8 as fusion partner of ROS1 in a case of congenital glioblastoma multiforme with a t(6;12)(q21;q24.3)", Genes Chromosomes Cancer, 55(9): 677-87, 2016.

Coebergh et al., "Abstract 490: Identification of oncogenic gene fusions in primary colon cancers," Cancer Research, Jul. 2017, DOI: 10.1158/1538-7445.AM2017-490, 2 pages.

Comina-Mendez and Turner, "Predicting Relapse with Circulating Tumor DNA Analysis in Lung Cancer," CancerDiscov, Dec. 2017, 7(12): 1368-1370.

Communication pursuant to Rule 114(2) EPC, issued by the European Patent Office in EP Application No. 15808300.6 dated May 24, 2019. 9 pages.

Cook et al., "Somatic chromosomal engineering identifies BCAN-NTRK1 as a potent glioma driver and therapeutic target," Nat. Comm. 8(15987). DOI 10.1038/ncomms15987, 2017.

Crescenzo et al., "Convergent mutations and kinase fusions lead to oncogenic STAT3 activation in anaplastic large cell lymphoma.", Cancer Cell., 27(4): 516-32, 2015.

Croucher et al., "TrkB inhibition by GNF-4256 slows growth and enhances chemotherapeutic efficacy in neuroblastoma xenografts," Cancer Chemother Pharmacol. Jan. 2015;75(1):131-41. doi: 10.1007/s00280-014-2627-1. Epub Nov. 14, 2014.

Cruz, "Lung cancer: epidemiology, etiology and prevention," Clinics in Chest Medicine, 2011, 32(4): 1-61.

Cui et al., "Abstract #MA 07.09: ALK/ROSl/Inhibitor TPX-0005 Effectively Overcomes Clinical Resistance Solvent Front Mutations," Abstracts, Nov. 2017, p. S1829.

Cui et al., "Use of capture-based next-generation sequencing to detect ALK fusion in plasma cell-free DNA of patients with non-small-cell lung cancer", Oncotarget, 2771-2780, 2016.

Dacie et al., "ALK FISH patterns and the detection of ALK fusions by next generation sequencing in lung adenocarcinoma", Oncotarget, vol. 7, No. 50, pp. 82943-82952, 2016.

Das et al., "Synergistic Effects of Crizotinib and Temozolomide in Experimental FIG-ROS1 Fusion-Positive Glioblastoma.", Cancer Growth Metastasis, 8:51-60, 2015.

Davare et al., "Foretinib is a potent inhibitor of oncogenic ROS1 fusion proteins.", Proc. Natl. Acad Sci. USA., 110(48): 19519-24, 2013.

Davare et al., "Structural insight into selectivity and resistance profiles of ROSl tyrosine kinase inhibitors.", Proc. Natl. Acad Sci. USA., 112(39): E5381-90, 2015.

Davies and Dobele, "Molecular pathways: ROS1 fusion proteins in cancer.", Clin. Cancer Res, 19(15): 4040-4045, 2013.

Davies et al., "Identifying and targeting ROS1 gene fusions in non-small cell lung cancer.", Clin Cancer Res 18: 4570-4579, 2012.

Davis et al., "Infantile NTRK-associated Mesenchymal Tumors," Pediatr. Dev. Pathol. 21(1):68-78, 2018.

De Smith et al., "Clonal and microclonal mutational heterogeneity in high hyperdiploid acute lymphoblastic leukemia", Oneatarget., 7(45) 72733-72745, 2016.

Deihimi et al., "BRCA2, EGFR, and NTRK mutations in mismatch repair-deficient colorectal cancers with MSH2 or MLH1 mutations," Oncotarget. Jun. 20;8(25):39945-39962, 2017.

Demaria et al., "Development of tumor-infiltrating lymphocytes in breast cancer after neoadjuvant paclitaxel chemotherapy," Clin Cancer Res, Oct. 2001;7(10):3025-30.

Doebele et al., "Abstract 8023: NTRK1 gene fusions as a novel oncogene target in lung cancer," 2013 Annual Meeting of the American Society of Clinical Oncology, Chicago, IL, 2013, 1 page.

Dolomanov et al., "OLEX2: a complete structure solution, refinement and analysis program," J Annl. Cryst. 2009, 42, 339-341.

(56) References Cited

OTHER PUBLICATIONS

Drilon et al., "A Novel Crizotinib-Resistant Solvent-Front Mutation Responsive to Cabozantinib Therapy in a Patient with ROS1-Rearranged Lung Cancer.", Clin. Cancer Res., 22(10): 2351-8, 2016.
Drilon et al., "A phase 1 study of oral LOXO 292 in adult patients with advanced solid tumors, including RET-fusion non-small cell lung cancer, medullary thyroid cancer and other tumors with increased RET activity," Annals of oncology Developmental Therapeutics, Sep. 2017, 28(5): 138.
Drilon et al., "Abstract CT007: Entrectinib, an oral pan-Trk, ROSI, and ALK inhibitor in TKI-naive patients with advanced solid tumors harboring gene rearrangements: Updated phase I results," Cancer research, 76(14), AACR 107th Annual Meeting, Apr. 2016, URL <http://cancerres.aacrjournals.org/content/76/14 Supplement/CT007.short>, 5 pages.
Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.
Durham et al. "Diverse and Targetable Kinase Alterations Drive Histiocytic Neoplasms," Blood. 126(23):481, 2015.
Ellison et al., "Abstract 013: Genetic alterations in uncommon low-grade neural tumors—BRAF, FGFR1, and MYB/MYBL1 mutations occur frequently and align with morphology," Neuropathology and Applied Neurobiology, 2016, 42(S1): 18.
Elvin et al., "319: Genomic profiling of uterine leiomyosarcomas reveal frequent alterations in Akt/mammalian target of rapamycin (mTOR) pathway genes and other actionable genomic abnormalities linked to targeted therapies," Poster Session—Molecular Targeted Agents I, Nov. 2014, 1 page.
Engman et al., "Syngeneic transplant in mantle cell lymphoma: a rare event and review of the literature," Clin Adv Hematol Oncol. May 2009;7(5):321-3.
Esmo, "TRK Cancer-Causing Mutation Discovered in 1982 Finally Target of Clinical Trials: Matching drugs to long-overlooked oncogene," European Society of Medical Oncology, Jan. 2015, 2 pages.
Essand et al., "Genetically engineered T cells for the treatment of cancer," J Intern Med. Feb. 2013;273(2):166-81. doi: 10.1111/joim.12020.
Estrada-Bernal et al., "Abstract#: C65: TRK kinase domain mutations that induce resistance to a pan-TRK inhibitor," Poster, Presented at Proceedings of the AACR-NCI-EORTC International Conference: Molecular Targets and Cancer Therapeutics, Boston MA, Nov. 5-9, 2015; Mol Cancer Ther, Dec. 2015, 14(12)(Suppl. 2): 1 page.
Estrada-Bernal et al., "Abstract#: LB-118: Identification of TRKA and TRKB kinase domain mutations that induce resistance to a pan-TRK inhibitor," Posterm Presented at Proceedings of the 107th Annual Meeting of the American Association for Cancer Research, New Orleans, LA, Apr. 16-20, 2016; Cancer Res, Jul. 2016, 76(14): 1 page.
Extended European Search Report in European Application No. 17163978.4, dated Jul. 17, 2017, 5 pages.
Extended European Search Report in European Application No. 17199899.0, dated Feb. 26, 2018, 7 pages.
Extended European Search Report in European Application No. 18151233.6, dated Jun. 26, 2018, 6 pages.
Extended European Search Report in European Application No. 18208279.2, dated Jun. 27, 2019, 10 pages.
Facchinetti et al., "Crizotinib-Resistant ROSI Mutations Reveal a Predictive Kinase Inhibitor Sensitivity Model for ROS1- and ALK-Rearranged Lung Cancers.", Clin. Cancer Res., 22(24): 5983-5991, 2016.
Farago et al., "Abstract MINB0.09: Clinical Response to Entrectinib in a Patient with NTRK1-Rearranged Non-small cell Lung Cancer," J Thoracic Oncol, Sep. 2015, 10(9-S2): S374-S375.
Farago et al., "Durable clinical response to entrectinib in NTRK1-rearranged non-small cell lung cancer," J. Thorac Oncol. 10(12):1670-1674, 2015.

Farhat et al., "Primary benign and malignant thyroid neoplasms with signet ring cells: cytologic, histologic, and molecular features," Am. J. Clin. Pathol., 148(3):251-258, 2017.
Fernandez-Cuesta et al., "Abstract 1531: Cross-entity mutation analysis of lung neuroendocrine tumors sheds light into their molecular origin and identifies new therapeutic targets," AACR Annual Meeting 2014, Apr. 2014, URL <http://cancerres.aacrjournals.org/content/7 4/19 Supplement/1531.short>, 5 pages.
Flannery et al., "Immunomodulation: NK cells activated by interferon-conjugated monoclonal antibody against human osteosarcoma,". Eur J Cancer Clin Oncol. Jun. 1984;20(6):791-8
Forghieri et al., Abstract P137: Chronic Eosinophilic Leukemia with ETV6-NTRK3 Fusion Transcript in an Elderly Patient Affected with Pancreatic Carcinoma, Haemologica, 2010, 95(s3): S125-S126.
Fu et al., "The Frequency and Clinical Implication of ROS1 and RET Rearrangements in Resected Stage IIIA-N2 Non-Small Cell Lung Cancer Patients.", PLoS One, 10(4):e0124354, 2015.
Fuse et al., "Mechanisms of Resistance to NTRK Inhibitors and Therapeutic Strategies in NTRK1-Rearranged Cancers," Mol. Cancer Ther., Oct. 2017; 16(10); 2130-43.
Gainor et al., "Patterns of Metastatic Spread and Mechanisms of Resistance to Crizotinib in ROS1-Positive Non-Small-Cell Lung Cancer", JCO Precis Oneal. 10.1200/PO. 1 7.00063, 2017.
Gang et al., "The landscape of fusion transcripts in spitzoid melanoma and biologically indeterminate spitzoid tumors by RNA sequencing.", Mod Pathol., 29(4): 359-69, 2016.
Gao et al., "Driver fusions and their implications in the development and treatment of human cancers," Cell Rep. 23(1):227-238.e3, 2018.
Gatalica et al., "Abstract A047: Molecular characterization of the malignancies with targetable NTRK gene fusions," American Association for Cancer Research, Jan. 2018, 2 pages.
Gaudet et al., "Allele-specific PCR in SNP genotyping," Methods Mol Biol. 2009;578:415-24. doi: 10.1007/978-1-60327-411-126.
Gavrin et al., "Synthesis of Pyrazolo[1,5-[alpha]]pyrimidoinone Regioisomers," J Org Chem, Feb. 2007, 72(3): 1043-1046.
GenBank Accession No. AAB33109.1, "trkB [Homo sapiens]," Jul. 27, 1995, 1 page.
GenBank Accession No. AAB33111.1"trkC [Homo sapiens]," Jul. 27, 1995, 1 page.
GenBank Accession No. NM_ 002529, "high affinity nerve growth factor receptor isoform 2 precursor [Homo sapiens]," May 11, 2014, 4 pages.
GenBank Accession No. NM_001007792 "Homo sapiens neurotrophic tyrosine kinase, receptor, type 1 (NTRK1), transcript variant 3, mRNA," May 10, 2014, 5 pages.
GenBank Accession No. NP 001007793, "high affinity nerve growth factor receptor isoform 3 [Homo sapiens]," May 10, 2014, 3 pages.
GenBank Accession No. NP_ 002520 "high affinity nerve growth factor receptor isoform 2 precursor [Homo sapiens]," May 11, 2014, 4 pages.
GenBank Accession No. S76473.1, "trkB [human, brain, mRNA, 3194 nt]," Jul. 27, 1995, 2 pages.
GenBank Accession No. S76475.1, "trkC [human, brain, mRNA, 2715 nt]," Jul. 27, 1995, 2 pages.
Giacomini et al., "Breakpoint Analysis of Transcriptional and Genomic Profiles Uncovers Novel Gene Fusions Spanning Multiple Human Cancer Types", PLoS Gene.t, 9(4): e1003464, 2013.
Greco et al., "Chromosome I rearrangements involving the genes TPR and NTRK1 produce structurally different thyroid-specific TRK oncogenes," Genes Chromosomes Cancer. 19(2):112-23, 1997.
Greco et al., "The DNA rearrangement that generates the TRK-T3 oncogene involves a novel gene on chromosome 3 whose product has a potential coiled-coil domain," Mol. Cell. Biol. 15(11):6118-6127, 1995.
Greco et al., "TRK-Tl is a novel oncogene formed by the fusion of TPR and TRK genes in human papillary thyroid carcinomas," Oncogene. 7(2):237-42, 1992.
Green & Wuts, eds, "Protective Groups in Organic Synthesis," John Wiley & Sons Inc, May 8, 1999.
Groisberg et al., "Clinical next-generation sequencing in sarcomas", Journal of Clinical Oncology, vol. 34, Supp. Supplement 15;

(56) References Cited

OTHER PUBLICATIONS

Abstract Number: 11046; 2016 Annual Meeting of the American Society of Clinical Oncology, ASCO 2016, Chicago, IL. Jun. 3-7, 2016.
Gu et al., "Lung adenocarcinoma harboring concomitant SPTBN1-ALK fusion, c-Met overexpression, and HER-2 amplification with inherent resistance to crizotinib, chemotherapy, and radiotherapy.", J Hematol Oneal, 9(1): 66, 2016.
Hainsworth et al., "Lung Adenocarcinoma with Anaplastic Lymphoma Kinase (ALK) Rearrangement Presenting as Carcinoma of Unknown Primary Site: Recognition and Treatment Implications.", Drugs Real World Outcomes, 3:115-120, 2016.
Hakimi et al., "Minimally invasive approaches to prostate cancer: a review of the current literature.", Urol. J., 4: 130-137, 2007.
Hallberg and Palmer, "The role of the ALK receptor in cancer biology.", Ann. Oncology, 27 (Suppl 3):iii4-iii5. doi: 10.1093/annonc/mdw301, 2016.
Hamdouchi et al "Imidazo[1,2-b]pyridazines, novel nucleus with potent and broad spectrum activity against human picornavimses: design, synthesis, and biological evaluation" J Med Chem., Sep. 25, 2003;46(20):4333-4341.
Harada et al., "Role and Relevance of TrkB Mutations and Expression in Non-Small Cell Lung Cancer," Clinical Cancer Research, Jan. 17, 2011, 17(9):2638-2645.
Hayashi et al., "Crizotinib treatment for refractory pediatric acute myeloid leukemia with RAN-binding protein 2-anaplastic lymphoma kinase fusion gene.", Blood Cancer J, 6(8): e456, 2016.
Hechtman et al., "Identification of targetable kinase alterations in patients with colorectal carcinoma that are preferentially associated with wild-type RAS/RAF," Mol. Cancer Res. 14(3):296-301, 2016.
Hechtman et al., Abstract 1837: Pan-TRK IHC Is an Efficient and Reliable Screening Assay for Targetable NTRK Fusions, Annual Meeting Abstracts, 2017, 457A.
Hilfiker, Rolf, Fritz Blatter, and Markus von Raumer. "Relevance of solid-state properties for pharmaceutical products." Polymorphism in the pharmaceutical industry (2006): 1-19.
Hinrichs et al., "Exploiting the curative potential of adoptive T-cell therapy for cancer," Immunol Rev. Jan. 2014;257(1):56-71. doi: 10.1111/imr.12132.
Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.
Holla et al., "ALK: a tyrosine kinase target for cancer therapy", Cold Spring Harb Mol Case Study, 3(1):a001ll5. doi: 10.1101/mcs.a001ll5, 20 pages, 2017.
Hornick et al., "Expression of ROSI predicts ROSI gene rearrangement in inflammatory myofibroblastic tumors.", Mod Pathol., 28(5): 732-9, 2015.
Hover et al., "Abstract TMOD-07: NTRK3 Gene Fusions Drive Tumorigenesis in Novel Models of Pediatric HighGrade Glioma," Neuro-Oncology, Jun. 2017, iv49.
Howell et al., "Dynamic allele-specific hybridization. A new method for scoring single nucleotide polymorphisms," Nat Biotechnol. Jan. 1999;17(1):87-8.
Huehls et al., "Bispecific T-cell engagers for cancer immunotherapy," Immunol Cell Biol. Mar. 2015;93(3):290-6. doi: 10.1038/icb.2014.93. Epub Nov. 4, 2014.
Hyrcza et al., "Abstract OFP-06-007: Comparison of ultrastructural features between pediatric Mammary Analogue Secretory Carcinoma (MASC) of the salivary glands and Pediatric Secretory Breast Carcinoma (SBC) reveals similar pathological features," Virchows Arch, Sep. 2016, 469(Sl): Sl7.
Ihuegbu et al., "Non-invasive detection of crizotinib resistance in ALK-rearranged lung adenocarcinoma directs treatment with next-generation ALK inhibitors", J Clin. Oncology, vol. 34, Supp. Supplement 15, Abstract No. e20643, 2016 Annual Meeting of the American Society of Clinical Oncology, Chicago, IL, 2016.
Ikeda et al., "Basic Science", Annals of Oncology. vol. 28 (suppl_10): xl x6.10.1093/annonc/mdx652, 2017.

Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.
Iniguez-Ariza et al., "Abstract 6087: NTRK.1-3-point mutations in poor prognosis thyroid cancers," J Clinical Oncology, May 2017, 35(15): 6087.
Isdori et al., "Advancement in high dose therapy and autologous stem cell rescue in lymphoma," World J Stem Cells, Aug. 2015, 7(7):1039-1046.
Iyama et al., "Identification of Three Novel Fusion Oncogenes, SQSTM1/NTRK3, AFAP1L2/RET, and PPFIBP2/RET, in Thyroid Cancers of Young Patients in Fukushima," Thyroid. 27(6):811-818, 2017.
Iyer et al., "AZ64 inhibits TrkB and enhances the efficacy of chemotherapy and local radiation in neuroblastoma xenografts," Cancer Chemother Pharmacol. Sep. 2012;70(3):477-86. doi: 10.1007/s00280-012-1879-x. Epub May 24, 2012.
Iyer, R., "Entrectinib is a potent inhibitor of Trk-driven neuroblastomas in a xenograft mouse model." Cancer letters 372.2 (2016): 179-186. (Year: 2016).
Jencks and Regenstein, "Ionization Constants of Acids and Bases," Handbook of Biochemistry and Molecular Biology, 3rd ed., G.D. Fassman, CRC Press, 1976, 1: 305-347.
Johnson et al., "Comprehensive Genomic Profiling of 282 Pediatric Low- and High-Grade Gliomas Reveals Genomic Drivers, Tumor Mutational Burden, and Hypermutation Signatures.", Oncologist. 22(12): 1478-1490, 2017.
Kao et al., "Recurrent BRAF Gene Fusions in a Subset of Pediatric Spindle Cell Sarcomas," Am. J. Surg. Pathol. 42(1):28-38, 2018.
Karachialiou et al., "Real-time liquid biopsies become a reality in cancer treatment", Ann. Transl. Med, 3(3):36, 2016.
Katayama et al., "Cabozantinib Overcomes Crizotinib Resistance in ROS1 Fusion-Positive Cancer", Clin. Cancer Res., 21 (I): 166-7 4, 2015.
Katayama et al., "Mechanisms of Acquired Crizotinib Resistance in ALK Rearranged Lung Cancers," Sci Transl Med, Feb. 2012, 4(120): 120ra17.
Katayama et al., "Therapeutic targeting of anaplastic lymphoma kinase in lung cancer: a paradigm for precision cancer medicine.", Clin Cancer Res, 21(10): 2227-35, 2015.
Kim et al., "Mammaglobin-A is a target for breast cancer vaccination", Oncolmmunology 5(2):.el069940, 2016.
Kim et al., "SEC31A-ALK Fusion Gene in Lung Adenocarcinoma", Cancer Res Treat, 48(1): 398-402,2016.
Koboldt et al., "The next-generation sequencing revolution and its impact on genomics," Cell, Sep. 26, 2013;155(1):27-38. doi: 10.1016/j.cell.2013.09.006.
Kohsaka et al., Pediatric soft tissue tumor of the upper arm with LMNA-NTRK1 fusion, Hum. Pathol. 72:167-173,2017.
Kralik et al., "Characterization of a newly identified ETV6-NTRK3 fusion transcript in acute myeloid leukemia," Diagn. Pathol. 6:19, 2011.
Kubler et al., "Self-adjuvanted mRNA vaccination in advanced prostate cancer patients: a first-in-man phase I/IIa study.", J. Immunother Cancer 3 :26, 2015.
Kusano et al., "Two Cases of Renal Cell Carcinoma Harboring a Novel STRN-ALK Fusion Gene.", Am J SurgPathol. 40(6): 761-9, 2016.
Lansky et al., "The measurement of performance in childhood cancer patients," Cancer, 1987, 60(7):1651-1651.
Lecht et al., "Angiostatic effects of K252a, a Trk inhibitor, in murine brain capillary endothelial cells," Mol Cell Biochem, Jun. 2010;339(1-2):201-13. doi: 10.1007/sll010-010-0386-9. Epub Feb. 11, 2010.
Lee et al., "Identification of ROS1 rearrangement in gastric adenocarcinoma.", Cancer, 119(9): 1627-1635, 2013.
Leeman-Neill et al., "ETV6-NTRK3 is a common chromosomal rearrangement in radiation-associated thyroid cancer," Cancer, 2014, 120(6):799-807.
Leyvraz et al., Abstract Number: 897. Meeting Info: 33. Deutscher Krebskongress, DKK. Berlin, Germany, 2018.

(56) References Cited

OTHER PUBLICATIONS

Lezcano et al., "Regular transfusion lowers plasma free hemoglobin in children with sickle-cell disease at risk for stroke," Am. J. Surg. Pathol. doi: 10.1097/P. AS.0000000000001070, 2018.

Li et al., "Combinational Analysis of FISH and Immunohistochemistry Reveals Rare Genomic Events in ALK Fusion Patterns in NSCLC that Responds to Crizotinib Treatment", J Thorac. Oneal., 12(1):94-101. doi: 10.1016/i .itho.2016.08.145, 2017.

Li et al., "In vivo sensitized and in vitro activated B cells mediate tumor regression in cancer adoptive immunotherapy," J Immunol, Sep. 1, 2009;183(5):3195-203. doi: 10.4049/jimmunol.0803773. Epub Aug. 10, 2009.

Li et al., "Trk inhibitor attenuates the BDNF/TrkB-induced protection of neuroblastoma cells from etoposide in vitro and in vivo," Cancer Biol. Ther., Feb. 2015, 16(3):477-483.

Lin et al., "HG-48. Integrated sequencing of pediatric pilocytic Astrocytoma with anaplasia reveals molecular features of both Lowand high-grade glial tumors", Neuro-Oneol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.

Lu et al., "Targeted next generation sequencing identifies somatic mutations and gene fusions in papillary thyroid carcinoma," Oncotarget. 8(28):45784-45792, 2017.

Ma et al., "Responses to crizotinib in patients with ALK-positive lung adenocarcinoma who tested immunohistochemistry (IHC)-positive and fluorescence in situ hybridization (FISH)-negative", Oncotarget, 7(39), 64410-64420, 2016.

Macleod, et al., "Abstract 0294: Gene Targets ofETV6-NTRK3 Fusion," Haematologica, 14th Congress of the European Hematology Association,2009, 94(s2): 116.

Majweskaetal., CancerResearch, vol. 76, No. 14, Supp. Supplement. Abstract No. 3190. 107th Annual meeting of the American Association for Cancer Research, AACR. New Orleans, LA Apr. 16-20, 2016.

Marras et al., "Genotyping SNPs with molecular beacons," Methods Mol Biol, 2003;212:111-28.

McCahon et al., "Non-Resectable Congenital Tumors with the ETV6-NTRK3 Gene Fusion Are Highly Responsive to Chemotherapy," Med. Pediatr. Oncol., May 2003, 40(5):288-292.

McCarthy et al., "Tropomyosin receptor kinase inhibitors: a patent update 2009-2013," Expert Opin TherPat. Jul. 2014;24(7):731-44. doi: 10.1517/13543776.2014.910195. Epub May 8, 2014.

Milione et al., "Identification and characterization of a novel SCYL3-NTRK1 rearrangement in a colorectal cancer patient," Oncotarget, 8(33):55353-55360, 2017.

Montagnoli et al., "Anti-proliferative effects of GW441756, a novel inhibitor of NGF receptor tyrosine kinase a (TRKA), in human sarcoma," Italian Journal of Anatomy and Embryology, Nov. 11, 2010, 115:117.

Mulligan, "RET revisited: expanding the oncogenic portfolio.", Nature Reviews Cancer, 14, 173-186,2014.

Murakami et al., "Integrated molecular profiling of juvenile myelomonocytic leukemia", Blood, blood-2017-07-798157; DOI: 10.1182/blood-2017-07-798157, 2018.

Nakano et al., "Novel Oncogenic KLC1-ROS1 Fusion in Pediatric Low Grade Glioma", Pediatr Blood Cancer. vol. 64, S54-S55 Suppe. 4. 013-1-7, 2017.

Narayanan et al., "Discovery and preclinical characterization of novel small molecule TRK and ROS1 tyrosine kinase inhibitors for the treatment of cancer and inflammation," PLoS One, Dec. 26, 2013;8(12):e83380. doi: 10.1371/iournal.pone.0083380. eCollection 2013.

NIH National Cancer Institute [online], "progression (pm-GREH-shun)," NCI Dictionary of Cancer Terms, retrieved on Sep. 17, 2018, URL: <https://www.cancer.gov/publications/dictionaries/cancer-terms/def/progression>, 1 page.

NIH National Cancer Institute [online], "recurrence (ree-KER-ents)," NCI Dictionary of Cancer Terms, retrieved on Sep. 21, 2018, URL: <https://www.cancer.gov/publications/dictionaries/cancer-terms/def/recurrence>, 1 page.

NIH National Cancer Institute [online], "relapse (REE-laps)," NCI Dictionary of Cancer Terms, retrieved on Sep. 17, 2018, URL: <https://www.cancer.gov/publications/dictionaries/cancer-terms/def/relapse>, 1 page.

NIH, "List of Cancer-causing Agents Grows," National Institute of Environmental Health Sciences, https://www.niehs.nih.gov/news/newsroom/releases/2005/january31/index.cfm, 4 pages.

Nikiforova et al., Abstract Number: 5. Meeting Info: 84th Annual Meeting of the American Thyroid Association. Coronado, CA, United States, 2014.

Nollau et al., "Methods for detection of point mutations: performance and quality assessment. IFCC Scientific Division, Committee on Molecular Biology Techniques," Clin Chem. Jul. 1997;43(7):1114-28.

Obianyo et al., "Novel small molecule activators of the Trk family of receptor tyrosine kinases. BiochimBiophys Acta, 1834:2214-2218," BiochimBiophys Acta, Oct. 2013, 1834(10):2213-2218.

Oken et al., "Toxicity and response criteria of the Eastern Cooperative Oncology Group," Am J Clin Oncol, 1982, 5:649-655.

Olivier, "The Invader assay for SNP genotyping," Mutat Res, Jun. 3, 2005;573(1-2): 103-10.

Otsubo et al., "Sporadic pediatric papillary thyroid carcinoma harboring the ETV6/NTRK3 fusion in oncogene in a 7-year-old Japanese girl: a case report and review of literature," J. Pediatr. Endocrinol. Metab. 28;31(4):461-467, 2018.

Ott et al., "An immunogenic personal neoantigen vaccine for patients with melanoma.", Nature 547: 217-221, 2017.

Ou et al., "Emergence of novel and dominant acquired EGFR solvent-front mutations at Gly796 (G796S/R) together with C797S/R and L792F/H mutations in one EGFR (L858R/T790M) NSCLC patient who progressed on osimertinib," Lung Cancer, 2017, 108: 228-231.

Ou et al., "Identification of a novel TMEM106B-ROS1 fusion variant in lung adenocarcinoma by comprehensive genomic profiling.", Lung Cancer, 88(3):352-4, 2015.

Ou et al., "Next-Generation Sequencing Reveals a Novel NSCLC ALK Fl 174V Mutation and Confirms ALK G1202R Mutation Confers High-Level Resistance to Alectinib (CH5424802/RO5424802) in ALK-Rearranged NSCLC Patients Who Progressed on Crizotinib," Journal of Thoracic Oncology, Apr. 2014, 9: 549-553.

Pan et al., Laboratory Investigation, vol. 96, Supp. SUPPL. 1, pp. 367A, Abstract Number: 1450, 105th Annual Meeting of the United States and Canadian Academy of Pathology, Seattle, WA, 2016.

Panagopoulos et al., "Recurrent fusion of the genes FNl and ALK in gastrointestinal leiomyomas", Modem Pathology 29: 1415-1423, 2016.

Pao, W., et al. "Acquired resistance of lung adenocarcinomas to gefitinib or erlotinib is associated with a second mutation in the EGFR kinase domain," PLoS Med, Feb. 2005, 2(3), e73.

Park et al., "NTRKl fusions for the therapeutic intervention of Korean patients with colon cancer," Oncotarget. 7(7):8399-412, 2016.

PCT International Preliminary Report on Patentability in International Application No. PCT/US2015/060953, dated May 16, 2017, 7 pages.

PCT International Preliminary Report on Patentability in International Application No. PCT/US2016/035327, dated Dec. 14, 2017, 9 pages.

PCT International Preliminary Report on Patentability in International Application No. PCT/US2016/058951, dated May 11, 2018, 11 pages.

PCT International Preliminary Report on Patentability in International Application No. PCT/US2017/033257, dated Nov. 20, 2018, 8 pages.

PCT International Preliminary Report on Patentability in International Application. No. PCT/US2017/058518, dated Apr. 30, 2019, 8 pages.

(56) References Cited

OTHER PUBLICATIONS

PCT International Preliminary Report on Patentability in International Application No. PCT/US2018/022833, dated Sep. 26, 2019, 8 pages.
PCT International Preliminary Report on Patentability in International Application No. PCT/US2018/039502, dated Jan. 9, 2020, 8 pages.
PCT International Search Report and Written Opinion in International Application No. PCT/US2016/058951, dated Feb. 7, 2017, 20 pages.
PCT International Search Report and Written Opinion in International Application No. PCT/US2017/058518, dated May 2, 2018, 17 pages.
PCT International Search Report and Written Opinion in International Application No. PCT/US2018/022833, dated Aug. 13, 2018.
PCT International Search Report and Written Opinion in International Application No. PCT/US2018/039502, dated Apr. 16, 2018, 16 pages.
PCT International Search Report and Written Opinion in International Application No. PCT/US2018/057542, dated Mar. 6, 2019, 19 pages.
PCT International Search Report and Written Opinion in International Application No. PCT/US2019/024961, dated Jul. 23, 2019, 13 pages.
Perales et al., "Fast Cars and No Brakes: Autologous Stem Cell Transplantation as a Platform for Novel Immunotherapies," Biol Blood Marrow Transplant, Jan. 2016;22(1):17-22. doi: 10.1016/j.bbmt.2015.10.014. Epub Oct. 17, 2015.
Peus et al., "Appraisal of the Karnofsky Performance Status and proposal of simple algorithmic system for its evaluation," BMC Med Inform and Decision Making, 2013, 13:72.
Picarsic et al., "Molecular characterization of sporadic pediatric thyroid carcinoma with the DNA/RNA ThyroSeq v2 next-generation sequencing assay," Pediatr. Dev. Pathol, Mar. 2016, 19(2):115-122.
Plosker, "Sipuleucel-T: in metastatic castration-resistant prostate cancer.", Drugs 71(1): 101-108, 2011.
Ponsaerts et al., "Cancer immunotherapy using RNA-loaded dendritic cells," Clin. Exp. Immunol., Dec. 2003, 134:378-384.
Prabhakaran et al., "Novel TLE4-NTRK2 fusion in a ganglioglioma identified by array-CGH and confirmed by NGS: Potential for a gene targeted therapy," Neuropathology, Mar. 2018, doi:10.1111/neup.12458.
PubChem, "Larotrectinib," https://pubchem.ncbi.nlm.nih.gov/compound/46188928, retrived on Apr. 29, 2019, 20 pages.
Qaddoumi et al., "Genetic alterations in uncommon low-grade neuroepithelial tumors: BRAF, FGFR1, and MYB mutations occur at high frequency and align with morphology, "Acta Neuropathol, Jun. 2016, 131(6):833-845.
Qiu et al., "Next generation sequencing (NGS) in wild type GISTs", J Clin. Oneal. 35: 15 _suppl, e22507-e22507,2017.
Rausch et al., "mRNA vaccine CV9103 and CV9104 for the treatment of prostate cancer.", Human Vaccinimmunother 10(11): 3146-52, 2014.
Reshmi et al., "Abstract 477: Genomic and Outcome Analyses of Philadelphia Chromosome like (Ph-like) NCI Standard Risk B-Acute Lymphoblastic Leukemia (SR B-ALL) Patients Treated on Children's Oncology Group (COG) AALL0331," Blood, 2017, 130(Sl): 477.
Reungwetwattana et al., "Targeted therapies in development for non-small cell lung cancer," J Carcinog, Dec. 2013, 12:22, doi: 10.4103/1477-3163.123972. eCollection 2013.
Ricarte-Filho et al., "Identification of kinase fusion oncogenes in post-Chernobyl radiation-induced thyroid cancers," J. Clin. Invest, Nov. 2013, 123(11): 4935-4944.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Rimkunas et al., "Analysis of receptor tyrosine kinase ROSI-positive tumors in non-small cell lung cancer: identification of a FIG-ROSI fusion.", Clin. Cancer Res., 18: 4449-58, 2012.
Ritterhouse et al., "ROSI Rearrangement in Thyroid Cancer.", Thyroid, 26(6): 794-7, 2016.
Roblin et al., "Topical TrkA Kinase Inhibitor CT327 is an Effective, Novel Therapy for the Treatment of Pmritus due to Psoriasis: Results from Experimental Studies, and Efficacy and Safety of CT327 in a Phase 2b Clinical Trial in Patients with Psoriasis," Acta Denn. Venereal., 2015, 95:542-548.
Rosenbaum et al., "Next Generation Sequencing Reveals Genomic Heterogenity of ALK Fusion Breakpoints in Non-Small Cell Lung Cancer", Laboratory Investigation, vol. 96, Supp. SUPPL. 1, pp. 481A-482A, Abstract No. 1914, 105th Annual Meeting of the United States and Canadian Academy of Pathology, Seattle, WA, 2016.
Roskoski, Jr. et al., "Classification of small molecule protein kinase inhibitors based upon the structures of their drug-enzyme complexes," Pharmacological Research, 2016, 103: 26-48.
Rossi et al., "Abstract 84: RNA-Sequencing Identifies ETV6-NTRAK3 as a Gene Fusion Involved in Gastrointestinal Stromal Tumors," Meeting Info: 105th Annual Meeting of the United States and Canadian Academy of Pathology, Seattle, WA, Annual Meeting Abstracts, 24A (2016).
Rubin et al., "Congenital mesoblastic nephroma t(12;15) is associated with ETV6-NTRK3 gene fusion: cytogenetic and molecular relationship to congenital (infantile) fibrosarcoma," Am. J. Pathol, Nov. 1998, 153(5):1451-1458.
Russo et al., "Acquired Resistance to the Trk Inhibitor Entrectinib in Colorectal Cancer," Cancer Discovery, Jan. 1, 2016, 6(1):36-44.
Sahin et al., "Personalized RNA mutanome vaccines mobilize poly-specific therapeutic immunity against cancer.", Nature 547: 222-226, 2017.
Saborowski et al., "Mouse model of intrahepatic cholangiocarcinoma validates FIG-ROS as a potent fusion oncogene and therapeutic target.", Proc. Natl. Acad Sci. USA, 110(48): 19513-19518, 2013.
Saragovi et al., "A TrkA-selective, fast internalizing nerve growth factor-antibody complex induces trophic but not neuritogenic signals," J Biol Chem, Dec. 25, 1998;273(52):34933-34940.
Sartore-Bianchi et al., "Sensitivity to Entrectinib Associated With a Novel LMNA-NTRK1 Gene Fusion in Metastatic Colorectal Cancer," J. Natl. Cancer Inst, Nov. 2015, 108(1). doi: 10.1093/inci/div306.
Schmidt et al., "Heilmittelchemische untersuchungen in der Heterocyclischen Rihe. Pyrazolo-(3,4-D)-Pyrimidine (Medicinal chemical studies in the heterocyclic series. Pyrazolo-(3,4-D)-Pyrimidine)," Helvetica Chimica, Verlag Helvetica Chimica Acta, Jan. 1956, 39: 986-991 (with English Abstract).
Schmidt, Charles. "Combinations on trial." Nature 552.7685 (Dec. 21, 2017): S67-S69.
Schram et al., "Abstract LB-302: Potential role of larotrectinib (LOXO-101), a selective pan-TRK inhibitor, in NTRK fusion-positive recurrent glioblastoma, "Cancer Research, Jul. 2017, DOI: 10.1158/1538-7445.AM2017-LB-302, 2 pages.
Schrock et al., "Gastrointestinal tumours, non-colorectal", Annals of Oncology. vol. 27, Suppl 6, 6130, 2016.
Shaver et al., "Diverse, Biologically Relevant, and Targetable Gene Rearrangements in Triple-Negative Breast Cancer and Other Malignancies.", Cancer Res, 76(16): 4850-60, 2016.
Shaw et al., "Ceritinib in ALK-rearranged non-small-cell lung cancer," N Engl J Med, Mar. 27, 2014;370(13):1189-97. doi: 10.1056/NEJMoal3ll 107.
Shaw et al., "Crizotinib in ROSI-rearranged non-small-cell lung cancer," N Engl J Med, Nov. 20, 2014;371(21):1963-71. doi: 10.1056/NEJMoal406766. Epub Sep. 27, 2014.
Sheldrick, "A short history of SHELX," Acta Crystallogr A, Jan. 2008, 64(Ptl): 112-122.
Sigal, et al., "Activity of Entrectinib in a Patient with the First Reported NTRK Fusion in Neuroendocrine Cancer," J. Natl. Compr. Cane. Netw, Nov. 2017, 15(11): 1317-1322.
Sims et al., Abstract P280: Profiling abscopal regression in a pediatric fibrosarcoma with a novel EML4-NTRK3 fusion using

(56) References Cited

OTHER PUBLICATIONS immunogenomics and high-dimensional histopathology, J mmunotherapy of Cancer, Nov. 2016, 4(Sl): 73.
Skalova et al., "Mammary Analogue Secretory Carcinoma of Salivary Glands: Molecular Analysis of 25 ETV6 Gene Rearranged Tumors with Lack of Detection of Classical ETV6-NTRK3 Fusion Transcript by Standard RT-PCR: Report of 4 Cases Harboring ETV6-X Gene Fusion," Am. J. Surg. Pathol, Jan. 2016, 40(1):3-13.
Skalova et al., "Molecular Profiling of Mammary Analog Secretory Carcinoma Revealed a Subset of Tumors Harboring a Novel ETV6-RET Translocation: Report of 10 Cases," Am. J. Surg. Pathol, Feb. 2018, 42(2):234-246.
Song et al., "Molecular Changes Associated with Acquired Resistance to Crizotinib in ROS1-Rearranged Non-Small Cell Lung Cancer.", Clin. Cancer Res., 21(10): 2379-87, 2015.
Subramaniam et al., Abstract 2019: RNA-Seq analysis of glioma tumors to reveal targetable gene fusions, 2017 Annual Meeting of the American Society of Clinical Oncology,2017, 1 page.
Sun et al., "P-loop conformation governed crizotinib resistance in G2032R-mutated ROSI tyrosine kinase: clues from free energy landscape," PLoS computational biology, Jul. 17 2014, 10(7): e1003729.
Tahira et al., "dbQSNP: a database of SNPs in human promoter regions with allele frequency information determined by single-strand conformation polymorphism-based methods," Hum Mutat, Aug. 2005;26(2):69-77.
Tan et al., "Genetic landscape of ALK+ non-small cell lung cancer (NSCLC) patients (pts) and response to ceritinib in ASCEND-I", J Clin. Oncology, vol. 34, Supp. Supplement 15, Abstract No. 9064, 2016 Annual Meeting of the American Society of Clinical Oncology, Chicago, IL, 2016.
Tannenbaum, et al., "Abstract 749: Characterization of a Novel Fusion Gene, EML4-NTRK3, in Infantile Fibrosarcoma," Pediatr Blood Cancer, DOI 10.1002/pbc, 1 page. 2015.
Taylor et al., "Abstract 794: Characterization of NTRK fusions and Therapeutic Response to NTRK Inhibition in Hematologic Malignancies," Blood, 2017, 130: 794.
The Cancer Genome Atlas Network, "Comprehensive Molecular Characterization of Human colon and Rectal Cancer," Nature, Jan. 2013, 487(7407): 330-337.
Thress et al., "Identification and preclinical characterization of AZ-23, a novel, selective, and orally bioavailable inhibitor of the Trk kinase pathway," Mol Cancer Ther, Jul. 2009:8(7):1818-27. doi: 10.1158/1535-7163.MCT-09-0036. Epub Jun. 9, 2009.
Turtle et al., "Artificial antigen-presenting cells for use in adoptive immunotherapy," Cancer J, Jul.-Aug. 2010;16(4):374-81. doi: 10.1097/PPO.0b013e3181eb33a6.
Vanden et al., "endocrine and neuroendocrine tumours", Annals of Oncology, vol. 27, Supp. Supplement 6. Abstract No. 427PD' 4pt European Society for Medical Oncology Congress, ESMO 2016; Copenhagen, Denmark; Oct. 7-11, 2016.
Vippagunta et al., "Crystalline Solids" Advanced Drug Delivery Rev., 2001, 48(1): 3-26.
Vogelstein and Kinzler, The Genetic Basis of Human Cancer, 2nd ed., 2002, ng 3, col. 1, para 2.
Walther et al., "Cytogenetic and single nucleotide polymorphism array findings in soft tissue tumors in infants," Cancer Genet, Jul.-Aug. 2013, 206(7-8): 299-303.
Wang et al., "Design, synthesis and biological evaluation of novel 4-arylaminopyrimidine derivatives possessing a hydrazone moiety as dual inhibitors of L1196M ALK and ROS1.", Eur. J Med Chem., 123, 80-99, 2016.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "Identification of NTRK3 fusions in childhood melanocytic neoplasms," J. Mol. Diagn, May 2017, 19(3):387-396.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-0ll-1912-5. Epub Dec. 16, 2011.
Wang, "Pan-cancer analysis of ROSI genomic aberrations", University of Hong Kong, Pokfulam, Hong Kong SAR (Thesis), 44 pages, 2015.
Watanbe et al., "Cryptic t(l2;15)(pl3;q26) producing the ETV6-NTRK3 fusion gene and no loss of IGF2 imprinting in congenital mesoblastic nephroma with trisomy 11: fluorescence in situ hybridization and IGF2 allelic expression analysis," Cancer Genet. Cytogenet, Jul. 2002, 136(1):10-16.
Wei et al., "Abstract #2136: Entrectinib is Effective Against the Gatekeeper and Other Emerging Resistance Mutations in NTRK-, ROSI- and ALK- Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wei et al., "Abstract 78: Entrectinib, a highly potent pan-Trk, and ALK inhibitor, has broad-spectrum, histology-agnostic anti-tumor activity in molecularly defined cancers," 28thEORTC-NCI-AACR Symposium on Molecular Targets and Cancer Therapeutics, Munich, Germany, 2016, 1 page.
Wen et al, "Updated response assessment criteria for high-grade gliomas: response assessment in neuro-oncology working group," J Clin Oncol, Apr. 2010, 28(11): 1963-1972.
Wittwer et al., "High-resolution genotyping by amplicon melting analysis using LCGreen," Clin Chem, Jun. 2003;49(6 Pt 1):853-60.
Wlodarska et al., "ALK-Positive Anaplastic Large Cell Lymphoma with the Variant EEF1G-, RNF213- and Atic-ALK Fusions Is Featured by Copy Number Gain of the Rearranged ALK Gene", Blood, vol. 126(23): 3654, 57th Annual Meeting of the American Society of Hematology, San Diego, CA, 2015.
Won et al., "Post-crizotinib management of effective ceritinib therapy in a patient with ALK-positive non-small cell lung cancer", BMC Cancer, 16: 568, 2016.
Woodward, "Bi-allelic SNP genotyping using the TaqMan® assay," Methods Mol Biol., 2014;1145:67-74. doi: 10.1007/978-1-4939-0446-4 6.
Yakirevich et al., " Colorectal Adenocarcinoma with ALK Rearrangement: Clinicopathologic and Molecular Characteristics", Laboratory Investigation, vol. 96, Supp. SUPPL. 1, pp. 209A, Abstract No. 827, 105th Annual Meeting of the United States and Canadian Academy of Pathology, Seattle, WA, 2016.
Yakirevich et al., "Oncogenic ALK Fusion in Rare and Aggressive Subtype of Colorectal Adenocarcinoma as a Potential Therapeutic Target.", Clin Cancer Res, 22(15): 3831-40, 2016.
Yamamoto et al., "ALK, ROS1 and NTRK3 gene rearrangements in inflammatory myofibroblastic tumours.", Histopathology, 69(1): 72-83, 2016.
Yamamoto et al., "Anaplastic lymphoma kinase-positive squamous cell carcinoma of the lung: A case report.", Mal Clin. Oneal. 5(1): 61-63, 2016.
Ying et al., "Atypical negative ALK FISH accompanied by immunohistochemistry positivity harbored various ALK rearrangements in NSCLC patients and respond to targeted therapy.", J Clin. Oncology, vol. 34, Supp. Supplement 15, Abstract No. e20506, 2016 Annual Meeting of the American Society of Clinical Oncology, Chicago, IL, 2016.
Yu et al., "Denaturing high performance liquid chromatography: high throughput mutation screening in familial hypertrophic cardiomyopathy and SNP genotyping in motor neurone disease," J Clin Pathol, May 2005;58(5):479-85.
Yu et al., "Detection of ALK rearrangements in lung cancer patients using a homebrew PCR assay", Oncotarget, 8(5): 7722-7728, 2016.
Zage et al., "The selective TRK inhibitor AZ623 inhibits brain-derived neurotrophic factor-mediated neuroblastoma cell proliferation and signaling and is synergistic with topotecan," Cancer, Mar. 2011, 117(6): 1321-1391.
Zehir et al., "Mutational landscape of metastatic cancer revealed from prospective clinical sequencing of 10,000 patients," Nat. Med, Jun. 2017, 23(6):703-713.
Zhang et al., "A novel multiplex tetra-primer ARMS-PCR for the simultaneous genotyping of six single nucleotide polymorphisms

(56) References Cited

OTHER PUBLICATIONS associated with female cancers," PLoS One, Apr. 17, 2013;8(4):e62126. doi: 10.1371/journal.pone.0062126. Print 2013.

Zhang et al., "Whole-genome sequencing identifies genetic alterations in pediatric low-grade gliomas," Nat. Genet., Jun. 2013, 45(6): 602-612.

Zhu et al., "TPD52L1-ROS1, a new ROS1 fusion variant in lung adenosquamous cell carcinoma identified by comprehensive genomic profiling", Lung Cancer, 97:48-50, doi: 10.1016/j.lungcan.2016.04.013, 2012.

Ziemiecki et al., "Oncogenic activation of the human trk proto-oncogene by recombination with the ribosomal large subunit protein L7a," EMBO J, Jan. 1990, 9(1):191-196.

Zou et al., "PF-06463922 is a potent and selective next-generation ROS1/ALK inhibitor capable of blocking crizotinib-resistant ROS1 mutations.", Proc. Natl. Acad Sci. USA., 112(11): 3493-8, 2015.

\* cited by examiner

Unpolarised light

Polarised light

A

B

CRYSTALLINE FORM OF (S)-N-(5-((R)-2-(2,5-DIFLUOROPHENYL)-PYRROLIDIN-1-YL)-PYRAZOLO[1,5-A]PYRIMIDIN-3-YL)-3-HYDROXYPYRROLIDINE-1-CARBOXAMIDE HYDROGEN SULFATE

CROSS-REFERENCE TO RELATED APPLICATIONS

This application claims priority to U.S. Provisional Application Ser. Nos. 62/080,374, filed Nov. 16, 2014, and 62/169,545, filed Jun. 1, 2015, both of which are incorporated in their entireties herein.

BACKGROUND

1. Field of the Invention

The present disclosure relates to (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide (Formula I) and to pharmaceutically acceptable salts thereof, for example the hydrogen sulfate salt, and further to a novel crystalline form of the hydrogen sulfate salt, which exhibit Trk family protein tyrosine kinase inhibition, pharmaceutical compositions containing the same, processes of making the crystalline form, and the use of the compound and crystalline form in the treatment of pain, inflammation, cancer, and certain infectious diseases.

2. Description of the Related Art

Trk's are the high affinity receptor tyrosine kinases activated by a group of soluble growth factors called neurotrophins (NT). The Trk receptor family has three members—TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., Current Opinion in Neurobiology, 2001, 11, 272-280).

Recent literature has shown that overexpression, activation, amplification and/or mutation of Trk's are associated with many cancers including neuroblastoma (Brodeur, G. M., Nat. Rev. Cancer 2003, 3, 203-216), ovarian cancer (Davidson., B. et al., Clin. Cancer Res. 2003, 9, 2248-2259), breast cancer (Kruettgen et al., Brain Pathology 2006, 16: 304-310), prostate cancer (Dionne et al., Clin. Cancer Res. 1998, 4(8): 1887-1898), pancreatic cancer (Dang et al., Journal of Gastroenterology and Hepatology 2006, 21(5): 850-858), multiple myeloma (Hu et al., Cancer Genetics and Cytogenetics 2007, 178: 1-10), astrocytoma and medulloblastoma (Kruettgen et al., Brain Pathology 2006, 16: 304-310), glioma (Hansen et al., Journal of Neurochemistry 2007, 103: 259-275), melanoma[25], thyroid carcinoma (Brzezianska et al., Neuroendocrinology Letters 2007, 28(3), 221-229), lung adenocarcinoma (Perez-Pinera et al., Molecular and Cellular Biochemistry 2007, 295(1&2), 19-26), large cell neuroendocrine tumors[19] (Marchetti et al., Human Mutation 2008, 29(5), 609-616), and colorectal cancer (Bardelli, A., Science 2003, 300, 949). In preclinical models of cancer, Trk inhibitors are efficacious in both inhibiting tumor growth and stopping tumor metastasis. In particular, non-selective small molecule inhibitors of TrkA, TrkB, TrkC and Trk/Fc chimeras were efficacious in both inhibiting tumor growth and stopping tumor metastasis[25] (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E. et al. *Cancer Res* (2008) 68:(2) 346-351). Therefore, an inhibitor of the Trk family of kinases is expected to have utility in the treatment of cancer.

In addition, inhibitors of the Trk/neurotrophin pathway have been demonstrated to be effective in numerous pre-clinical animal models of pain. For example, antagonistic NGF and TrkA antibodies (for example, RN-624) have been shown to be efficacious in inflammatory and neuropathic pain animal models and in human clinical trials (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448). Additionally, recent literature indicates after inflammation, BDNF levels and TrkB signaling is increased in the dorsal root ganglion (Cho, L. et al. Brain Research 1997, 749, 358) and several studies have shown antibodies that decrease signaling through the BDNF/TrkB pathway inhibit neuronal hypersensitization and the associated pain (Chang-Qi, L et al. Molecular Pain 2008, 4:27).

It has been shown that NGF secreted by tumor cells and tumor invading macrophages directly stimulates TrkA located on peripheral pain fibers. Using various tumor models in both mice and rats it was demonstrated that neutralizing NGF with a monoclonal antibody inhibits cancer related pain to a degree similar or superior to the highest tolerated dose of morphine. In addition, activation of the BDNF/TrkB pathway has been implicated in numerous studies as a modulator of various types of pain including inflammatory pain (Matayoshi, S., J. Physiol. 2005, 569: 685-95), neuropathic pain (Thompson, S. W., Proc. Natl. Acad. Sci. USA 1999, 96:7714-18) and surgical pain (Li, C.-Q. et al., Molecular Pain, 2008, 4(28), 1-11). Because TrkA and TrkB kinases may serve as a mediator of NGF driven biological responses, inhibitors of TrkA and/or other Trk kinases may provide an effective treatment for chronic pain states.

The current treatment regimes for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

In addition, inhibition of the neurotrophin/Trk pathway has been shown to be effective in treatment of pre-clinical models of inflammatory diseases. For example, inhibition of the neurotrophin/Trk pathway has been implicated in pre-clinical models of inflammatory lung diseases including asthma (Freund-Michel, V; Frossard, N.; *Pharmacology & Therapeutics* (2008), 117(1), 52-76), interstitial cystitis (Hu Vivian Y; et. al. *The Journal of Urology* (2005), 173(3), 1016-21), inflammatory bowel diseases including ulcerative colitis and Crohn's disease (Di Mola, F. F., et. al., Gut (2000), 46(5), 670-678) and inflammatory skin diseases such as atopic dermatitis (Dou, Y.-C.; et. al. *Archives of Dermatological Research* (2006), 298(1), 31-37), eczema and psoriasis (Raychaudhuri, S. P.; et. al. Journal of Investigative Dermatology (2004), 122(3), 812-819).

The neurotrophin/Trk pathway, particularly BDNF/TrkB, has also been implicated in the etiology of neurodegenerative diseases including multiple sclerosis, Parkinson's disease and Alzheimer's disease (Sohrabji, Farida; Lewis, Danielle K. Frontiers in Neuroendocrinology (2006), 27(4), 404-414). Modulation of the neutrophin/Trk pathway may have utility in treatment of these and related diseases.

The TrkA receptor is also thought to be critical to the disease process in the infection of the parasitic infection of *Trypanosoma cruzi* (Chagas disease) in human hosts (de Melo-Jorge, M. et al. *Cell Host & Microbe* (2007), 1(4), 251-261). Thus, TrkA inhibition may have utility in treating Chagas disease and related protozoan infections.

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer(1) and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA and TrkC receptors has been observed in the bone forming area in mouse models of bone fracture (K. Asaumi, et al., Bone (2000) 26(6) 625-633). In addition, localization of NGF was observed in almost all bone forming cells (K. Asaumi, et al.). Recently, it was demonstrated that a pan-Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Several classes of small molecule inhibitors of Trk kinases said to be useful for treating pain or cancer are known (*Expert Opin. Ther. Patents* (2009) 19(3)).

International Patent Application Publications WO 2006/115452 and WO 2006/087538 describe several classes of small molecules said to be inhibitors of Trk kinases which could be useful for treating pain or cancer.

Pyrazolo[1,5-a]pyrimidine compounds are known. For example, International Patent Application Publication WO 2008/037477 discloses pyrazolo[1,5-a]pyrimidine compounds bearing an alkyl, aryl or heterocyclic group at the 3-position. These compounds are asserted to be PI3K and/or mTOR Lipid Kinase inhibitors.

PCT Patent Publication No. WO 2008/058126 discloses pyrazolo[1,5-a]pyrimidine compounds bearing a phenyl group at the 3-position. These compounds are asserted to be Pim-kinase inhibitors.

U.S. Patent Publication No. 2006/0094699 discloses pyrazolo[1,5-a]pyrimidine compounds bearing a —C(=O)NH-phenyl, —C(=O)(4-methylpiperidinyl) or —C(=O)NMe ($CH_2$-trimethylpyrazolyl) group at the 3-position for use in combination therapy with a glucocorticoid receptor agonist.

PCT Patent Publication Nos. WO 2010/033941, WO 2010/048314, WO 2011/006074, and WO 2011/146336 disclose compounds which exhibit Trk family protein tyrosine kinase inhibition, and which are useful in the treatment of pain, cancer, inflammation, neurodegenerative diseases and certain infectious diseases.

WO 2010/048314 discloses in Example 14A a hydrogen sulfate salt of (S)—N-(5((R)-2-(2,5-difluorophenyl)-pyrrolidin-1-yl)-pyrazolo[1,5-a]pyrimidin-3-yl)-3-hydroxypyrrolidine-1-carboxamide. WO 2010/048314 does not disclose the particular form of the hydrogen sulfate salt described herein when prepared according to the method of Example 14A in that document. In particular, WO 2010/048314 does not disclose crystalline form (I-HS) as described below.

All documents, including scientific articles, patent publications and applications, and the like, referenced in the present disclosure are hereby incorporated by reference in their entirety.

SUMMARY

The present disclosure relates to (S)—N-(5((R)-2-(2,5-difluorophenyl)-pyrrolidin-1-1)-pyrazolo[1,5-a]pyrimidin-3-yl)-3-hydroxypyrrolidine-1-carboxamide (Formula I) and to pharmaceutically acceptable salts thereof, for example the hydrogen sulfate salt, and further to a novel crystalline form of the hydrogen sulfate salt, which exhibit Trk family protein tyrosine kinase inhibition, pharmaceutical compositions containing the same, processes of making the crystalline form, and the use of the compound and crystalline form in the treatment of pain, inflammation, cancer, and certain infectious diseases.

Provided herein is a novel crystalline form of the compound of Formula I:

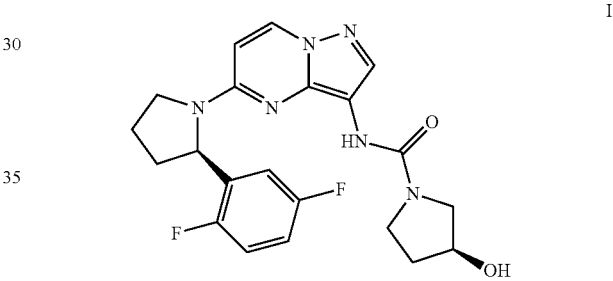

also known as (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide. In particular, the novel crystalline form comprises the hydrogen sulfate salt of the compound of Formula I in a stable polymorph form, hereinafter referred to as crystalline form (I-HS) and LOXO-101, which can be characterized, for example, by its X-ray diffraction pattern—the crystalline form (I-HS) having the formula:

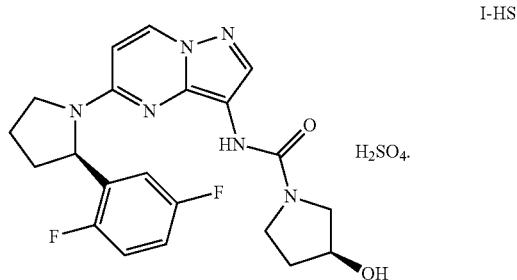 [SMILES: O=C(Nc1cnn2ccc(N3CCC[C@@H]3c3cc(F)ccc3F)nc12)N1CC[C@H](O)C1]

In some embodiments, crystalline form (I-HS) is characterized by having XRPD diffraction peaks (2θ degrees) at 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2. In some embodiments, crystalline form (I-HS) is characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2. 24.4±0.2, 25.6±0.2, 26.5±0.2, 27.6±0.2, 28.2±0.2, 28.7±0.2, 30.8±0.2, and 38.5±0.2.

In some embodiments, the crystalline form (I-HS) has XRPD pattern substantially as shown in FIG. 29.

In some embodiments, the crystalline form exhibits an onset to maximum of about 193 to about 205° Celsius, as measured by differential scanning calorimetry. In some embodiments, the crystalline form (I-HS) exhibits a heat of melting of about 2.415 mW, as measured by differential scanning calorimetry. In some embodiments, the crystalline form (I-HS) has a DSC thermogram substantially as shown in FIG. 26. In some embodiments, the crystalline form (I-HS) is non-hygroscopic.

Some embodiments include a pharmaceutical composition comprising a pharmaceutically acceptable carrier and crystalline form (I-HS). Some embodiments include a pharmaceutical composition made by mixing crystalline form (I-HS) and a pharmaceutically acceptable carrier. Some embodiments include a process of making a pharmaceutical composition comprising mixing crystalline form (I-HS) and a pharmaceutically acceptable carrier.

The present disclosure also relates to methods for the treatment of cancer, pain, inflammation, and certain infectious diseases comprising administering to a subject in need thereof a therapeutically effective amount of crystalline form (I-HS). Some embodiments include the use of crystalline form (I-HS) in the preparation of a medicament for treating cancer, pain, inflammation, and certain infectious diseases, in a subject in need thereof.

Also provided herein is a method of treating a cancer mediated by a Trk kinase in a subject in need thereof, the method comprising administering to the subject a therapeutically effective amount of crystalline form (I-HS). In some embodiments, the cancer is mediated by Trk; TrkB; or TrkA and TrkB. In some embodiments, a patient is diagnosed or identified as having a Trk-associated cancer.

Further provided herein is a method for treating cancer in a subject in need thereof, the method comprising: (a) determining if the cancer is associated with one or more of overexpression, activation, amplification, and mutation of a Trk kinase; and (b) if the cancer is determined to be associated with one or more of overexpression, activation, amplification, and mutation of a Trk kinase, administering to the subject a therapeutically effective amount of crystalline form (I-HS). In some embodiments, a method for treating cancer in a subject in need thereof is provided, the method comprising: (a) determining if the cancer is mediated by a Trk kinase; and (b) if the cancer is determined to be mediated by a Trk kinase, administering to the subject a therapeutically effective amount of crystalline form (I-HS). Also provided herein is a method of treating a subject comprising: (a) performing an assay on a sample obtained from the subject to determine whether the subject has dysregulation of a NTRK gene, a Trk protein, or expression or level of the same; and (b) administering to a subject determined to have dysregulation of a NTRK gene, a Trk protein, or expression or activity, or level of the same a therapeutically effective amount of crystalline form (I-HS).

In some embodiments, the dysregulation of a NTRK gene, a Trk protein, or expression or level of the same is a chromosome translation that results in the translation of a Trk fusion protein. For example, the Trk fusion protein is selected from the group consisting of: TP53-TrkA, LMNA-TrkA, CD74-TrkA, TFG-TrkA, TPM3-TrkA, NFASC-TrkA, BCAN-TrkA, MPRIP-TrkA, TPR-TrkA, RFWD2-TrkA, IRF2BP2-TrkA, SQSTM1-TrkA, SSBP2-TrkA, RABGAP1L-TrkA, C18ORF8-TrkA, RNF213-TrkA, TBC1D22A-TrkA, C200RF112-TrkA, DNER-TrkA, ARHGEF2-TrkA, CHTOP-TrkA, PPL-TrkA, PLEKHA6-TrkA, PEAR1-TrkA, MRPL24-TrkA, MDM4-TrkA, LRRC71-TrkA, GRIPAP1-TrkA, EPS15-TrkA, DYNC2H1-TrkA, CEL-TrkA, EPHB2-TrkA, TGF-TrkA, NACC2-TrkB, QKI-TrkB, AFAP1-TrkB, PAN3-TrkB, SQSTM1-TrkB, TRIM24-TrkB, VCL-TrkB, AGBL4-TrkB, DAB2IP-TrkB, ETV6-TrkC, BTBD1-TrkC, LYN-TrkC, RBPMS-TrkC, EML4-TrkC, HOMER2-TrkC, TFG-TrkC, FAT1-TrkC, and TEL-TrkC.

In some embodiments, the dyregulation of a NTRK gene, a Trk protein, or expression or activity of the same is one or more point mutation in the gene. For example, the NTRK gene is a NTRK1 gene, and the one or more point mutations in the NTRK1 gene results in the translation of a TrkA protein having substitutions are one or more of the following amino acid positions: 33, 336, 337, 324, 420, 444, 517, 538, 649, 682, 683, 702, and 1879. In some embodiments, the one or more point mutations in the NTRK1 gene results in the translation of a TrkA protein having one or more of the following amino acid substitutions: R33W, A336E, A337T, R324Q, R324W, V420M, R444Q, R444W, G517R, G517V, K538A, R649W, R649L, R682S, V683G, V702C, and C1879T.

The features and advantages described in this summary and the following detailed description are not all-inclusive. Many additional features and advantages will be apparent to one of ordinary skill in the art in view of the drawings, specification, and claims hereof.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The present disclosure relates to (S)—N-(5((R)-2-(2,5-difluorophenyl)-pyrrolidin-1-1)-pyrazolo[1,5-a]pyrimidin-3-yl)-3-hydroxypyrrolidine-1-carboxamide (Formula I) and to pharmaceutically acceptable salts thereof, for example the hydrogen sulfate salt, and further to a novel crystalline form of the hydrogen sulfate salt, which exhibit Trk family protein tyrosine kinase inhibition, pharmaceutical compositions containing the same, and processes of making the crystalline form.

Provided herein is a novel crystalline form of the compound of Formula I:

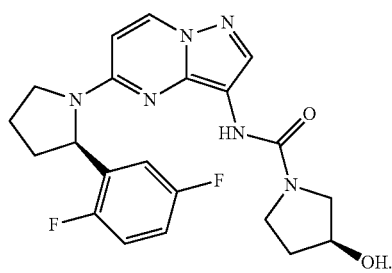

In particular, the novel crystalline form comprises the hydrogen sulfate salt of the compound of Formula I in a stable polymorph form, hereinafter referred to as crystalline form (I-HS), which may be characterized, for example, by its X-ray diffraction pattern.

Figure 1:
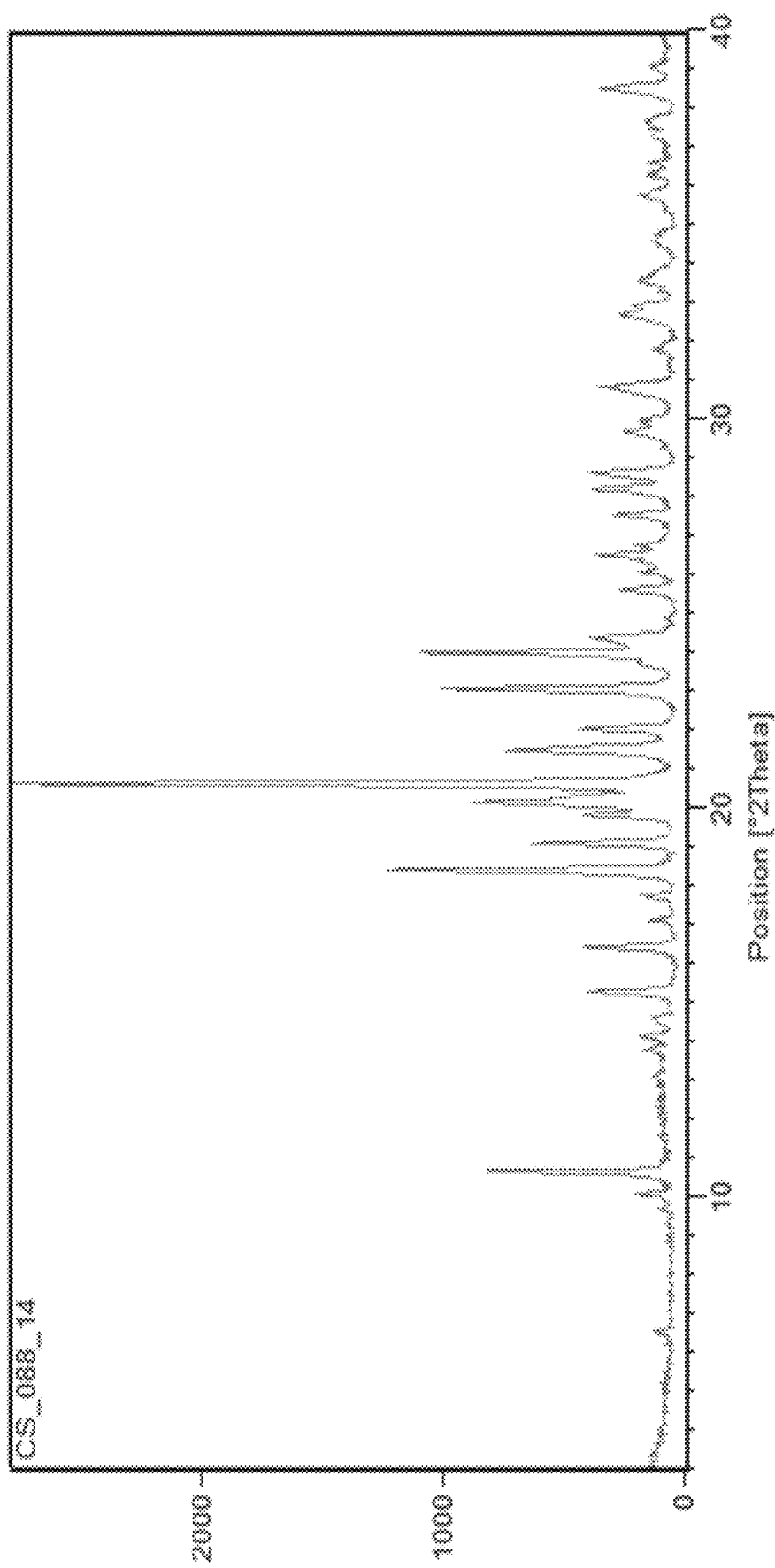
FIG. 1 illustrates an X-ray powder diffraction (XRPD) pattern of crystalline form (I-HS) prepared according to Example 2, according to one embodiment.

As illustrated in FIG. 1, in some embodiments, the crystalline form (I-HS) can be characterized by its X-ray powder diffraction pattern (XRPD). The XRPD was carried out on a D5000 X-ray diffractometer with a CuKα1, 0.1540562 nm long, fine focus sealed tube source from Siemens by scanning samples between 3 and 40° 2-theta at a step size of 0.0200° 2-theta and a time per step of 1 second. The effective scan speed was 0.0200°/s with an instrument voltage 40 kV and a current setting of 40 mA. Samples were analyzed using a divergence slit having a size of 2 mm in reflection mode under the following experimental conditions.

In some embodiments, crystalline form (I-HS) has an XRPD pattern with at least the 20 characteristic peaks (2θ degrees±0.3), as listed in Table 1.

TABLE 1

XRPD peaks of crystalline form (I-HS)

| Position [°2-θ] | FWHM [°2-θ] | d-spacing [Å] | Relative Intensity [%] |
|---|---|---|---|
| 10.63 | 0.12 | 8.32 | 27.44 |
| 15.25 | 0.14 | 5.81 | 12.24 |
| 16.39 | 0.13 | 5.40 | 13.92 |
| 18.37 | 0.13 | 4.82 | 43.65 |
| 19.08 | 0.14 | 4.65 | 19.60 |
| 19.79 | 0.11 | 4.48 | 9.83 |
| 20.15 | 0.25 | 4.40 | 25.09 |
| 20.61 | 0.13 | 4.31 | 100.00 |
| 21.47 | 0.21 | 4.14 | 24.71 |
| 22.01 | 0.12 | 4.03 | 14.45 |
| 23.04 | 0.15 | 3.86 | 33.01 |
| 23.97 | 0.12 | 3.71 | 38.52 |
| 24.35 | 0.21 | 3.65 | 10.05 |
| 25.58 | 0.13 | 3.48 | 8.11 |
| 26.48 | 0.17 | 3.36 | 9.76 |
| 27.50 | 0.14 | 3.24 | 7.70 |
| 28.17 | 0.17 | 3.16 | 11.60 |
| 28.58 | 0.19 | 3.12 | 10.85 |
| 30.77 | 0.29 | 2.90 | 8.48 |
| 38.47 | 0.21 | 2.34 | 10.97 |

In some embodiments, the crystalline form (I-HS) has an XRPD pattern with at least the 8 characteristic peaks (2θ degrees±0.3), which comprises peaks having a relative intensity greater than or equal to about 15%, as listed in Table 2.

TABLE 2

XRPD peaks of crystalline form (I-HS)

| Position [°2-θ] | FWHM [°2-θ] | d-spacing [Å] | Relative Intensity [%] |
|---|---|---|---|
| 10.63 | 0.12 | 8.32 | 27.44 |
| 18.37 | 0.13 | 4.82 | 43.65 |
| 19.08 | 0.14 | 4.65 | 19.60 |
| 20.15 | 0.25 | 4.40 | 25.09 |
| 20.61 | 0.13 | 4.31 | 100.00 |
| 21.47 | 0.21 | 4.14 | 24.71 |
| 23.04 | 0.15 | 3.86 | 33.01 |
| 23.97 | 0.12 | 3.71 | 38.52 |

In some embodiments, the crystalline form (I-HS) has an XRPD pattern with at least the 5 characteristic peaks (2θ degrees±0.3), which comprises peaks having a relative intensity greater than or equal to about 25%, as listed in Table 3.

TABLE 3

XRPD peaks of crystalline form (I-HS)

| Position [°2-θ] | FWHM [°2-θ] | d-spacing [Å] | Relative Intensity [%] |
|---|---|---|---|
| 10.63 | 0.12 | 8.32 | 27.44 |
| 18.37 | 0.13 | 4.82 | 43.65 |
| 20.61 | 0.13 | 4.31 | 100.00 |

TABLE 3-continued

XRPD peaks of crystalline form (I-HS)

| Position [°2-θ] | FWHM [°2-θ] | d-spacing [Å] | Relative Intensity [%] |
|---|---|---|---|
| 23.04 | 0.15 | 3.86 | 33.01 |
| 23.97 | 0.12 | 3.71 | 38.52 |

In some embodiments, the crystalline form (I-HS) has an XRPD pattern with at least the 4 characteristic peaks (2θ degrees±0.3), which comprises peaks having a relative intensity greater than or equal to about 30%, as listed in Table 4.

TABLE 4

XRPD peaks of crystalline form (I-HS)

| Position [°2-θ] | FWHM [°2-θ] | d-spacing [Å] | Relative Intensity [%] |
|---|---|---|---|
| 18.37 | 0.13 | 4.82 | 43.65 |
| 20.61 | 0.13 | 4.31 | 100.00 |
| 23.04 | 0.15 | 3.86 | 33.01 |
| 23.97 | 0.12 | 3.71 | 38.52 |

In certain embodiments, crystalline form (I-HS) has an XRPD pattern that is substantially the same XRPD pattern as shown in FIG. 1.

In some embodiments, crystalline form (I-HS) is characterized by having XRPD diffraction peaks (2θ degrees) at about 18.4, 20.6, 23.0, and 24.0. In some embodiments, crystalline form (I-HS) is characterized by having XRPD diffraction peaks (2θ degrees) at about 10.6, 18.4, 20.6, 23.0, and 24.0. In some embodiments, crystalline form (I-HS) is characterized by having XRPD diffraction peaks (2θ degrees) at about 10.6, 18.4, 19.1, 20.2, 20.6, 21.5, 23.0, and 24.0. In some embodiments, crystalline form (I-HS) is characterized by having XRPD diffraction peaks (2θ degrees) at about 10.6, 15.3, 16.4, 18.4, 19.1, 19.8, 20.2, 20.6, 21.5, 22.0, 23.0, 24.0, 24.4, 25.6, 26.5, 27.5, 28.2, 28.6, 30.8, and 38.5.

Figure 29:
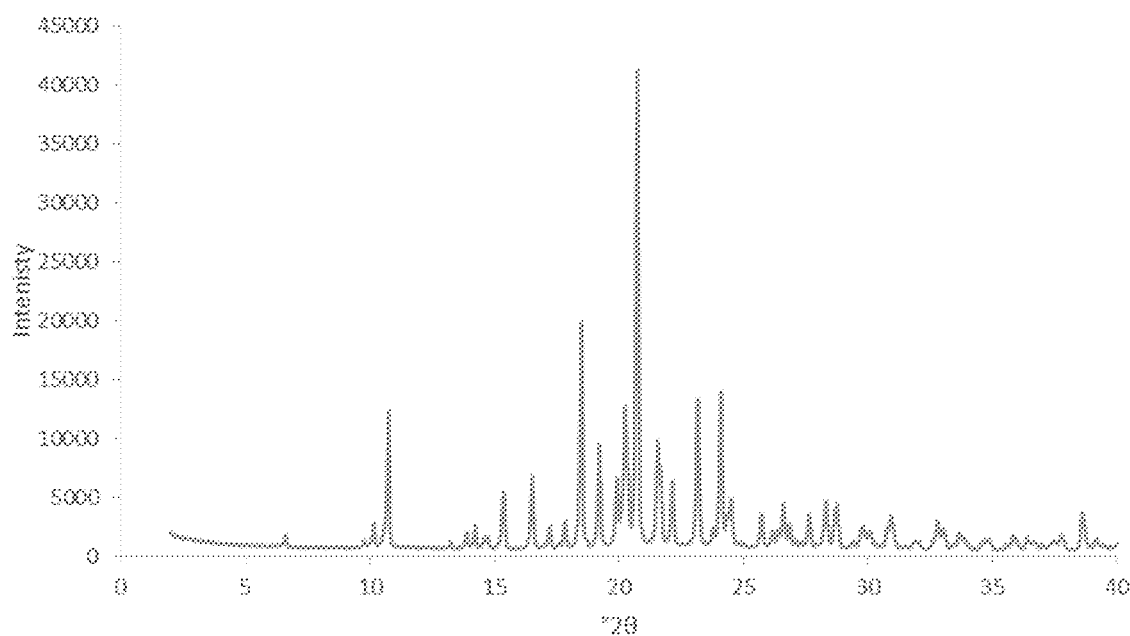
FIG. 29 illustrates an X-ray powder diffraction (XRPD) pattern of crystalline form (I-HS).
Figure 30:
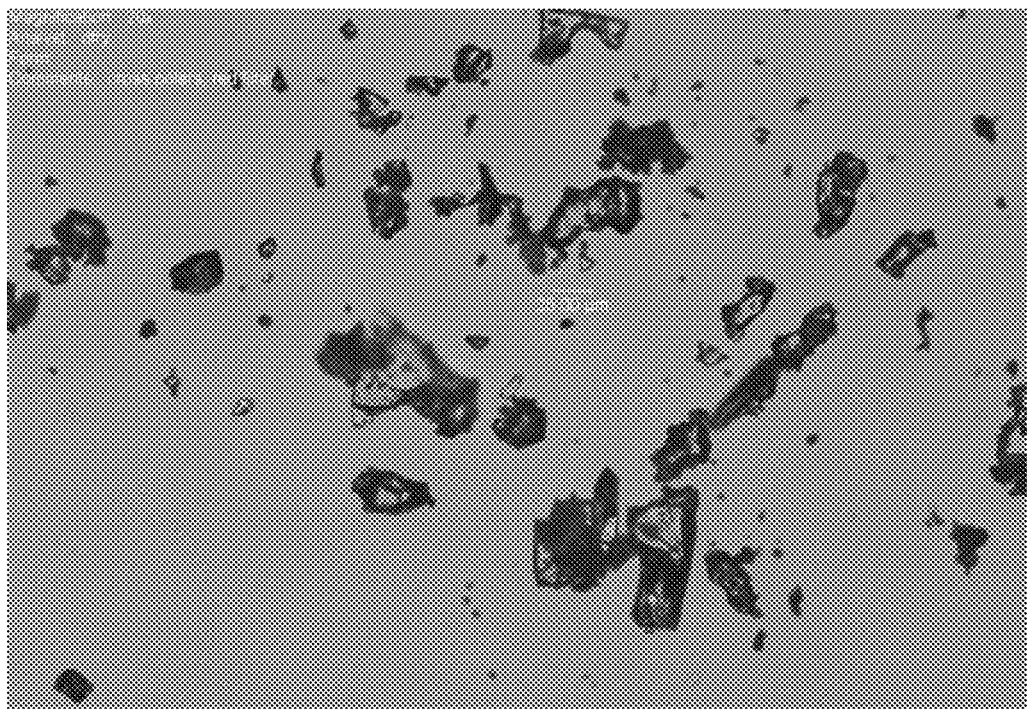
FIG. 30 is an image of a sample of AM(HS)1 under polarized light microscopy at a magnification of 20×.
Figure 31:
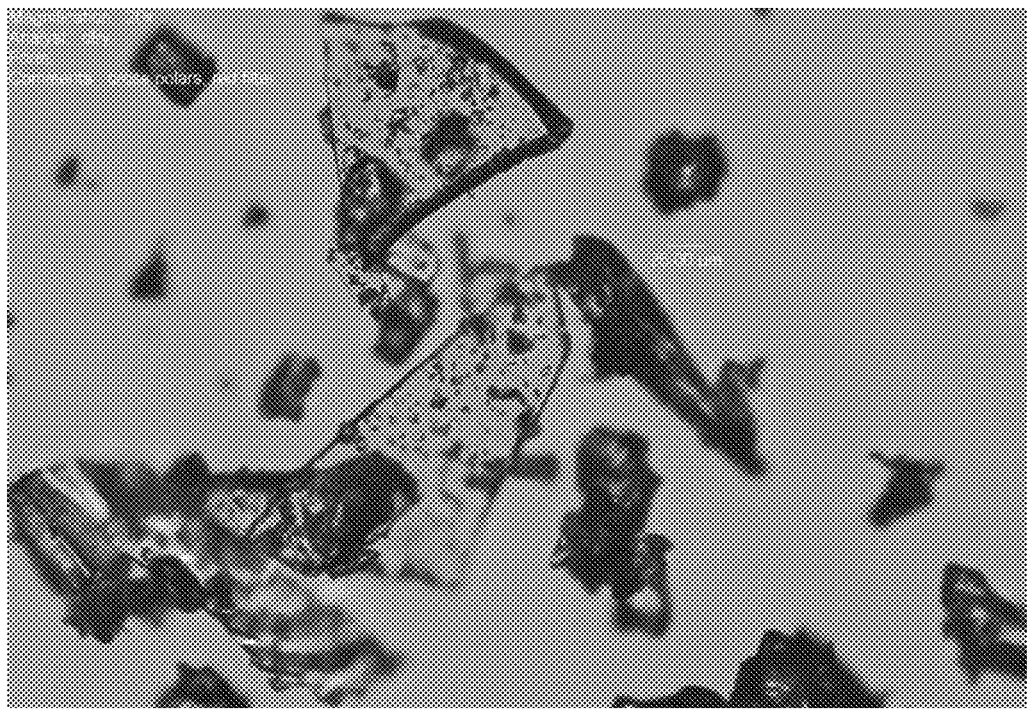
FIG. 31 is an image of a sample of AM(HS)2 under polarized light microscopy at a magnification of 20×.
Figure 32:
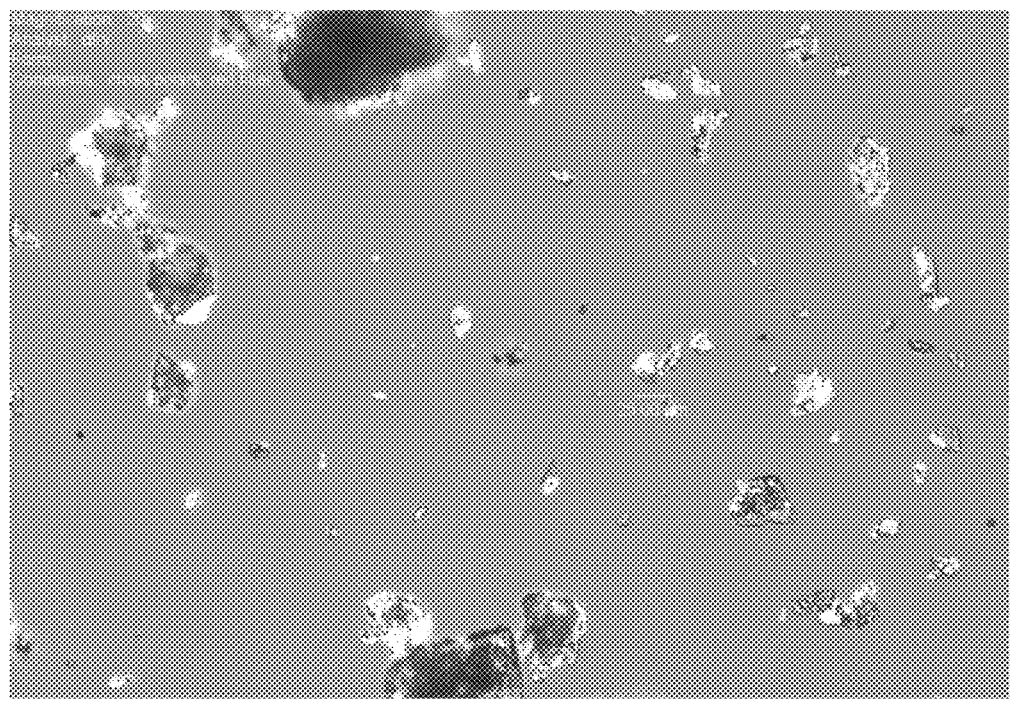
FIG. 32 is an image of a sample of crystalline form (I-HS) under polarized light microscopy at a magnification of 20×.
Figure 33:
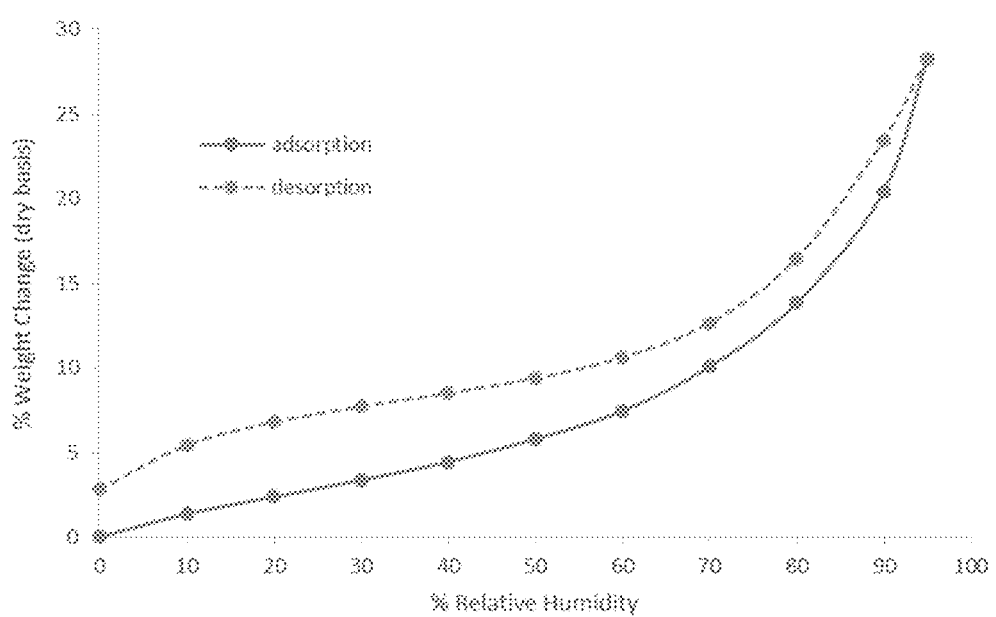
FIG. 33 is a plot of the hygroscopicity of AM(HS)1 using dynamic vapor sorption (DVS).
Figure 34:
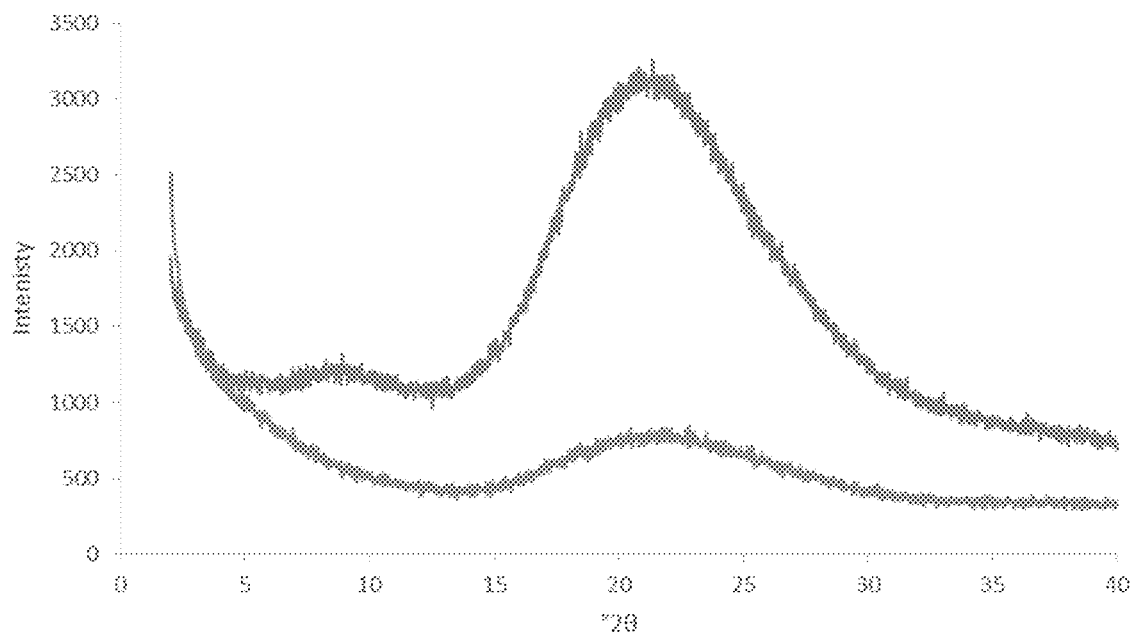
FIG. 34 illustrates an X-ray powder diffraction (XRPD) pattern of AM(HS)1 pre-DVS (top-line) and post-DVS (bottom line).
Figure 35:
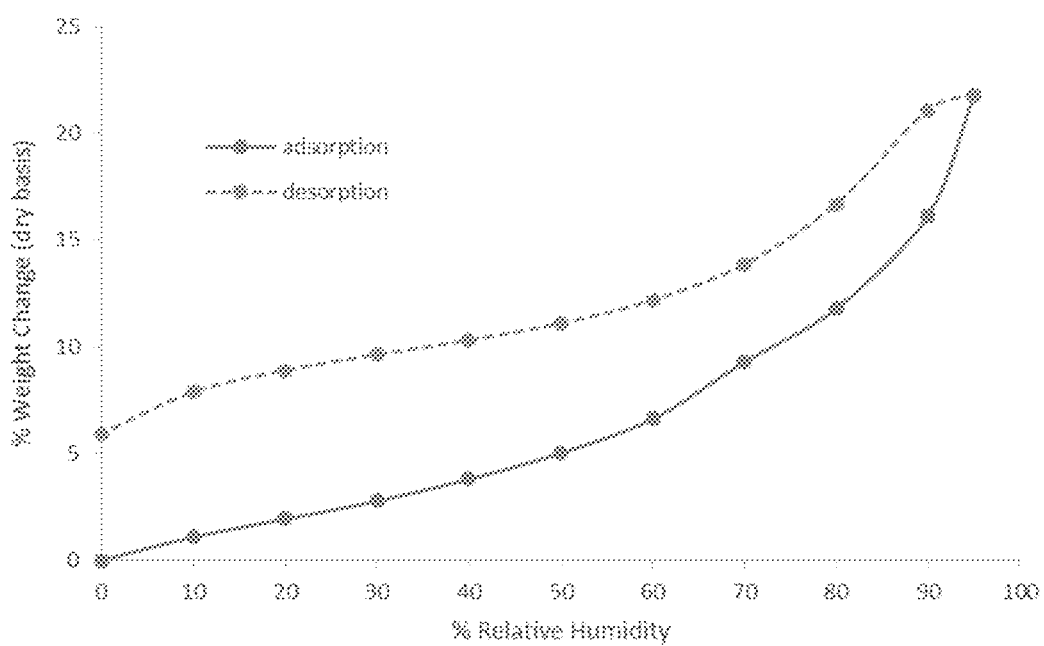
FIG. 35 is a plot of the hygroscopicity of AM(HS)2 using dynamic vapor sorption (DVS).
Figure 36:
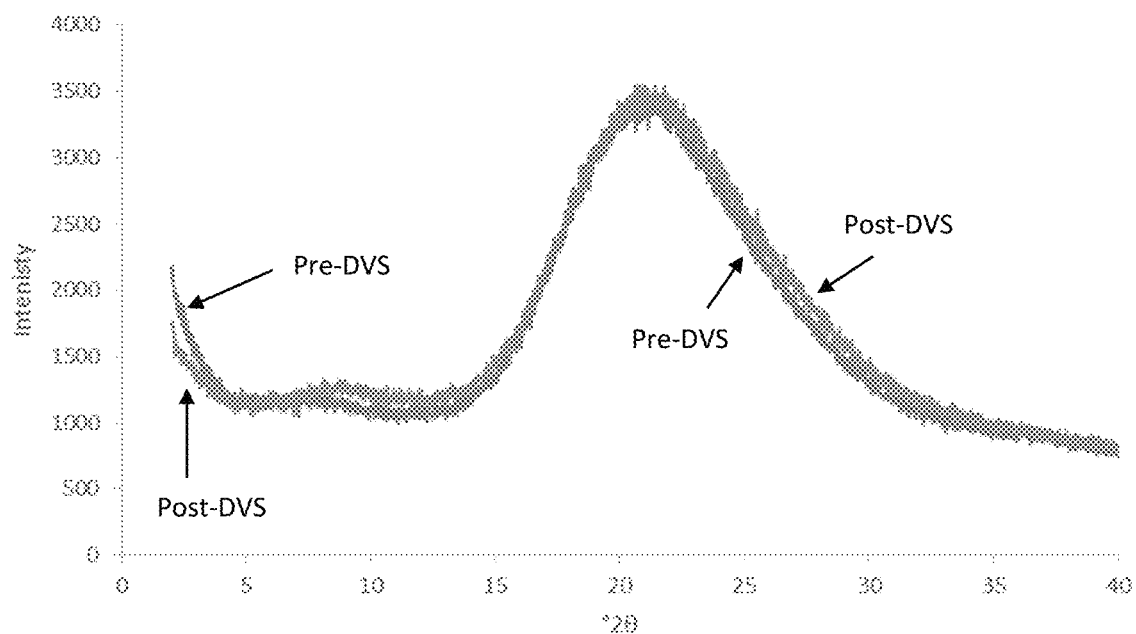
FIG. 36 illustrates an X-ray powder diffraction (XRPD) pattern of AM(HS)2 pre-DVS (top-line) and post-DVS (bottom line).
Figure 37:
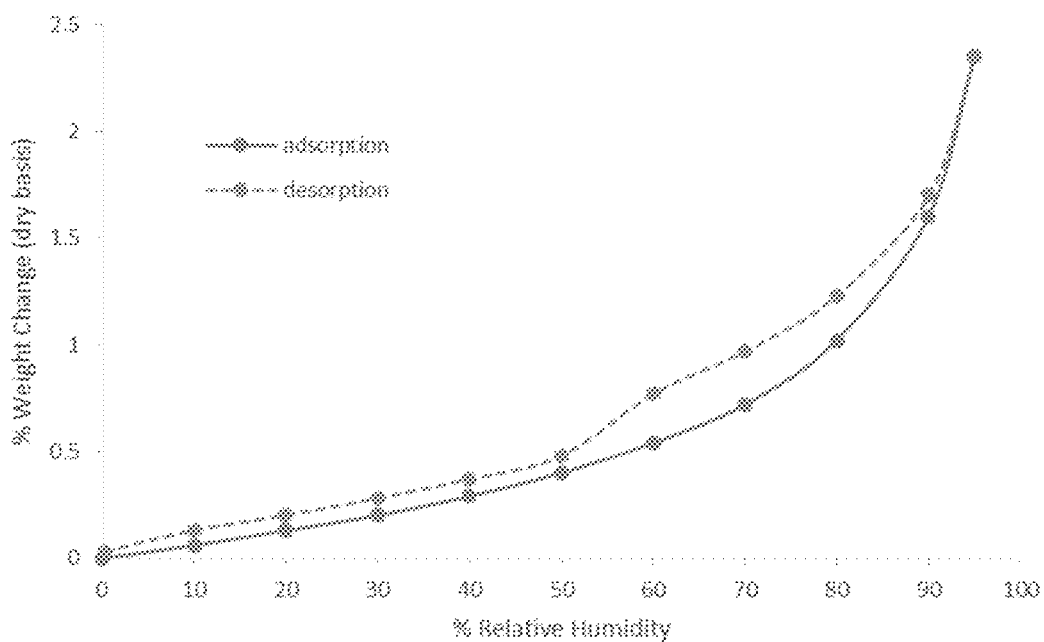
FIG. 37 is a plot of the hygroscopicity of crystalline form (I-HS) using dynamic vapor sorption (DVS).
Figure 38:
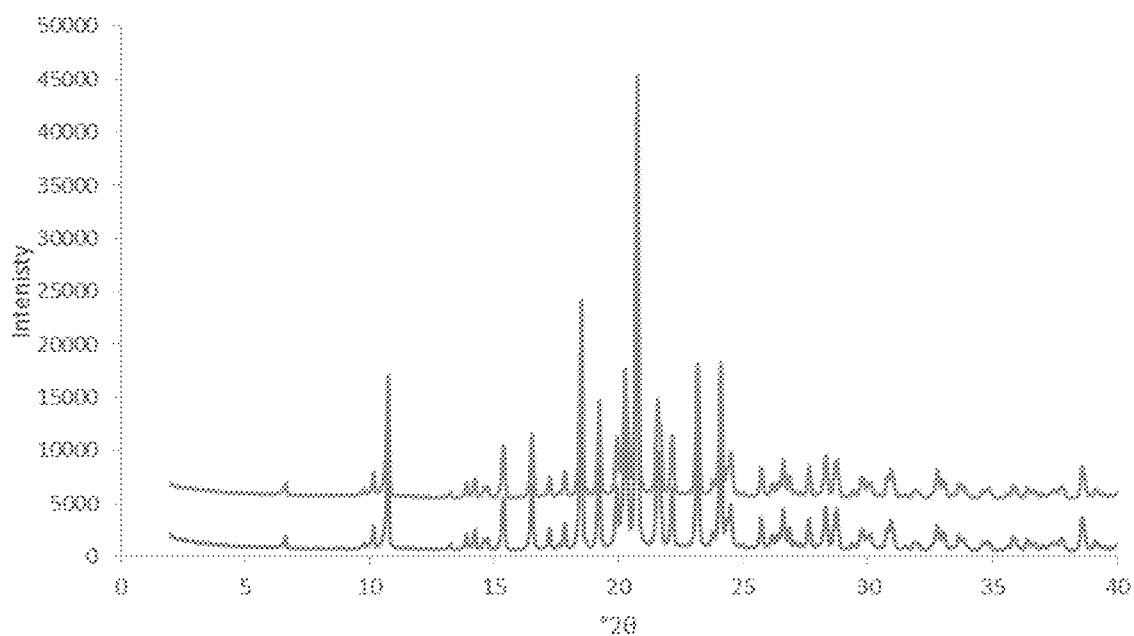
FIG. 38 illustrates an X-ray powder diffraction (XRPD) pattern of crystalline form (I-HS) pre-DVS (top-line) and post-DVS (bottom line).

In certain embodiments, crystalline form (I-HS) has an XRPD pattern that is substantially the same XRPD pattern as shown in FIG. 29.

In some embodiments, crystalline form (I-HS) has an XRPD pattern with at least the 20 characteristic peaks (2θ degrees±0.3), as listed in Table 1.

TABLE 5

XRPD peaks of crystalline form (I-HS)

| Position (°2θ) | Relative Intensity (%) |
|---|---|
| 10.76 | 29.85 |
| 15.38 | 13.22 |
| 16.52 | 16.46 |
| 18.50 | 48.07 |
| 19.22 | 22.92 |
| 19.92 | 16.05 |
| 20.26 | 30.80 |
| 20.74 | 100.00 |
| 21.56 | 23.78 |
| 22.16 | 15.51 |
| 23.16 | 32.52 |
| 24.10 | 33.89 |
| 24.50 | 12.14 |
| 25.72 | 8.89 |
| 26.50 | 10.88 |

TABLE 5-continued

XRPD peaks of crystalline form (I-HS)

| Position (°2θ) | Relative Intensity (%) |
|---|---|
| 27.62 | 8.61 |
| 28.32 | 11.44 |
| 28.74 | 10.73 |
| 30.92 | 8.23 |
| 38.60 | 8.88 |

In some embodiments, the crystalline form (I-HS) has an XRPD pattern with at least the 8 characteristic peaks (2θ degrees±0.3), which comprises peaks having a relative intensity greater than or equal to about 15%, as listed in Table 6.

TABLE 6

XRPD peaks of crystalline form (I-HS)

| Position (°2θ) | Relative Intensity (%) |
|---|---|
| 10.76 | 29.85 |
| 18.50 | 48.07 |
| 19.22 | 22.92 |
| 20.26 | 30.80 |
| 20.74 | 100.00 |
| 21.56 | 23.78 |
| 23.16 | 32.52 |
| 24.10 | 33.89 |

In some embodiments, the crystalline form (I-HS) has an XRPD pattern with at least the 5 characteristic peaks (2θ degrees±0.3), which comprises peaks having a relative intensity greater than or equal to about 25%, as listed in Table 7.

TABLE 7

XRPD peaks of crystalline form (I-HS)

| Position (°2θ) | Relative Intensity (%) |
|---|---|
| 10.76 | 29.85 |
| 18.50 | 48.07 |
| 20.74 | 100.00 |
| 23.16 | 32.52 |
| 24.10 | 33.89 |

In some embodiments, the crystalline form (I-HS) has an XRPD pattern with at least the 4 characteristic peaks (2θ degrees±0.3), which comprises peaks having a relative intensity greater than or equal to about 30%, as listed in Table 8.

TABLE 8

XRPD peaks of crystalline form (I-HS)

| Position (°2θ) | Relative Intensity (%) |
|---|---|
| 18.50 | 48.07 |
| 20.74 | 100.00 |
| 23.16 | 32.52 |
| 24.10 | 33.89 |

In some embodiments, crystalline form (I-HS) is characterized by having XRPD diffraction peaks (2θ degrees) at about 18.5, 20.7, 23.2, and 24.1. In some embodiments, crystalline form (I-HS) is characterized by having XRPD diffraction peaks (2θ degrees) at about 10.8, 18.5, 20.7, 23.2, and 24.1. In some embodiments, crystalline form (I-HS) is characterized by having XRPD diffraction peaks (2θ degrees) at about 10.8, 18.5, 19.2, 20.3, 20.7, 21.6, 23.2, and 24.1. In some embodiments, crystalline form (I-HS) is characterized by having XRPD diffraction peaks (2θ degrees) at about 10.8, 15.4, 16.5, 18.5, 19.2, 19.9, 20.3, 20.7, 21.6, 22.2, 23.2, 24.1, 24.5, 25.7, 26.5, 27.6, 28.3, 28.7, 30.9, and 38.6.

In some embodiments, given the XRPD patterns provided in FIGS. 1 and 29, crystalline form (I-HS) is characterized by having XRPD peaks (2θ degrees) as shown in Table 9.

TABLE 9

XRPD peaks of crystalline form (I-HS)

| FIG. 1 | FIG. 29 | Difference | Average |
|---|---|---|---|
| 10.76 | 10.63 | 0.13 | 10.70 |
| 15.38 | 15.25 | 0.13 | 15.32 |
| 16.52 | 16.39 | 0.13 | 16.46 |
| 18.50 | 18.37 | 0.13 | 18.44 |
| 19.22 | 19.08 | 0.14 | 19.15 |
| 19.92 | 19.79 | 0.13 | 19.86 |
| 20.26 | 20.15 | 0.11 | 20.21 |
| 20.74 | 20.61 | 0.13 | 20.68 |
| 21.56 | 21.47 | 0.09 | 21.52 |
| 22.16 | 22.01 | 0.15 | 22.09 |
| 23.16 | 23.04 | 0.12 | 23.10 |
| 24.10 | 23.97 | 0.13 | 24.04 |
| 24.50 | 24.35 | 0.15 | 24.43 |
| 25.72 | 25.58 | 0.14 | 25.65 |
| 26.50 | 26.48 | 0.02 | 26.49 |
| 27.62 | 27.50 | 0.12 | 27.56 |
| 28.32 | 28.17 | 0.15 | 28.25 |
| 28.74 | 28.58 | 0.16 | 28.66 |
| 30.92 | 30.77 | 0.15 | 30.85 |
| 38.60 | 38.47 | 0.13 | 38.54 |

In some embodiments, crystalline form (I-HS) is characterized by having XRPD diffraction peaks (2θ degrees) at 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2. In some embodiments, crystalline form (I-HS) is characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2. 24.4±0.2, 25.6±0.2, 26.5±0.2, 27.6±0.2, 28.2±0.2, 28.7±0.2, 30.8±0.2, and 38.5±0.2.

It will be understood that the 2-theta values of the X-ray powder diffraction patterns for crystalline form (I-HS) may vary slightly from one instrument to another and also depending on variations in sample preparation and batch to batch variation, and so the values quoted are not to be construed as absolute. It will also be understood that the relative intensities of peaks may vary depending on orientation effects so that the intensities shown in the XRPD trace included herein are illustrative and not intended to be used for absolute comparison. Accordingly, it is to be understood that the phrase "substantially the same XRPD pattern as shown in FIG. 1 or FIG. 29" means that for comparison purposes, at least 90% of the peaks shown in FIG. 1 or FIG. 29 are present. It is to be understood that the relative peak positions may vary ±0.3 degrees from the peak positions shown in FIG. 1 or FIG. 29. It is to be further understood that for comparison purposes some variability in peak intensities from those shown in FIG. 1 and FIG. 29 is allowed.

Figure 2:
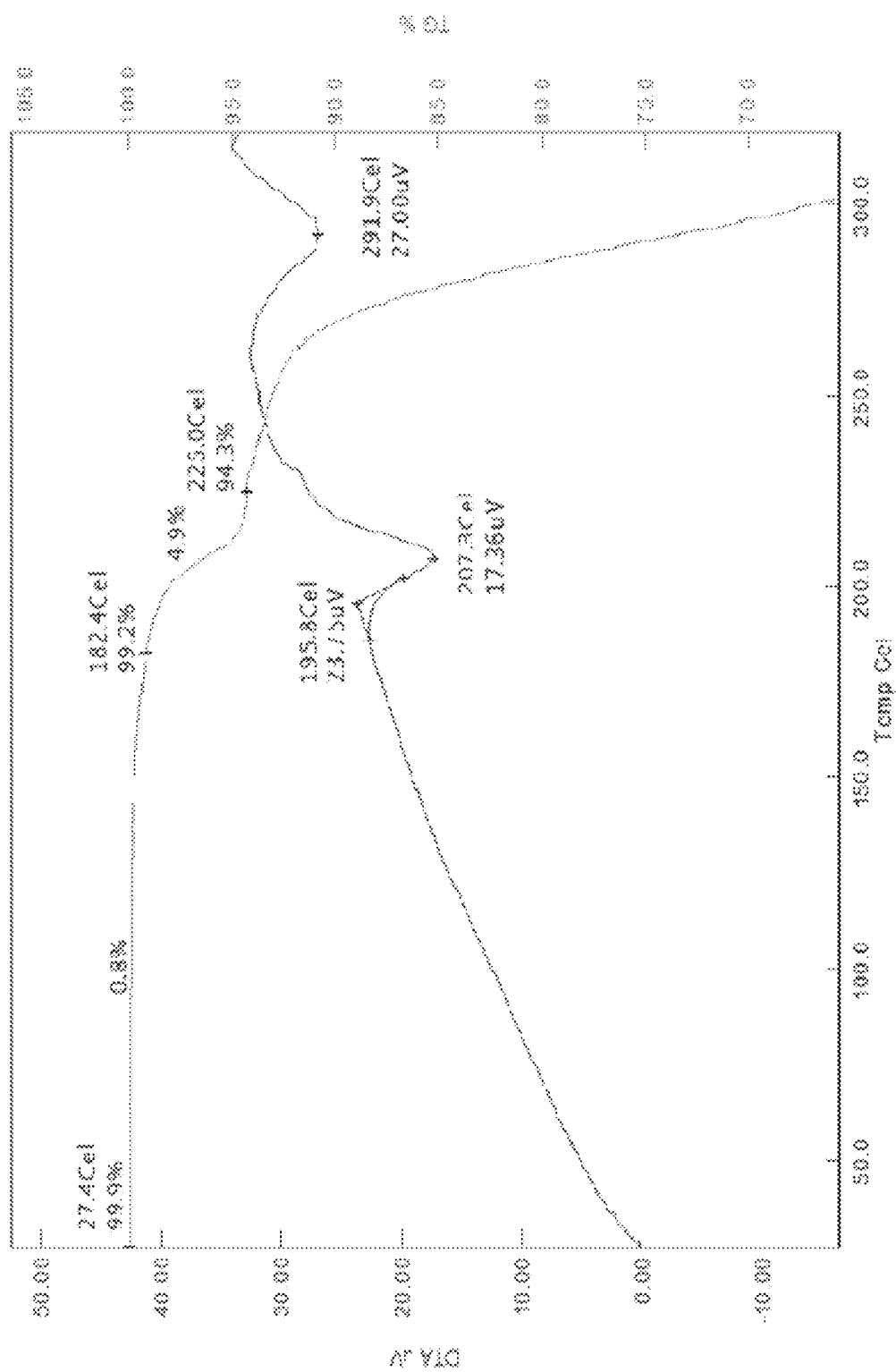
FIG. 2 illustrates a simultaneous thermogravimetric/differential thermal analyzer (TG/DTA) profile of crystalline form (I-HS) prepared according to Example 2, according to one embodiment.

FIG. 2 illustrates a simultaneous thermogravimetric/differential thermal analyzer (TG/DTA) profile of crystalline form (I-HS), according to one embodiment. For the analysis about 5 mg of crystalline form (I-HS) was weighed into an open aluminum pan and loaded into a simultaneous thermogravimetric/differential thermal analyzer (TG/DTA) and held at room temperature. The sample was then heated at a rate of 10° Celsius/min from 25° Celsius to 300° Celsius during which time the change in sample weight was recorded along with any differential thermal events. Nitrogen was used as the purge gas at a flow rate of 100 cm$^3$/min. The TG/DAT profile of crystalline form (I-HS) shows an initial weight loss of 0.8% between 27.4° Celsius to 182.4° Celsius, which is followed by 4.9% weight loss in the TG curve between 182.4° Celsius to 225.0° Celsius, also seen as an endotherm in the DTA curve. These weight losses could be decomposition of the material.

Figure 3:
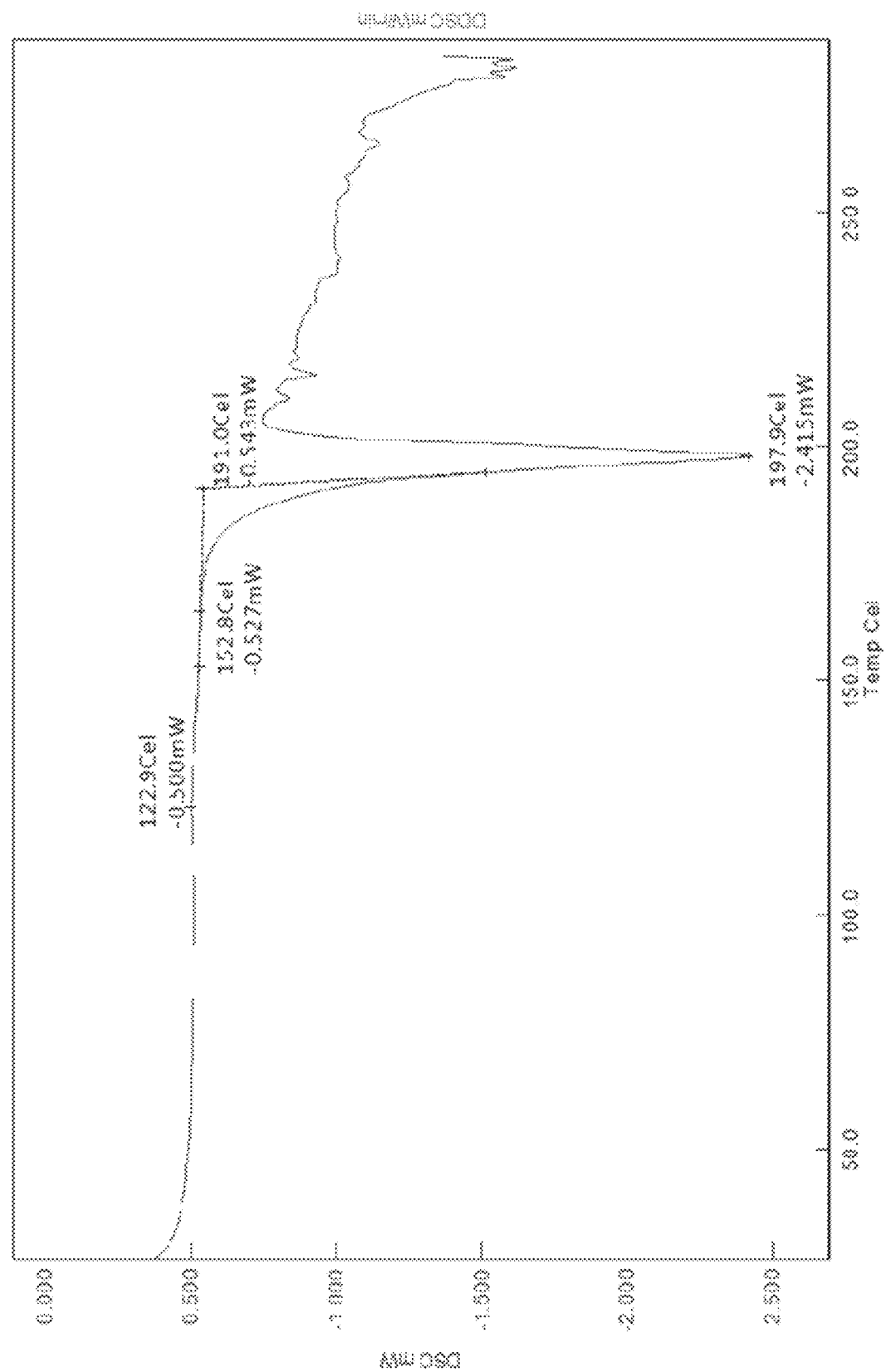
FIG. 3 illustrates a differential scanning calorimetry (DSC) profile of crystalline form (I-HS) prepared according to Example 2, according to one embodiment.

FIG. 3 illustrates a differential scanning calorimetry (DSC) profile of crystalline form (I-HS), according to one embodiment. DSC analysis of the sample was performed using a Seiko DSC6200 differential scanning calorimeter (equipped with a cooler). About 5 mg of crystalline form (I-HS) was weighed into an aluminum DSC pan and sealed non-hermetically with a pierced aluminum lid. The sample pan was then loaded into a Seiko DSC6200 (equipped with a cooler), cooled, and held at 25° Celsius. Once a stable heat-flow response was obtained, the sample and reference were heated to 270° Celsius at a scan rate of 10° Celsius/min while monitoring the resulting heat flow response. In some embodiments, crystalline form (I-HS) has a DSC thermogram substantially as shown in FIG. 3. As used herein, "substantially as shown in FIG. 3" means that the temperatures of the endothermic event shown in FIG. 3 can vary by about ±5° C.

As shown in FIG. 3, the DSC thermogram of the crystalline form (I-HS) indicates a small endothermic change in the baseline between 122.9° Celsius to 152.8° Celsius, followed by a sharp endotherm that corresponds to the melting of the crystalline form (I-HS) at an onset temperature of melting of 190.8° Celsius, a peak temperature of melting of 197.9° Celsius and a heat of melting of 2.415 mW. The transition following the melting endotherm may be caused by the decomposition of the melted crystalline form (I-HS).

Figure 4A:
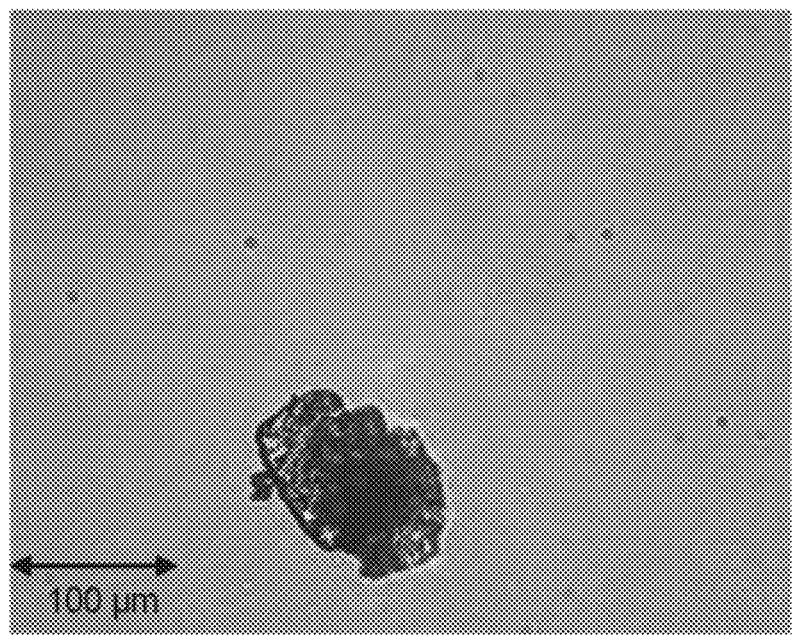
FIGS. 4A and 4B illustrate polarized light microscopy (PLM) images of crystalline form (I-HS) prepared according to Example 2 under (A) unpolarized and (B) polarized light, according to some embodiments.
Figure 4B:
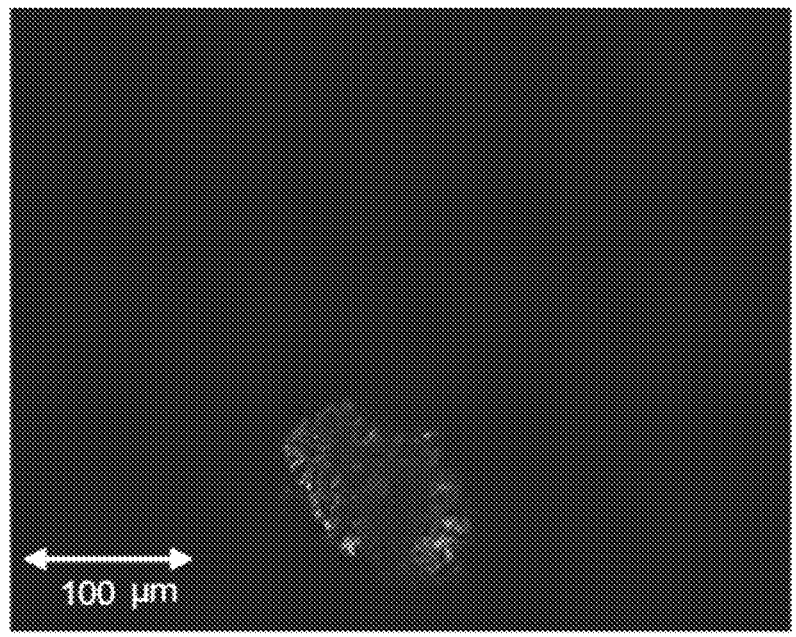

FIGS. 4A and 4B illustrate polarized light microscopy (PLM) images of crystalline form (I-HS) under (A) unpolarized and (B) unpolarized light, according to some embodiments. The presence of crystallinity (birefringence) was determined using an Olympus BX50 polarizing microscope, equipped with a Motic camera and image capture software (Motic Images Plus 2.0). All images were recorded using the 20× objective. The crystalline form (I-HS) exhibits birefringence when examined under polarized light without exhibiting a definite morphology or agglomerates.

Figure 5:
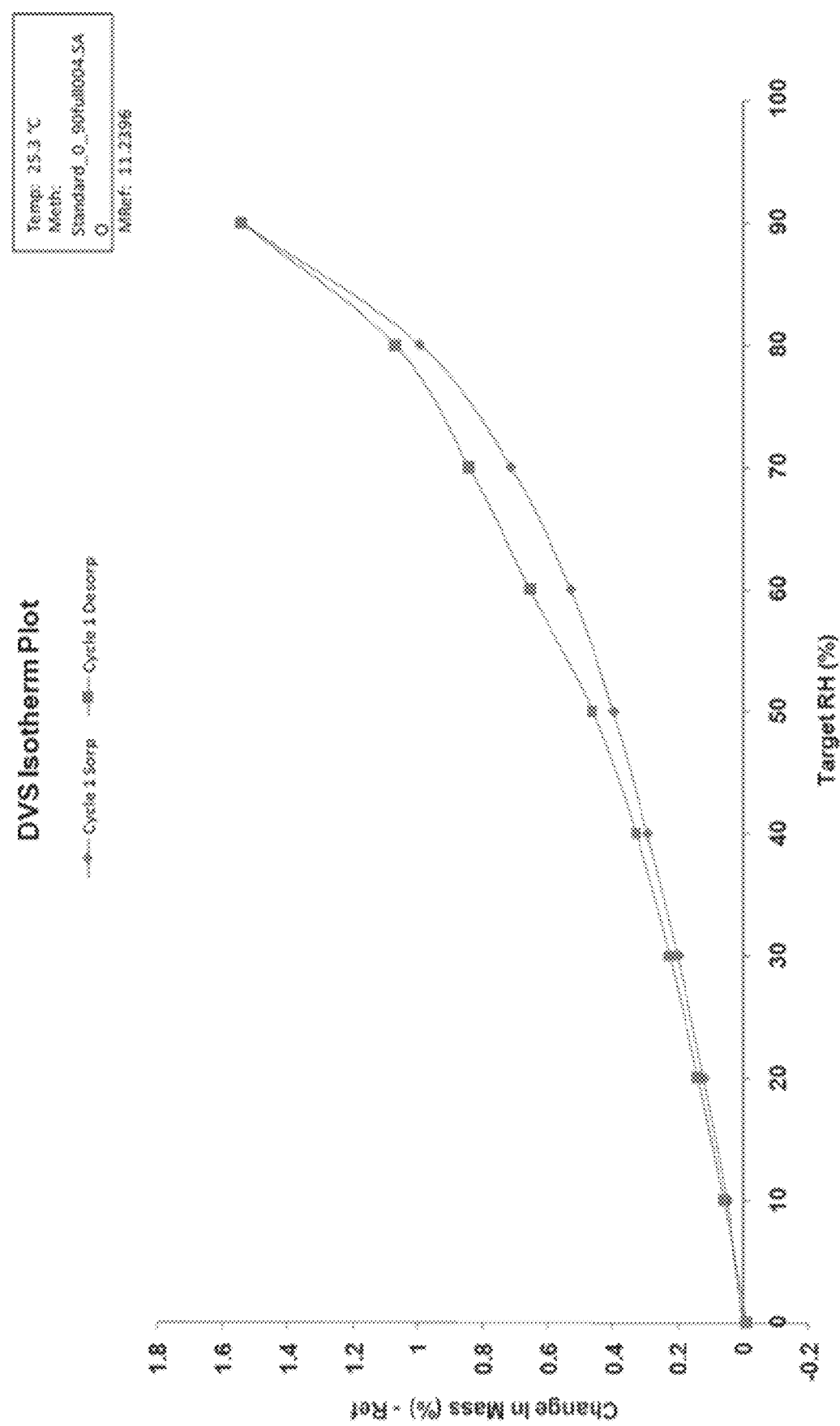
FIG. 5 illustrates a dynamic vapor sorption (DVS) isotherm profile of crystalline form (I-HS) prepared according to Example 2, according to one embodiment.

FIG. 5 illustrates a dynamic vapor sorption (DVS) isotherm profile of crystalline form (I-HS), according to one embodiment. For the DVS measurement a sample of crystalline form (I-HS) was cycled through changing humidity conditions to determine its hygroscopicity. The sample was analyzed using a Surface Measurement System DVS-1 Dynamic Vapor Sorption System. About 10 mg of crystalline form (I-HS) was placed into a mesh vapor sorption balance pan and loaded into a dynamic vapor sorption balance as part of the Surface Measurement System. Data was collected in 1 minute intervals. Nitrogen was used as the carrier gas. The sampled crystalline form (I-HS) was subjected to a ramping profile from 20-90% relative humidity (RH) at 10% increments, maintaining the sample at each step until a stable weight had been achieved (99.5% step completion). After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined.

As shown in FIG. 5, crystalline form (I-HS) appears to be non-hygroscopic. A small increase in mass of about 1.7% was observed between 0% and 90% RH during the sorption cycle. In addition, a very small hysteresis was observed between sorption and desorption cycles. The XRPD pattern of crystalline form (I-HS) post DVS analysis (not shown) being similar to its pre-DVS XRPD pattern shown in FIG. 1 or FIG. 29 indicates that no change in the crystalline form (I-HS) occurred during DVS.

Figure 6:
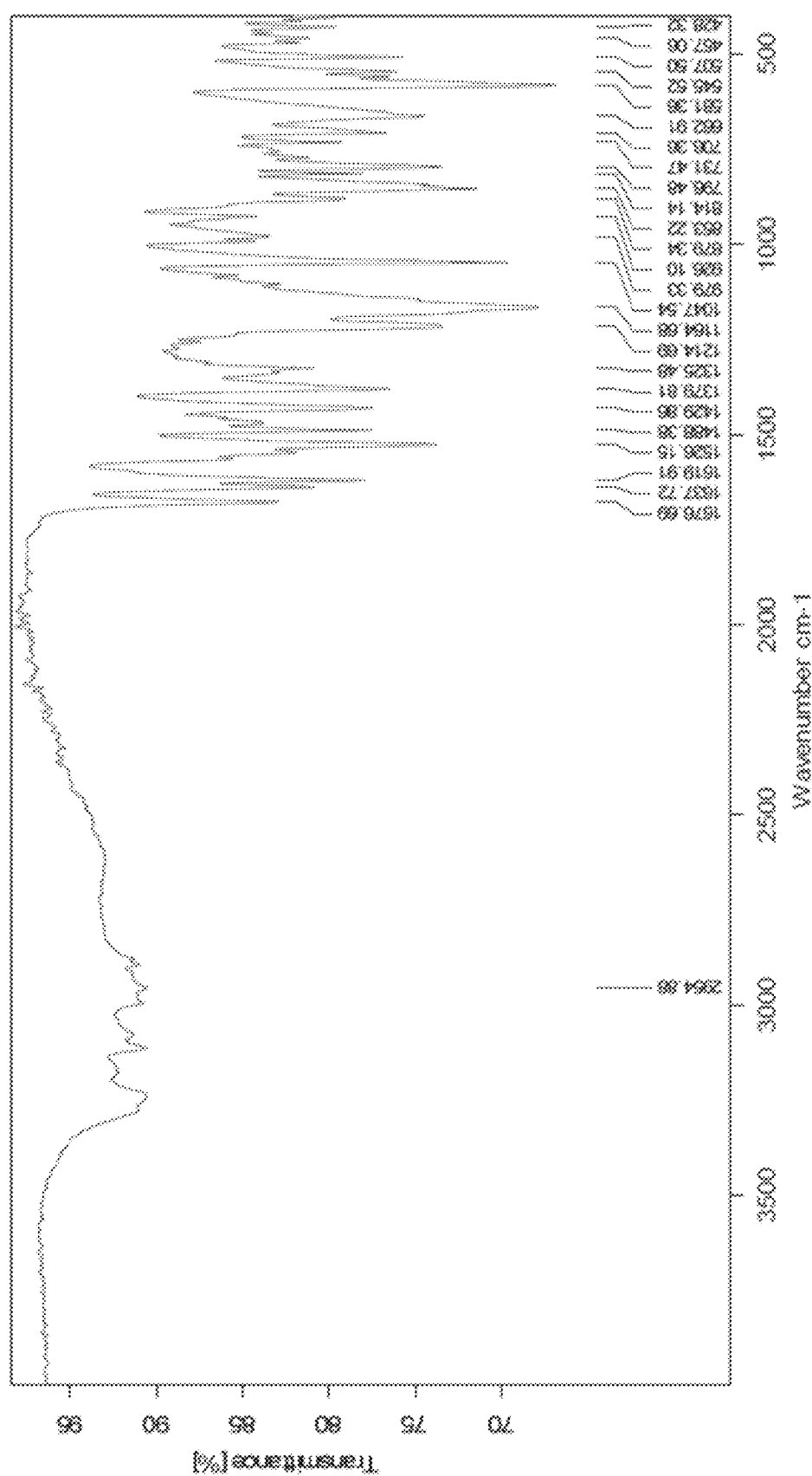
FIG. 6 illustrates an infrared (IR) spectroscopy profile of crystalline form (I-HS) prepared according to Example 2, according to one embodiment.

FIG. 6 illustrates an infrared (IR) spectroscopy profile of crystalline form (I-HS) for the compound of Formula I, according to one embodiment. IR spectroscopy was carried out on a Bruker ALPHA P spectrometer. Sufficient material of crystalline form (I-HS) was placed onto the center of the plate of the spectrometer with a transmittance spectrum being obtained using a resolution of 4 cm$^{-1}$, a background scan time of 16 scans, a sample scan time of 16 scans, and collecting data from 4000 cm$^{-1}$ to 400 cm$^{-1}$. The observed IR spectrum of crystalline form (I-HS) is shown in FIG. 6.

The crystalline form (I-HS) has a number of properties that make it surprisingly superior to the amorphous form of (S)—N-(5((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate (AM(HS)). For example, the crystalline form (I-HS) has properties which contribute to its manufacturability and production of a commercial product. As shown in Example 8, the crystalline form (I-HS) has better flow properties as compared to the amorphous API (AM(HS)) as evidenced by the Carr's and Hausner Index. For example, the crystalline form (I-HS) exhibits a Can Index value of greater than 20%. In some embodiments, the crystalline form (I-HS) exhibits a Hausner ratio of less than 1.35 (e.g., a value of between about 1.26 to about 1.34). The differences in flow properties can make the development of a solid oral dosage form more difficult for the amorphous API vs. the crystalline API.

The crystalline form (I-HS) also evidenced better stability in an accelerated stability study conducted in an LDPE bag at 40° C./75% RH for five weeks. While neither the AM(HS) or crystalline form (I-HS) exhibited a significant changes in chemical impurity levels over the course of the study, the study did reveal that the crystalline form (I-HS) has stable physicochemical properties. The amorphous API, on the other hand, converted into a crystalline form substantially similar to the crystalline form (I-HS) by XRPD, DSC, TGA, KF and polarized light microscopy. Additionally, the amorphous API changed to an agglomerated powder with reduced flow properties over the course of the stability testing. Such changes in the physical properties of the compound, including a change from an amorphous power to a crystalline material and/or an agglomerated powder with reduced flow, on storage would make it nearly impossible to manufacture a solid oral dosage form for patient use based on the amorphous compound. The properties observed for the crystalline form (I-HS), however, are consistent with that desired for a commercial product, including having both a stable physical and chemical structure.

The crystalline form (I-HS), as noted previously, is non-hygroscopic. As used herein, "non-hygroscopic" refers to a compound exhibiting less than a 2% weight gain at 25° C. and 80% RH after 24 to 48 hours (see, e.g., Example 10). The AM(HS) compound, however, was found to deliquesce upon exposure to humidity. Given this tendency, use of the AM(HS) compound would require significant handling precautions during storage and manufacture to prevent this change in form from occurring whereas the crystalline form (I-HS) requires no such precautions during manufacture of the API. This stability to humidity would also be expected to carry over to any solid oral dosage product prepared using the crystalline form (I-HS).

Finally, the crystalline form (I-HS) provides a significantly improved impurity profile versus the amorphous API. The ability to control an impurity profile is important for patient safety, developing a repeatable manufacturing process, and meeting requirements by Regulatory agencies prior to use in humans.

The compounds provided herein, including (S)—N-(5 ((R)-2-(2,5-difluorophenyl)-pyrrolidin-1-yl)-pyrazolo[1,5-a]pyrimidin-3-yl)-3-hydroxypyrrolidine-1-carboxamide (Formula I) and pharmaceutically acceptable salts thereof, for example the hydrogen sulfate salt, and further a novel crystalline form of the hydrogen sulfate salt (crystalline form (I-HS)), exhibit Trk family protein tyrosine kinase inhibition, and the compound, hydrogen sulfate salt, and crystalline form thereof can be used in the treatment of pain, inflammation, cancer, and certain infectious diseases.

Some embodiments include the use of the crystalline form (I-HS) for the treatment of disorders and diseases which can be treated by inhibiting TrkA, TrkB and/or TrkC kinases, such as a TrkA, TrkB and/or TrkC mediated condition, such as one or more conditions described herein, including a Trk-associated cancer. In some embodiments, the crystalline form (I-HS) may be also useful in the treatment of pain, including chronic and acute pain. In some embodiments, the crystalline form (I-HS) may be useful in the treatment of multiple types of pain including inflammatory pain, neuropathic pain, surgical pain, and pain associated with cancer, surgery and bone fracture. In addition, the crystalline form (I-HS) may be useful for treating inflammation, active and chronic neurodegenerative diseases and certain infectious diseases. The present disclosure is further directed to pharmaceutical compositions comprising crystalline form (I-HS). In some embodiments, the pharmaceutical composition comprises crystalline form (I-HS) and a pharmaceutically acceptable diluent or carrier.

The ability of crystalline form (I-HS) to act as TrkA, TrkB and/or TrkC inhibitors may be demonstrated by the assays described in Examples A and B as disclosed in U.S. Pat. No. 8,513,263, issued on Aug. 20, 2013, which is incorporated herein by reference.

In some embodiments, provided herein is a method for treating a patient diagnosed with a TRK-associated cancer, comprising administering to the patient a therapeutically effective amount of crystalline form (I-HS) or a compound of Formula I or a salt thereof, such as a hydrogen sulfate salt (e.g., see Example 14A of U.S. Pat. No. 8,513,263). Trk family of neurotrophin receptors, TrkA, TrkB, and TrkC (encoded by NTRK1, NTRK2, and NTRK3 genes, respectively) and their neurotrophin ligands regulate growth, differentiation and survival of neurons. Dysregulation in a NTRK gene, a Trk protein, or expression or activity, or level of the same, such as translocations involving the NTRK kinase domain, mutations involving the TRK ligand-binding site, amplifications of a NTRK gene, Trk mRNA splice variants, and Trk autocrine/paracrine signaling are described in a diverse number of tumor types and may contribute to tumorigenesis. Recently NTRK1 fusions were described in a subset of adenocarcinoma lung cancer patients[2]. Translocations in NTRK1, NTRK2, and NTRK3 that lead to the production of constitutively-active TrkA, TrkB, and TrkC fusion proteins are oncogenic and prevalent in a wide array of tumor types, including lung adenocarcinoma, thyroid, head and neck cancer, glioblastoma, and others.

In some embodiments, the dysregulation in a NTRK gene, a Trk protein, or expression or activity, or level of the same, includes overexpression of wild-type TrkA, TrkB, or TrkC (e.g., leading to autocrine activation). In some embodiments, the dysregulation in a NTRK gene, a Trk protein, or expression or activity, or level of the same, includes overexpression, activation, amplification or mutation in a chromosomal segment comprising the NTRK1, NTRK2, or NTKR3 gene or a portion thereof. In some embodiments, the dysregulation of a NTRK gene, a Trk protein, or expression or activity, or level of the same, includes one or more chromosome translocations or inversions resulting in NTRK1, NTRK2, or NTRK3 gene fusions, respectively. In some embodiments, the dysregulation of a NTRK gene, a Trk protein, or expression or activity, or level of the same, is a result of genetic translocations in which the expressed protein is a fusion protein containing residues from a non-TrkA partner protein and TrkA, a non-TrkB partner protein and TrkB, or a non-TrkC partner protein and TrkC proteins, and include a minimum of a functional TrkA, TrkB, or TrkC kinase domain, respectively.

In some embodiments, a TrkA fusion protein is one of the TrkA fusion proteins shown in Table 10, where:

TABLE 10

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| TP53-TrkA[1,11] | Tumor Protein P53 | Spitzoid Melanoma, Spitz tumors |
| LMNA-TrkA[1,12] | Lamin A/C | Spitzoid Melanoma, Spitz tumors, Undifferentiated Sarcoma, Adult Soft Tissue Sarcoma (e.g., Soft Tissue Sarcoma Metastatic to Lung), Soft Tissue Fibrosarcoma |
| CD74-TrkA[2] | MHC class II invariant chain | Non-Small Cell Lung Cancer (NSCLC) Lung adenocarcimona |

TABLE 10-continued

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| TFG-TrkA (TRK-T3)[3] | TRK-Fused Gene | Papillary Thyroid Carcinoma (PTC), Soft Tissue Solitary Fibrous Tumor |
| TPM3-TrkA[3] | Tropomyosin 3 | Lung Cancer, Papillary Thyroid Carcinoma (PTC), Acute Myeloid Leukemia (AML), Sarcoma, Pediatric Gliomas, Colorectal Cancer (CRC), Soft Tissue Schwannoma |
| NFASC-TrkA[4] | Neurofascin | Gliobastoma multiforme (GBM); Glioblastoma |
| BCAN-TrkA[4] | Brevican | Glioblastoma multiforme (GBM) |
| MPRIP-TrkA[5] | Myosin Phosphatase Rho Interacting Protein or Rho Interacting Protein 3 | Non-small cell lung cancer (NSCLC), Lung adenocarcinoma |
| TPR-TrkA (TRK-T1 or TRK-T2)[3] | Translocated Promoter Region, Nuclear Basket Protein | Papillary Thyroid Carcinoma (PTC), Colorectal Cancer (CRC)[A], Non-small cell lung cancer (NSCLC) |
| RFWD2-TrkA[6] | Ring Finger and WD Repeat Domain 2 | Large Cell Neuroendrocine Cancer (LCNEC); NSCLC |
| IRF2BP2-TrkA[7] | Interferon Regulatory Factor 2 Binding Protein 2 | Thyroid Cancer; Thyroid Gland Carcinoma |
| SQSTM1-TrkA[7] | Sequestosome 1 | Thyroid Cancer (e.g., Papillary Thyroid Cancer), Thyroid Gland Carcinoma, Soft Tissue Fibrosarcoma |
| SSBP2-TrkA[7] | Single-Stranded DNA Binding Protein 2 | Thyroid Cancer (e.g., Papillary Thyroid Cancer); Thyroid Gland Carcinoma |
| RABGAP1L-TrkA[8] | RAB GTPase Activating Protein 1-Like | Intrahepatic Cholangicarcinoma (ICC) |
| C18ORF8-TrkA[9] | Chromosome 18 Open Reading Frame 8 | Non-Small Cell Lung Cancer (NSCLC) |
| RNF213-TrkA[9] | Ring Finger Protein 213 | Non-Small Cell Lung Cancer (NSCLC) |
| TBC1D22A-TrkA[9] | TBC1 Domain Family, Member 22A | Non-Small Cell Lung Cancer (NSCLC) |
| C20ORF112-TrkA[9] | Chromosome 20 Open Reading Frame 112 | Non-Small Cell Lung Cancer (NSCLC) |
| DNER-TrkA[9] | Delta/Notch-Like EGF Repeat Containing | Non-Small Cell Lung Cancer (NSCLC) |
| ARHGEF2-TrkA[13] | Rho Guanine Nucleotide Exchange Factor 2 | Glioblastoma |
| CHTOP-TrkA[13] | Chromatin Target of PRMT1 | Glioblastoma |
| PPL-TrkA[13] | Periplakin | Thyroid Carcinoma |
| PLEKHA6-TrkA | Pleckstrin Homology Domain-Containing Family A Member 6 | |
| PEAR1-TrkA | Platelet Endothelial Aggregation Receptor 1 | |
| MRPL24-TrkA | 39S Ribosomal Protein L24, Mitochondrial | |
| MDM4-TrkA | Human Homolg of Mouse Double Minute 4 | |
| LRRC71-TrkA | Leucine Rich Repeat Containing 71 | |
| GRIPAP1-TrkA | GRIP1 Associated Protein 1 | |
| EPS15-TrkA | Epidermal Growth Factor Receptor Substrate 15 | |
| DYNC2H1-TrkA[B] | Dynein, Cytoplasmic 2, Heavy Chain 1 | Sarcoma |
| CEL-TrkA | Carboxyl Ester Lipase | Pancreatic adenocarcinoma sample[D] |
| EPHB2-TrkA[B] | EPH Receptor B2 | Lower Grade Glioma |
| TGF-TrkA[C] | Transforming Growth Factor | Papillary Thyroid Cancer |

[A]Créancier et al., *Cancer Lett.* 365(1): 107-111, 2015.
[B]U.S. Patent Application Publication No. 2015/0315657.
[C]U.S. Patent Application Publication No. 2015/0283132.
[D]Egren et al., *Cancer Res.* 75(15 Supplement): 4793, 2015.

In some embodiments, the dysregulation of a NTRK gene, a Trk protein, or expression or activity, or level of the same, includes one or more deletions, insertions, or point mutation(s) in a TrkA protein. In some embodiments, the dysregulation of a NTRK gene, a Trk protein, or expression or activity, or level of the same, includes a deletion of one or more residues from the TrkA protein, resulting in constitutive activity of the TrkA kinase domain. In some embodiments, the deletion includes a deletion of amino acids 303-377 in TrkA isoform 2.

In some embodiments, the dysregulation of a NTRK gene, a Trk protein, or expression or activity, or level of the same, includes at least one point mutation in a NTRK1 gene that results in the production of a TrkA protein that has one or more amino acid substitutions as compared to the wildtype TrkA protein (see, for example, the point mutations listed in Table 11.

TABLE 11

Activating TrkA Point Mutations

| Point Mutation | Rationale |
|---|---|
| R33W[1] | |
| A336E | Near NGF Binding Site |
| A337T | Near NGF Binding Site |
| R324Q or R324W | Near NGF Binding Site |
| V420M | Close to Membrane |
| R444Q or R444W | Close to Membrane |
| G517R or G517V | P-Loop |
| K538A | Activating |
| R649W or R649L | Arginine may stabilize auto-inhibited conformation. |
| R682S | Activation Loop |
| V683G | Activation Loop |
| R702C | Exposed, may form face-to-face disulfide linked dimer |
| C1879T[2] | |

[1]Zhang et al., Blood 124(21): 1682, 2014. Mutation found in T-cell prolymphocytic leukemia.
[2]Park et al., Proc. Natl. Acad. Sci. U.S.A. 112(40): 12492-12497, 2015. Mutation found in colorectal cancer.

In some embodiments, the dysregulation of a NTRK gene, a Trk protein, or expression or activity, or level of the same, includes a splice variation in a TrkA mRNA which results in an expressed protein that is an alternatively spliced variant of TrkA having at least one residue deleted (as compared to a wild-type TrkA protein) resulting in constitutive activity of the TrkA kinase domain. In some embodiments, an alternatively spliced form of TrkA with constitutive activity has deletions of exons 8, 9, and 11 resulting in an expressed protein missing residues 192-284 and 393-398 relative to TrkA Isoform 2, has a deletion of exon 10 in TrkA, or has a deletion in a NTRK1 gene that encodes a TrkA protein with a 75 amino acid deletion in the transmembrane domain (Reuther et al., Mol. Cell Biol. 20:8655-8666, 2000).

Cancers identified as having dysregulation of a NTRK gene, a Trk protein, or expression or activity, or level of the same, (see references cited herein and also the www.cancer.gov and www.nccn.org websites) include:

(A) Cancers wherein the dysregulation of a NTRK gene, a Trk protein, or expression or activity, or level of the same, includes one or more chromosome translocations or inversions resulting in TrkA fusion proteins, e.g., including:

| Cancer | Standard of Care |
|---|---|
| Non-Small Cell Lung Cancer[2] | radiotherapy (e.g., radioiodide therapy, external-beam radiation, or radium 223 therapy), chemotherapeutics as single agents (e.g., afatinib dimaleate, bevacizumab, carboplatin, cetuximab, cisplatin, crizotinib, erlotinib, gefitinib, gemcitabine, methotrexate, paclitaxel, or pemetrexed) or combinations (e.g., carboplatin-paclitaxel, gemcitabine-paclitaxel, or chemoradiation) |
| Papillary Thyroid Carcinoma[14] | Radiotherapies (e.g., radioiodide therapy or external-beam radiation) and chemotherapeutics (e.g., sorafenib, sunitinib, or pazopanib) |
| Glioblastoma Multiforme[15] | Chemotherapeutics (e.g., bevacizumab, everolimus, lomustine, or temozolomide) |
| Colorectal Carcinoma[16] | Chemotherapeutics as single agents (e.g., aflibercept, bevacizumab, capecitabine, cetuximab, fluorouracil, irinotecan, leucovorin, oxaliplatin, panitumumab, or regorafenib) or combinations (e.g., folfox, folfiri, capox, folfiri-bevacizumab, folfiri-cetuximab, or xelox) |
| Melanoma[12] | Chemotherapeutics (e.g., aldesleukin, dabrafenib, dacarbazine, interferon alfa-2b, ipilimumab, peginterferon alfa-2b, trametinib, or vemurafenib) |

(B) Cancers wherein the dysregulation of a NTRK gene, a Trk protein, or expression or activity, or level of the same, includes one or more deletions, insertions, or mutations in the TrkA protein, e.g., including:

| Cancer | Standard of care |
|---|---|
| Acute Myeloid leukemia[17, 18] | Chemotherapeutics as single agents (e.g., arsenic trioxide, cyclophosphamide, cytarabine, daunorubicin, doxorubicin, or vincristine) or combinations (e.g., ADE) |
| Large Cell Neuroendocrine Carcinoma[19] | Radiotherapy (e.g., radioiodide therapy, external-beam radiation, or radium 223 therapy) and/or chemotherapeutics (e.g., cisplatin, carboplatin, or etoposide) |
| Neuroblastoma[20] | Chemotherapeutics (e.g., cyclophosphamide, doxorubicin, or vincristine) |

(C) Cancers wherein the dysregulation of a NTRK gene, a Trk protein, or expression or activity, or level of the same, includes overexpression of wildtype TrkA (autocrine activation), e.g., including:

| Cancer | Standard of care |
|---|---|
| Prostate Carcinoma[21, 22] | Radiotherapy (e.g., radium 223 therapy) or chemotherapeutics (e.g. abiraterone, cabazitaxel, degarelix, denosumab, docetaxel, enzalutamide, leuprolide, prednisone, or sipuleucel-T) |
| Neuroblastoma[23] | Chemotherapeutics (e.g., cyclophosphamide, doxorubicin, or vincristine) |
| Pancreatic Carcinoma[24] | Chemotherapeutics as single agents (e.g., erlotinib, fluorouracil, gemcitabine, or mitomycin C) or combinations (e.g., gemcitabine-oxaliplatin) |
| Melanoma[25] | Chemotherapeutics (e.g., aldesleukin, dabrafenib, dacarbazine, interferon alfa-2b, ipilimumab, peginterferon alfa-2b, trametinib, or vemurafenib) |
| Head and Neck Squamous Cell Carcinoma[26] | Radiotherapy and/or chemotherapeutics (e.g., bleomycin, cetuximab, cisplatin, docetaxel, fluorouracil, or methotrexate) |
| Gastric Carcinoma[27] | Chemotherapeutics (e.g., docetaxel, doxorubucin, fluorouracil, mitomycin C, or trastuzumab) |

In some embodiments, the dysregulation of a NTRK gene, a Trk protein, or expression or activity, or level of the same, includes a translocation that results in the expression of a TrkB fusion protein, e.g., one of the TrkB fusion proteins shown in Table 12.

TABLE 12

Exemplary TrkB Fusion Proteins and Cancers

| Fusion Protein | Non-TrkB Fusion Partner | Non-limiting Exemplary Trk- and Synonyms of Associated Cancer(s) |
|---|---|---|
| NACC2-TrkB[10] | NACC Family Member 2, BEN and BTB (POZ) Domain Containing | Pilocytic Astrocytoma |
| QKI-TrkB[10] | QKI, KH Domain Containing, RNA Binding | Pilocytic Astrocytoma |
| AFAP1-TrkB[7] | Actin Filament Associated Protein 1 | Lower-grade Glioma |
| PAN3-TrkB[7] | PAN3 Poly(A) Specific Ribonuclease Subunit | Head and Neck Squamous Cell Carcinoma |
| SQSTM1-TrkB[7] | Sequestosome 1 | Lower-Grade Glioma |
| TRIM24-TrkB[7] | Tripartite Motif Containing 24 | Lung adenocarcinoma |
| VCL-TrkB[11] | Vinculin | Pediatric gliomas |
| AGBL4-TrkB[11] | ATP/GTP Binding Protein-Like 4 | Pediatric gliomas |
| DAB2IP-TrkB | Disabled Homolog 2- Interacting Protein | |

In some embodiments, the dysregulation of a NTRK gene, a Trk protein, or expression or activity, or level of the same, includes a translocation which results in the expression of a TrkC fusion protein, e.g., one of the TrkC fusion proteins shown in Table 13.

TABLE 13

Exemplary TrkC Fusion Proteins and Cancers

| Fusion Protein | Non-TrkB Fusion Partner | Non-limiting Exemplary Trk- and Synonyms of Associated Cancer(s) |
|---|---|---|
| ETV6-TrkC[11] | ETS Variant 6 | Salivary Gland Cancer, Secretory Breast Carcinoma, Acute Myeloid Leukemia, Fibrosarcoma, Nephroma, Melanoma, Colorectal Cancer (CRC), Breast Cancer, Pediatric Gliomas, Thyroid Cancer (e.g., Papillary Thyroid Cancer), Infantile Fibrosarcoma, Soft Tissue Hemangioma, Gastrointestinal Stromal Tumor (GIST) (e.g., c-kit-negative GIST), Mammary Carcinoma (e.g., Mammary Analogue Secretory Carcinoma) |
| BTBD1-TrkC[11] | BTB (POZ) Domain Containing 1 | Pediatric Gliomas |
| LYN-TrkC[7] | V-Yes-1 Yamaguchi Sarcoma Viral Related Oncogene Homolog (also known as Lck/Yes-Related Novel Protein Tyrosine Kinase) | Head and Neck Squamous Cell Carcinoma |
| RBPMS-TrkC[7] | RNA Binding Protein with Multiple Splicing | Thyroid Cancer (e.g., Papillary Thyroid Cancer) |
| EML4-TrkC[B] | Echinoderm Microtubule- Associated Protein- Like 4 | Fibrosarcoma |
| HOMER2-TrkC | Homer Protein Homolog 2 | Soft Tissue Sarcoma |
| TFG-TrkC | TRK-Fused Gene | Soft Tissue Solitary Fibrous Tumor |
| FAT1-TrkC | | Cervical Squamous Cell Carcinoma[C] |
| TEL-TrkC | | Congenital Fibrosarcoma, Acute Myelogenous Leukemia |

[B]Tannenbaum et al., *Cold Spring Harb. Mol. Case Stud.* 1: a000471, 2015.
[C]U.S. Patent Application Publication No. 2015/0315657.

In some embodiments, provided herein is a method for treating a patient diagnosed with a Trk-associated cancer, comprising administering to the patient a therapeutically effective amount of crystalline form (I-HS) or a compound of Formula I or a salt thereof, such as a hydrogen sulfate salt (e.g., see Example 14A of U.S. Pat. No. 8,513,263). For example, the Trk-associated cancer can be selected from the group of: non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma, gastric carcinoma, Spitz cancer, papillary thyroid carcinoma, colon cancer, acute myeloid leukemia, sarcoma, pediatric glioma, intrahepatic cholangicarcinoma, pilocytic astrocytoma, lower grade glioma, lung adenocarcinoma, salivary gland cancer, secretory breast cancer, fibrosarcoma, nephroma, and breast cancer.

In some embodiments, a Trk-associated cancer is selected from the group of: non-limiting examples of TRK-associated cancers include: Spitzoid melanoma, Spitz tumors (e.g., metastatic Spitz tumors), non-small cell lung cancer (NSCLC), thyroid carcinoma (e.g., papillary thyroid carcinoma (PTC)), acute myeloid leukemia (AML), sarcoma (e.g., undifferentiated sarcoma or adult soft tissue sarcoma), pediatric gliomas, colorectal cancer (CRC), gliobastoma multiforme (GBM), large cell neuroendocrine cancer (LC-NEC), thyroid cancer, intrahepatic cholangicarcinoma (ICC), pilocytic astrocytoma, lower-grade glioma, head and neck squamous cell carcinoma, adenocarcinoma (e.g., lung adenocarcinoma), salivary gland cancer, secretory breast carcinoma, breast cancer, acute myeloid leukemia, fibrosarcoma, nephroma, melanoma, bronchogenic carcinoma, B-cell cancer, Bronchus cancer, cancer of the oral cavity or pharynx, cancer of hematological tissues, cervical cancer, gastric cancer, kidney cancer, liver cancer, multiple myeloma, ovarian cancer, pancreatic cancer, salivary gland cancer, small bowel or appendix cancer, testicular cancer, urinary bladder cancer, uterine or endometrial cancer, inflammatory myofibroblastic tumors, gastrointestinal stromal tumor, non-Hodgkin's lymphoma, neuroblastoma, small cell lung cancer, squamous cell carcinoma, esophageal-gastric cancer, skin cancer, neoplasm (e.g., a melanocystic neoplasm), Spitz nevi, astrocytoma, medulloblastoma, glioma, large cell neuroendocrine tumors, bone cancer, and rectum carcinoma.

In some embodiments, the compounds provided herein are useful for treating Trk-associated cancers in pediatric patients. For example, the compounds provided herein can be used to treat infantile sarcoma, neuroblastoma, congenital mesoblastic nephroma, brain low-grade glioma, and pontine glioma.

In some embodiments, the compounds provided herein are useful for treating a Trk-associated cancer in combination with one or more additional therapeutic agents or therapies that work by the same or a different mechanism of action.

In some embodiments, the additional therapeutic agent(s) is selected from the group of: receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In some embodiments, the additional therapeutic agent(s) is selected from signal transduction pathway inhibitors, including, e.g., Ras-Raf-MEK-ERK pathway inhibitors (e.g., sorafenib, trametinib, or vemurafenib), PI3K-Akt-mTOR-S6K pathway inhibitors (e.g., everolimus, rapamycin, perifosine, or temsirolimus) and modulators of the apoptosis pathway (e.g., obataclax).

In some embodiments, the additional therapeutic agent(s) is selected from the group of: cytotoxic chemotherapeutics, including, e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In some embodiments, the additional therapeutic agent(s) is selected from the group of angiogenesis-targeted therapies, including e.g., aflibercept and bevacizumab.

In some embodiments, the additional therapeutic agent(s) is selected from the group of immune-targeted agents, e.g., including aldesleukin, ipilimumab, lambrolizumab, nivolumab, and sipuleucel-T.

In some embodiments, the additional therapeutic agent(s) is selected from agents active against the downstream Trk pathway, including, e.g., NGF-targeted biopharmaceuticals, such as NGF antibodies and panTrk inhibitors.

In some embodiments, the additional therapeutic agent or therapy is radiotherapy, including, e.g., radioiodide therapy, external-beam radiation, and radium 223 therapy.

In some embodiments, the additional therapeutic agent(s) includes any one of the above listed therapies or therapeutic agents which are standards of care in cancers wherein the cancer has a dysregulation of a NTRK gene, a Trk protein, or expression or activity, or level of the same.

Methods of detecting dysregulation of a NTRK gene, a Trk protein, or expression or activity, or level of the same, include, e.g., detection of NTRK gene translocations, e.g., using Fluorescent In Situ Hybridization (FISH) (e.g., as described in International Application Nos. PCT/US2013/061211 PCT/US2013/057495, which are incorporated herein by reference).

In some embodiments, provided herein is a method of treating cancer (e.g., a Trk-associated cancer) in a patient, comprising administering to said patient crystalline form (I-HS) or a compound of Formula I or a salt thereof, such as a hydrogen sulfate salt (e.g., see Example 14A of U.S. Pat. No. 8,513,263) in combination with at least one additional therapy or therapeutic agent. In some embodiments, the at least one additional therapy or therapeutic agent is selected from radiotherapy (e.g., radioiodide therapy, external-beam radiation, or radium 223 therapy), cytotoxic chemotherapeutics (e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, or vincristine), tyrosine kinase targeted-therapeutics (e.g., afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, or trastuzumab), apoptosis modulators and signal transduction inhibitors (e.g. everolimus, perifosine, rapamycin, sorafenib, temsirolimus, trametinib, or vemurafenib), immune-targeted therapies (e.g., aldesleukin, interferon alfa-2b, ipilimumab, lambrolizumab, nivolumab, prednisone, or sipuleucel-T) and angiogenesis-targeted therapies (e.g., aflibercept or bevacizumab), wherein the amount of a compound provided herein or a pharmaceutically acceptable salt thereof is, in combination with the additional therapy or therapeutic agent, is effective in treating said cancer.

In some embodiments, the additional therapeutic agent is a different Trk inhibitor. Non-limiting examples of other Trk inhibitors include a (R)-2-phenylpyrrolidine substituted imadazopyridazine, AZD6918, GNF-4256, GTx-186, GNF-5837, AZ623, AG-879, altiratinib, CT327, AR-772, AR-523, AR-786, AR-256, AR-618, AZ-23, AZD7451, cabozantinib, CEP-701, CEP-751, PHA-739358, dovitinib, entrectinib, PLX7486, Gö 6976, GW441756, MGCD516, ONO-5390556, PHA-848125AC, regorafenib, sorafenib, sunitinib, TSR-011, VM-902A, K252a, a 4-aminopyrazolylpyrimidine, and a substituted pyrazolo[1,5-a]pyrimidine compound.

In some embodiments, the additional therapeutic agents include: receptor tyrosine kinase-targeted therapeutic agents, such as afatinib, cabozantinib, cetuximab, crizotinib, dabrafenib, erlotinib, gefitinib, imatinib, lapatinib, lestaurtinib, nilotinib, pazopanib, panitumumab, pertuzumab, sunitinib, trastuzumab, AG 879, AZ-23, AZ623, Gö 6976, GNF-5837, GTx-186, GW 441756, MGCD516, RPI-1, RXDX101, and TSR-011; RET-targeted therapeutic agents, such as alectinib, apatinib, cabozantinib, dovitinib, lenvatinib, motesanib, nintedanib, ponatinib, regorafenib, sunitinib, sorafenib, vatalanib, vandetanib, AUY-922, BLU6864, DCC-2157, MGCD516, NVP-AST487, PZ-1, RXDX105, SPP86, TG101209, and XL-184; signal transduction pathway inhibitors, such as Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736, PLX3397, PLX7486, PLX8394, PLX9486, PRN1008, PRN1371, RXDX103, RXDX106, RXDX108, and TG101209; checkpoint inhibitors, such as ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab; modulators of the apoptosis pathway (e.g. obataclax); cytotoxic chemotherapeutics, such as arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine; angiogenesis-targeted therapies, such as aflibercept and bevacizumab; immune-targeted agents, such as aldesleukin, interferon alfa-2b, ipilimumab, lambrolizumab, nivolumab, prednisone, sipuleucel-T; radiotherapy, such as radioiodide therapy, external-beam radiation, and radium 223 therapy.

Yet other additional therapeutic agents include RET inhibitors such as those described, for example, in U.S. Pat. Nos. 8,299,057; 8,399,442; 8,937,071; 9,006,256; and 9,035,063; U.S. Publication Nos. 2014/0121239; 2011/0053934; 2011/0301157; 2010/0324065; 2009/0227556; 2009/0130229; 2009/0099167; 2005/0209195; International Publication Nos. WO 2014/184069; WO 2014/072220; WO 2012/053606; WO 2009/017838; WO 2008/031551; WO 2007/136103; WO 2007/087245; WO 2007/057399; WO 2005/051366; and WO 2005/044835; and *J. Med. Chem.* 2012, 55 (10), 4872-4876.

These additional therapeutic agents may be administered with one or more compounds provided herein as part of the same or separate dosage forms, via the same or different routes of administration, and on the same or different administration schedules according to standard pharmaceutical practice known to one skilled in the art.

Also provided herein is (i) a pharmaceutical combination for treating cancer (e.g., a Trk-associated cancer) in a patient in need thereof, which comprises (a) crystalline form (I-HS) or a compound of Formula I or a salt thereof, such as a hydrogen sulfate salt (e.g., see Example 14A of U.S. Pat. No. 8,513,263), (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer (e.g., a Trk-associated cancer); and (iv) a commercial package or product comprising such a combination as a combined preparation for simultaneous, separate or sequential use; and to a method of treatment of cancer (e.g., Trk-associated cancer) in a patient in need thereof.

Also provided are methods of treating a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art) that include administering the subject a therapeutically effective amount of crystalline form (I-HS) or a compound of Formula I or a salt thereof, such as a hydrogen sulfate salt (e.g., see Example 14A of U.S. Pat. No. 8,513,263). Also provided is crystalline form (I-HS) or a compound of Formula I or a salt thereof, such as a hydrogen sulfate salt (e.g., see Example 14A of U.S. Pat. No. 8,513,263) for use in treating a Trk-associated cancer in a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art). Also provided is the use of crystalline form (I-HS) or a compound of Formula I or a salt thereof, such as a hydrogen sulfate salt (e.g., see Example 14A of U.S. Pat. No. 8,513,263) for the manufacture of a medicament for treating a Trk-associated cancer in a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art).

Also provided are methods of treating a subject (e.g., a subject suspected of having a Trk-associated cancer, a subject presenting with one or more symptoms of a Trk-associated cancer, or a subject having an elevated risk of developing a Trk-associated cancer) that include performing an assay (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and administering (e.g., specifically or selectively administering) a therapeutically effective amount of crystalline form (I-HS) or a compound of Formula I or a salt thereof, such as a hydrogen sulfate salt (e.g., see Example 14A of U.S. Pat. No. 8,513,263) to a subject determined to have dysregulation of a NTRK gene, a Trk protein, or expression or activity, or levels of the same. Additional assays, non-limiting assays that may be used in these methods are described herein. Additional assays are also known in the art. Also provided is use of crystalline form (I-HS) or a compound of Formula I or a salt thereof, such as a hydrogen sulfate salt (e.g., see Example 14A of U.S. Pat. No. 8,513,263) for use in treating a Trk-associated cancer in a subject identified or diagnosed as having a Trk-associated cancer through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, where the presence of dysregulation of a NTRK gene, a Trk protein, or expression or activity, or level of the same, identifies that the subject has a Trk-associated cancer. Also provided is the use of crystalline form (I-HS) or a compound of Formula I or a salt thereof, such as a hydrogen sulfate salt (e.g., see Example 14A of U.S. Pat. No. 8,513, 263) for the manufacture of a medicament for treating a Trk-associated cancer in a subject identified or diagnosed as having a Trk-associated cancer through a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, where the presence of dysregulation of a NTRK gene, a Trk protein, or expression or activity, or level of the same, identifies that the subject has a Trk-associated cancer. Some embodiments of any of the methods or uses described herein further include recording in the subject's clinical record (e.g., a computer readable medium) that the subject determined to have dysregulation of a NTRK gene, a Trk protein, or expression or activity, or level of the same, through the performance of the assay, should be administered a crystalline form (I-HS) or a compound of Formula I or a salt thereof, such as a hydrogen sulfate salt (e.g., see Example 14A of U.S. Pat. No. 8,513,263).

In some embodiments of any of the methods or uses described herein, the subject has been identified or diagnosed as having a cancer with dysregulation of a NTRK gene, a Trk protein, or expression or activity, or level of the same (e.g., as determined using a regulatory agency-approved, e.g., FDA-approved, assay or kit). In some embodiments of any of the methods or uses described herein, the subject has a tumor that is positive for dysregulation of a NTRK gene, a Trk protein, or expression or activity, or level of the same (e.g., as determined using a regulatory agency-approved assay or kit). In some embodiments of any of the methods or uses described herein, the subject can be a subject with a tumor(s) that is positive for dysregulation of a NTRK gene, a Trk protein, or expression or activity, or level of the same (e.g., identified as positive using a regulatory agency-approved, e.g., FDA-approved, assay or kit). In some embodiments of any of the methods or uses described herein, the subject can be a subject whose tumors have dysregulation of a NTRK gene, a Trk protein, or expression or activity, or a level of the same (e.g., where the tumor is identified as such using a regulatory agency-approved, e.g., FDA-approved, kit or assay). In some embodiments of any of the methods or uses described herein, the subject is suspected of having a Trk-associated cancer. In some embodiments of any of the methods or uses described herein, the subject has a clinical record indicating that the subject has a tumor that has dysregulation of a NTRK gene, a Trk protein, or expression or activity, or level of the same (and optionally the clinical record indicates that the subject should be treated with any of the compositions provided herein).

Also provided are methods of treating a subject that include administering a therapeutically effective amount of crystalline form (I-HS) or a compound of Formula I or a salt thereof, such as a hydrogen sulfate salt (e.g., see Example 14A of U.S. Pat. No. 8,513,263) to a subject having a clinical record that indicates that the subject has dysregulation of a NTRK gene, a Trk protein, or expression or activity, or level of the same. Also provided is the use of crystalline form (I-HS) or a compound of Formula I or a salt thereof, such as a hydrogen sulfate salt (e.g., see Example 14A of U.S. Pat. No. 8,513,263) for the manufacture of a medicament for treating a Trk-associated cancer in a subject having a clinical record that indicates that the subject has dysregulation of a NTRK gene, a Trk protein, or expression or activity, or level of the same. Also provided is the use of crystalline form (I-HS) or a compound of Formula I or a salt thereof, such as a hydrogen sulfate salt (e.g., see Example 14A of U.S. Pat. No. 8,513,263 for the manufacture of a medicament for treating a Trk-associated cancer in a subject having a clinical record that indicates that the subject has dysregulation of a NTRK gene, a Trk protein, or expression or activity, or level of the same. Some embodiments of these methods and uses can further include: a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and recording information in a subject's clinical file (e.g., a computer-readable medium) that the subject has been identified to have dysregulation of a NTRK gene, a Trk protein, or expression or activity, or level of the same.

Also provided are methods (e.g., in vitro methods) of selecting a treatment for a subject that include selecting a treatment including administration of a therapeutically effective amount of crystalline form (I-HS) or a compound of Formula I or a salt thereof, such as a hydrogen sulfate salt (e.g., see Example 14A of U.S. Pat. No. 8,513,263) for a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art). Some embodiments can further include administering the selected treatment to the subject identified or diagnosed as having a Trk-associated cancer. Some embodiments can further include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and identifying or diagnosing a subject determined to have dysregulation of a NTRK gene, a Trk protein, or expression or activity, or level of the same, as having a Trk-associated cancer.

Also provided are methods of selecting a treatment for a subject that include administration of a therapeutically effective amount of crystalline form (I-HS) or a compound of Formula I or a salt thereof, such as a hydrogen sulfate salt (e.g., see Example 14A of U.S. Pat. No. 8,513,263), wherein the methods include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and identifying or diagnosing a subject determined to have dysregulation of a NTRK gene, a Trk protein, or expression or activity, or level of the same, as having a Trk-associated cancer, and selecting a therapeutic treatment including administration of a therapeutically effective amount of crystalline form (I-HS) or a compound of Formula I or a salt thereof, such as a hydrogen sulfate salt (e.g., see Example 14A of U.S. Pat. No. 8,513,263) for the subject identified or diagnosed as having a Trk-associated cancer. Some embodiments further include administering the selected treatment to the subject identified or diagnosed as having a Trk-associated cancer.

Also provided are methods of selecting a subject for treatment including administration of a therapeutically effective amount of crystalline form (I-HS) or a compound of Formula I or a salt thereof, such as a hydrogen sulfate salt (e.g., see Example 14A of U.S. Pat. No. 8,513,263) that include selecting, identifying, or diagnosing a subject having a Trk-associated cancer, and selecting the subject for treatment including administration of a therapeutically effective amount of crystalline form (I-HS) or a compound of Formula I or a salt thereof, such as a hydrogen sulfate salt (e.g., see Example 14A of U.S. Pat. No. 8,513,263). In some embodiments, identifying or diagnosing a subject as having a Trk-associated cancer can include a step of performing an assay (e.g., an in vitro assay) (e.g., an assay that utilizes next generation sequencing, immunohistochemistry, or break apart FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and identifying or diagnosing a subject determined to have dysregulation of a NTRK gene, a Trk protein, or expression or activity, or level of the same, as having a Trk-associated cancer. In some embodiments, the selecting a treatment can be used as part of a clinical study that includes administration of various treatments of an Alk-associated cancer.

In some embodiments of any of the methods or uses described herein, an assay used determine whether the subject has dysregulation of a NTRK gene, a Trk protein, or expression or activity, or level of the same, using a sample (e.g., a biological sample or a biopsy sample (e.g., a paraffin-embedded biopsy sample) from a subject (e.g., a subject suspected of having a Trk-associated cancer, a subject having one or more symptoms of a Trk-associated cancer, and/or a subject that has an increased risk of developing a Trk-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a NTRK gene, a Trk protein, or expression or activity, or levels of the same (see, e.g., the references cited herein).

In some embodiments, crystalline form (I-HS) or a compound of Formula I or a salt thereof, such as a hydrogen sulfate salt (e.g., see Example 14A of U.S. Pat. No. 8,513,263) is useful for treating chronic and acute pain, including pain associated with cancer, surgery, and bone fracture. Crystalline form (I-HS) or a compound of Formula I or a salt thereof, such as a hydrogen sulfate salt (e.g., see Example 14A of U.S. Pat. No. 8,513,263) may be useful in the treatment of multiple types of pain including inflammatory pain, neuropathic pain, and pain associated with cancer, surgery, and bone fracture. Crystalline form (I-HS) or a compound of Formula I or a salt thereof, such as a hydrogen sulfate salt (e.g., see Example 14A of U.S. Pat. No. 8,513,263) are also useful for treating cancers including neuroblastoma, ovarian, pancreatic and colorectal cancer. Crystalline form (I-HS) or a compound of Formula I or a salt thereof, such as a hydrogen sulfate salt (e.g., see Example 14A of U.S. Pat. No. 8,513,263) is also useful for treating inflammation and certain infectious diseases. In addition, crystalline form (I-HS) or a compound of Formula I or a salt thereof, such as a hydrogen sulfate salt (e.g., see Example 14A of U.S. Pat. No. 8,513,263) may also be used to treat interstitial cystitis (IC), painful bladder syndrome (PBS), urinary incontinence, asthma, anorexia, atopic dermatitis, and psoriasis. Crystalline form (I-HS) or a compound of Formula I or a salt thereof, such as a hydrogen sulfate salt (e.g., see Example 14A of U.S. Pat. No. 8,513,263) may also be used to treat demyelination and dysmyelination by promoting myelination, neuronal survival, and oligodendrocyte differentiation via blocking Sp35-TrkA interaction. Crystalline form (I-HS) or a compound of Formula I or a salt thereof, such as a hydrogen sulfate salt (e.g., see Example 14A of U.S. Pat. No. 8,513,263) may be useful in the treatment of multiple types of pain including inflammatory pain, neuropathic pain, surgical pain and pain associated with cancer. Crystalline form (I-HS) or a compound of Formula I or a salt thereof, such as a hydrogen sulfate salt (e.g., see Example 14A of U.S. Pat. No. 8,513,263) may be useful in the treatment of bone-related diseases (such as those involving bone resorption). Examples of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments. Other osteolytic diseases that can be treated according to the methods provided herein are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present disclosure contemplates treating. As used herein, the term treatment includes prophylaxis as well as treatment of an existing condition.

Accordingly, also provided herein is a method of treating diseases or medical conditions in a subject in need thereof, wherein said disease or condition is treatable with an inhibitor of TrkA and/or TrkB (e.g., a Trk-associated cancer), comprising administering to said subject crystalline form (I-HS) or a compound of Formula I or a salt thereof, such as a hydrogen sulfate salt (e.g., see Example 14A of U.S. Pat. No. 8,513,263 in an amount effective to treat or prevent said disorder. In a particular embodiment, provided herein is a method of treating pain, cancer, inflammation, neurodegenerative disease or *Trypanosoma cruzi* infection in a mammal, which comprises administering to said mammal a therapeutically effective amount of crystalline form (I-HS) or a compound of Formula I or a salt thereof, such as a hydrogen sulfate salt (e.g., see Example 14A of U.S. Pat. No. 8,513,263). In another embodiment, provided herein is a method of treating osteolytic disease in a mammal, which comprises administering to said subject in need thereof a therapeutically effective amount of crystalline form (I-HS) or a compound of Formula I or a salt thereof, such as a hydrogen sulfate salt (e.g., see Example 14A of U.S. Pat. No. 8,513,263).

Crystalline form (I-HS) or a compound of Formula I or a salt thereof, such as a hydrogen sulfate salt (e.g., see Example 14A of U.S. Pat. No. 8,513,263) can be used in combination with one or more additional drugs that work by the same or a different mechanism of action. Such conjoint treatment may be achieved by way of the simultaneous, sequential or separate administration of the individual components of the treatment. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

In the field of medical oncology it is normal practice to use a combination of different forms of treatment to treat each patient with cancer. In medical oncology the other component(s) of such conjoint treatment in addition to compositions provided herein may be, for example, surgery, radiotherapy, chemotherapy, signal transduction inhibitors and/or monoclonoal antibodies.

Accordingly, crystalline form (I-HS) may be administered in combination with one or more agents selected from mitotic inhibitors, alkylating agents, anti-metabolites, anti-sense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

Where the compound disclosed herein has at least one chiral center, the compounds may accordingly exist as enantiomers. Where the compounds possess two chiral centers, the compounds may additionally exist as diastereomers. That is, the compound of Formula I, in addition to having the desired configuration designated by the nomenclature "(S)—N-(5((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate" (hereinafter referred to as the (S,R) isomer), it may also be present in minor amounts as the isomer (R)—N-(5((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate (hereinafter referred to as the (R,R) isomer) and/or may also be present in minor amounts as the (S)—N-(5((S)-2-(2,5-difluorophenyl)-pyrrolidin-1-yl)-pyrazolo[1,5-a]pyrimidin-3-yl)-3-hydroxypyrrolidine-1-carboxamide hydrogen sulfate (hereinafter referred to as the (S,S) isomer), and/or may be present in minor amounts as the isomer (R)—N-(5((S)-2-(2,5-difluorophenyl)-pyrrolidin-1-yl)-pyrazolo[1,5-a]pyrimidin-3-yl)-3-hydroxypyrrolidine-1-carboxamide hydrogen sulfate" (hereinafter referred to as the (R,S) isomer). It is to be understood that all such isomers and mixtures thereof are encompassed within the scope of the present invention. Preferably, wherein the compound is present as the (S,R) isomer, the (S,R) isomer is present at an excess of greater than or equal to about 80%, more preferably at an excess of greater than or equal to about 90%, more preferably still at an excess of greater than or equal to about 95%, more preferably still at an excess of greater than or equal to about 98%, more preferably at an excess of greater than or equal to about 99%.

It will be appreciated that crystalline form (I-HS) contains two centers of asymmetry and may therefore be prepared and isolated in a mixture of isomers such as a racemic or diastereomeric mixture, or in an enantiomerically pure form. Where stereochemistry is specified by a solid wedge or dashed line representing a particular configuration, then that stereoisomer is so specified and defined.

As used herein, unless otherwise noted, the term "isolated form" shall mean that the compound is present in a form which is separate from any solid mixture with another compound(s), solvent system or biological environment. In some embodiments, the crystalline form (I-HS) is present as an isolated form.

As used herein, unless otherwise noted, the term "substantially pure form" shall mean that the mole percent of impurities in the isolated compound or crystalline form is less than about 5 mole percent, preferably less than about 2 mole percent, more preferably, less than about 0.5 mole percent, most preferably, less than about 0.1 mole percent. In some embodiments, the crystalline form (I-HS) is present as a substantially pure form.

As used herein, unless otherwise noted, the term "substantially free of other amorphous, polymorph or crystalline form(s)" when used to described crystalline form (I-HS) shall mean that mole percent of other amorphous, polymorph or crystalline form(s) of the isolated base of crystalline form (I-HS) is less than about 5 mole percent, preferably less than about 2 mole percent, more preferably, less than about 0.5 mole percent, most preferably less than about 0.1 mole percent. In some embodiments, the crystalline form (I-HS) is present as a form substantially free of other amorphous, polymorph or crystalline form(s).

The terms "polymorph" and "polymorphic form" refer to different crystalline forms of a single compound. That is, polymorphs are distinct solids sharing the same molecular formula, yet each polymorph may have distinct solid state physical properties. Therefore, a single compound may give rise to a variety of polymorphic forms where each form has different and distinct solid state physical properties, such as different solubility profiles, dissolution rates, melting point temperatures, flowability, and/or different X-ray diffraction peaks. The differences in physical properties may affect pharmaceutical parameters such as storage stability, compressibility and density (which can be important in formulation and product manufacturing), and dissolution rate (which can be an important factor in bioavailability). Techniques for characterizing polymorphic forms include, but are not limited to, X-ray powder diffractometry (XRPD), differential scanning calorimetry (DSC), thermal gravimetric analysis (TGA), single-crystal X-ray diffractometry (XRD), vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis.

The term "amorphous" means a solid in a solid state that is a non-crystalline state. Amorphous solids are disordered arrangements of molecules and therefore possess no distinguishable crystal lattice or unit cell and consequently have no definable long range ordering. The solid state form of a solid may be determined by polarized light microscopy, X-ray powder diffraction ("XRPD"), differential scanning calorimetry ("DSC"), or other standard techniques known to those of skill in the art.

As used herein, unless otherwise noted, the terms "treating," "treatment," and the like, shall include the management and care of a subject or patient (preferably mammal, more preferably human) for the purpose of combating a disease, condition, or disorder and includes the administration of a disclosed compound to alleviate the symptoms or complications, or reduce the rate of progression of the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

As used herein, the term "Trk-associated cancer" shall be defined to include cancers associated with or having dysregulation of a NTRK gene, a Trk protein, or expression or activity, or level of the same (e.g., any of types of dysregulation of a NTRK gene, a Trk protein, or expression or activity, or level of the same, described herein). Non-limiting examples of a Trk-associated cancer are described herein.

As used herein, the term "pain" shall be defined to include acute, chronic, inflammatory and neuropathic pain, including diabetic neuropathy. Further, the pain may be centrally mediated, peripherally mediated, caused by structural tissue injury, caused by soft tissue injury or caused by progressive disease. Any centrally mediated, peripherally mediated, structural tissue injury, soft tissue injury or progressive disease related pain may be acute or chronic.

As used herein, unless otherwise noted, pain shall include inflammatory pain, centrally mediated pain, peripherally mediated pain, visceral pain, structural related pain, cancer pain, soft tissue injury related pain, progressive disease related pain, neuropathic pain, acute pain from acute injury, acute pain from trauma, acute pain from surgery, headache, dental pain, back pain (preferably lower back pain), chronic pain from neuropathic conditions and chronic pain from post-stroke conditions.

Some embodiments include methods for the treatment of pain, wherein the pain is acute pain. Some embodiments include methods for the treatment of pain, wherein the pain is chronic pain. Some embodiments include methods for the treatment of pain, wherein the pain is neuropathic pain, including diabetic neuropathy. Some embodiments include methods for the treatment of pain, wherein the pain is inflammatory pain.

In some embodiments, the pain is selected from the group consisting of osteoarthritis, rheumatoid arthritis, fibromyalgia, headache, toothache, burn, sunburn, animal bite (such as dog bite, cat bite, snake bite, spider bite, insect sting, and the like), neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, labor, childbirth, menstrual cramps, cancer, back pain, lower back pain and carpal tunnel syndrome pain.

Acute pain includes pain caused by acute injury, trauma, illness or surgery (for example, open-chest surgery (including open-heart or bypass surgery)). Acute pain also includes, and is not limited to, headache, post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

Chronic pain includes pain caused by an inflammatory condition, osteoarthritis, rheumatoid arthritis or as sequela to disease, acute injury or trauma. Chronic pain also includes, and is not limited to, headache, upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

Neuropathic pain includes pain resulting from chronic or debilitating conditions or disorders. The chronic or debilitating conditions or disorders which can lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathic dystrophy, phantom limb syndrome and other chronic and debilitating condition-associated pain syndromes.

"Acute neurodegenerative disorders or diseases" include, but are not limited to, various types of acute neurodegenerative disorders associated with neuron death or damage including cerebrovascular insufficiency, focal brain trauma, diffuse brain damage, and spinal cord injury, that is, cerebral ischemia or infarction including embolic occlusion and thrombotic occlusion, reperfusion following acute ischemia, perinatal hypoxic-ischemic injury, cardiac arrest, as well as intracranial hemorrhage of any type (including, but not limited to, epidural, subdural, subarachnoid and intracerebral), and intracranial and intravertebral lesions (including, but not limited to, contusion, penetration, shear, compression and laceration), and whiplash shaken infant syndrome. In some embodiments, the acute neurodegenerative disorder is a result of stroke, acute ischemic injury, head injury or spinal injury.

"Chronic neurodegenerative disorders or diseases" include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), multiple sclerosis, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia). In some embodiments, the chronic neurodegenerative disorder is selected from Alzheimer's disease, Parkinson's disease, multiple sclerosis or cerebral palsy.

The term "subject" as used herein, refers to an animal, preferably a mammal, most preferably a human, who has been the object of treatment, observation or experiment. In some embodiments, the subject has experienced and/or exhibited at least one symptom of the disease or disorder to be treated and/or prevented. In some embodiments, a patient is a pediatric patient (i.e. a patient under the age of 21 years at the time of diagnosis or treatment). The term "pediatric" can be further divided into various subpopulations including: neonates (from birth through the first 28 days of life); infants (29 days of age to less than two years of age); children (two years of age to less than 12 years of age); and adolescents (12 years of age through 21 years of age (up to, but not including, the twenty-second birthday)).

In some embodiments, the subject has been identified or diagnosed as having a cancer with dysregulation of a NTRK gene, a Trk protein, or expression or activity, or level of the same (e.g., as determined using a regulatory agency-approved, e.g., FDA-approved, assay or kit). In some embodiments, the subject has a tumor that is positive for dysregulation of a NTRK gene, a Trk protein, or expression or activity, or level of the same (e.g., as determined using a regulatory agency-approved assay or kit). The subject can be a subject with a tumor(s) that is positive for dysregulation of a NTRK gene, a Trk protein, or expression or activity, or level of the same (e.g., identified as positive using a regulatory agency-approved, e.g., FDA-approved, assay or kit). The subject can be a subject whose tumors have dysregulation of a NTRK gene, a Trk protein, or expression or activity, or a level of the same (e.g., where the tumor is identified as such using a regulatory agency-approved, e.g., FDA-approved, kit or assay). In some embodiments, the subject is suspected of having a Trk-associated cancer. In some embodiments, the subject has a clinical record indicating that the subject has a tumor that has dysregulation of a NTRK gene, a Trk protein, or expression or activity, or level of the same (and optionally the clinical record indicates that the subject should be treated with any of the compositions provided herein).

The term "Trk" or "Trk protein" includes any of the Trk proteins described herein (e.g., a TrkA, a TrkB, or a TrkC protein).

The term "NTRK gene" includes any of the NTRK genes described herein (e.g., a NTRK1, a NTRK2, or a NTRK3 gene).

The term "wildtype" or "wild-type" describes a nucleic acid (e.g., a NTRK gene or a Trk mRNA) or protein (e.g., a Trk protein) that is found in a subject that does not have a Trk-associated cancer (and optionally also does not have an increased risk of developing a Trk-associated cancer or condition and/or is not suspected of having a Trk-associated cancer or condition) or is found in a cell or tissue from a subject that does not have a Trk-associated cancer or condition (and optionally also does not have an increased risk of developing a Trk-associated cancer or condition and/or is not suspected of having a Trk-associated cancer or condition).

The term "regulatory agency" is a country's agency for the approval of the medical use of pharmaceutical agents with the country. For example, a non-limiting example of a regulatory agency is the U.S. Food and Drug Administration (FDA).

The phrase "dysregulation of a NTRK gene, a Trk protein, or expression or activity, or level of the same" is a genetic mutation (e.g., a NTRK gene translocation that results in the expression of a fusion protein, a deletion in a NTRK gene that results in the expression of a Trk protein that includes a deletion of at least one amino acid as compared to the wild-type Trk protein, or a mutation in a NTRK gene that results in the expression of a Trk protein with one or more point mutations, an alternative spliced version of a Trk mRNA that results in a Trk protein that results in the deletion of at least one amino acid in the Trk protein as compared to the wild-type Trk protein), or a NTRK gene duplication that results in overexpression of a Trk protein) or an autocrine activity resulting from the overexpression of a NTRK gene a cell, that results in a pathogenic increase in the activity of a kinase domain of a Trk protein (e.g., a constitutively active kinase domain of a Trk protein) in a cell. For example, a dysregulation of a NTRK gene, a Trk protein, or expression or activity, or level of the same, can be a mutation in a NTRK1, NTRK2, or NTRK3 gene that encodes a Trk protein that is constitutively active or has increased activity as compared to a protein encoded by a NTRK1, NTRK2, or NTRK3 gene that does not include the mutation. For example, a dysregulation of a NTRK gene, a Trk protein, or expression or activity, or level of the same, can be the result of a gene translocation which results in the expression of a fusion protein that contains a first portion of TrkA, TrkB, or TrkC that includes a functional kinase domain, and a second portion of a partner protein (i.e., that is not TrkA, TrkB, or TrkC). A gene encoding a fusion protein can include, e.g., the following exons of a wild-type NTRK1 gene: exons 10-19, exons 12-19, exons 12-19, exons 13-19, exons 14-19, or exons 15-19. A gene encoding a fusion protein can include, e.g., the following exons of a wild-type NTRK2 gene: exons 12-21, exons 13-21, exons 15-21, exons 16-21, or exons 17-21. A gene encoding a fusion protein can include, e.g., the following exons of a wild-type NTRK3 gene: exons 17-22 or exons 16-22. Non-limiting examples of fusion proteins that are a result of a NTRK gene translocation are described in Tables 1, 3, and 4.

A dysregulation of a NTRK gene, a Trk protein, or expression or activity, or level of the same, can, e.g., include a mutation(s) in a NTRK1, NTRK2, or NTRK3 gene that results in a TrkA, TrkB, or TrkC containing at least one (e.g., two, three, four, or five) point mutations (e.g., one of more of the point mutations listed in Table 6). A dysregulation of a NTRK gene, a Trk protein, or expression or activity, or level of the same, can, e.g., include a mutation in a NTRK2 gene that results in a TrkB protein including a point mutation of V673M. A dysregulation of a NTRK gene, a Trk protein, or expression or activity, or level of the same, can, e.g., include a mutation in a NTRK3 gene that results in a TrkC protein including a point mutation of H677Y.

A dysregulation of a NTRK gene, a Trk protein, or expression or activity, or level of the same, can be a mutation in a NTRK1, NTRK2, or NTRK3 gene that results in a deletion of one or more contiguous amino acids (e.g., at least two, at least three, at least four, at least 5, at least 6, at least 7, at least 8, at least 9, at least 10, at least 15, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, or at least 400 amino acids) in the TrkA, TrkB, or TrkC protein (except for the deletion of amino acids in the kinase domain of TrkA, TrkB, or TrkC that would result in inactivation of the kinase domain). In some embodiments, dysregulation of a NTRK gene, a Trk protein, or expression or activity, or level of the same, can include a deletion in a NTRK1 gene that results in a TrkA protein that lacks the NGF-binding site or exon 10, which includes the NGF binding site, the latter of which is associated with acute myeloid leukemia.

In some examples, a dysregulation of a NTRK gene, a Trk protein, or expression or activity, or level of the same, can include an alternate spliced form of a Trk mRNA, e.g., a TrkAIII spliced variant or an alternative spliced form of a TrkA mRNA that results in the production of a TrkA protein that lacks the amino acids encoded by exon 10. In some examples, a dysregulation of a NTRK gene, a Trk protein, or expression or activity, or level of the same, includes an amplification of a NTRK gene (e.g., one, two, three, or four additional copies of the NTRK gene) that can result, e.g., in an autocrine expression of a NTRK gene in a cell.

The term "Trk-associated cancer or tumor" is a cancer that is associated with dysregulation of a NTRK gene, a Trk protein, or expression or activity, or level of the same (e.g., a cancer that is associated with at least one example (e.g., two, three, four, or five examples) of dysregulation of a NTRK gene, a Trk protein, or expression or activity, or level of the same, described herein).

The term "mammal" as used herein, refers to a warm-blooded animal that has or is at risk of developing a disease described herein and includes, but is not limited to, guinea pigs, dogs, cats, rats, mice, hamsters, and primates, including humans.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In particular, a therapeutically effective amount, when administered to a subject in need of such treatment, is sufficient to (i) treat or prevent a particular disease, condition, or disorder which can be treated with an inhibitor of TrkA and/or TrkB, (ii) attenuate, ameliorate, or eliminate one or more symptoms of the particular disease, condition, or disorder, or (iii) prevent or delay the onset of one or more symptoms of the particular disease, condition, or disorder described herein. The amount of crystalline form (I-HS) that will correspond to such a therapeutically effective amount will vary depending upon factors such the disease condition and its severity, the identity (e.g., weight) of the mammal in need of treatment, but can nevertheless be routinely determined by one skilled in the art.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In some embodiments, the term "about" is used herein to mean approximately, in the region of, roughly, or around. When the term "about" is used in conjunction with a numerical range, it modifies that range by extending the boundaries above and below the numerical values set forth.

In general, the term "about" is used herein to modify a numerical value above and below the stated value by a variance of 10%.

The term "about" preceding one or more peak positions in an X-ray powder diffraction pattern means that all of the peaks of the group which it precedes are reported in terms of angular positions (two theta) with an allowable variability of ±0.3°. The variability of ±0.3° is intended to be used when comparing two powder X-ray diffraction patterns. In practice, if a diffraction pattern peak from one pattern is assigned a range of angular positions (two theta) which is the measured peak position ±0.3° and if those ranges of peak positions overlap, then the two peaks are considered to have the same angular position. For example, if a peak from one pattern is determined to have a position of 11.0°, for comparison purposes the allowable variability allows the peak to be assigned a position in the range of 10.7°-11.3°.

The term "about" preceding a value for DSC, TGA, TG, or DTA, which are reported as degrees Celsius, have an allowable variability of ±5° C.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Further provided herein are pharmaceutical compositions containing crystalline form (I-HS) with a pharmaceutically acceptable carrier. Pharmaceutical compositions containing crystalline form (I-HS) as the active ingredient can be prepared by intimately mixing crystalline form (I-HS) with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

Crystalline form (I-HS) may be administered by any convenient route, e.g. into the gastrointestinal tract (e.g. rectally or orally), the nose, lungs, musculature or vasculature, or transdermally or dermally. Crystalline form (I-HS) may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Also provided herein are pharmaceutical compositions comprising crystalline form (I-HS). To prepare the pharmaceutical compositions provided herein, crystalline form (I-HS) as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, glycerols, oils, cyclodextrins, alcohols, e.g., ethanol, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutical compositions herein will contain, per unit dosage unit, e.g., tablet, capsule, suspension, solution, sachet for reconstitution, powder, injection, I.V., suppository, sublingual/buccal film, teaspoonful and the like, of from about 0.1-1000 mg or any range therein, and may be given at a dosage of from about 0.01-300 mg/kg/day, or any range therein, preferably from about 0.5-50 mg/kg/day, or any range therein. In some embodiments, the pharmaceutical compositions provided herein contain, per unit dosage unit, about 25 mg to about 500 mg of a compound provided herein (for example, about 25 mg to about 400 mg, about 25 mg to about 300 mg, about 25 mg to about 250 mg, about 25 mg to about 200 mg, about 25 mg to about 150 mg, about 25 mg to about 100 mg, about 25 mg to about 75 mg, about 50 mg to about 500 mg, about 100 mg to about 500 mg, about 150 mg to about 500 mg, about 200 mg to about 500 mg, about 250 mg to about 500 mg, about 300 mg to about 500 mg, about 400 mg to about 500 mg, about 50 to about 200 mg, about 100 to about 250 mg, about 50 to about 150 mg). In some embodiments, the pharmaceutical compositions provided herein contain, per unit dosage unit, about 25 mg, about 50 mg, about 100 mg, about 150 mg, about 200 mg, about 250 mg, about 300 mg, about 400 mg, or about 500 mg of a compound provided herein. The dosages, however, may be varied depending upon the requirement of the patients, the severity of the condition being treated and the compound being employed. In some embodiments, the dosages are administered once daily (QD) or twice daily (BID).

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, crystalline form (I-HS) is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of crystalline form (I-HS). When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, or any amount or range thereof, of the active ingredient provided herein. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions provided herein may be incorporated for administration orally or by injection include, aqueous solutions, cyclodextrins, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. For parenteral administration, sterile suspensions and solutions are desired. Isotonic preparations which generally contain suitable preservatives are employed when intravenous administration is desired.

Crystalline form (I-HS) can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

To prepare a pharmaceutical compositions provided herein, crystalline form (I-HS) as the active ingredient is intimately admixed with a pharmaceutical carrier according to conventional pharmaceutical compounding techniques, which carrier may take a wide variety of forms depending of the form of preparation desired for administration e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds provided herein may be administered in any of the foregoing compositions and according to dosage regimens established in the art whenever treatment of cancer, pain, inflammation, neurodegenerative disease or *Trypanosoma cruzi* infection s required.

The daily dosage of crystalline form (I-HS) may be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range may be from about 0.1 to about 50.0 mg/kg of body weight per day, or any amount or range therein. In another example, the range may be from about 0.1 to about 15.0 mg/kg of body weight per day, or any range therein. In yet another example, the range may be from about 0.5 to about 7.5 mg/kg of body weight per day, or any amount to range therein. Crystalline form (I-HS) may be administered on a regimen of 1 to 4 times per day or in a single daily dose.

Optimal dosages to be administered may be readily determined by those skilled in the art, and will vary with the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Acronyms found in the specification have the following meanings:

| ATP | adenosine triphosphate |
|---|---|
| DI | deionized |
| EtOH | ethanol |

-continued

| GC | gas chromatography |
|---|---|
| MOPS | 3-(N-morpholino)-propanesulfonic acid |
| MTBE | methyl tert-butyl ether |
| PDA | photodiode array |
| RRT | relative retention time |
| RT | room temperature |
| THF | tetrahydrofuran |
| TMB | 3,3',5,5'-tetramethylbenzidine |

The following examples illustrate the invention and are set forth to aid in the understanding of the invention, and are not intended and should not be construed to limit in any way the invention set forth in the claims which follow thereafter.

In the examples described below, unless otherwise indicated all temperatures are set forth in degrees Celsius. Reagents were purchased from commercial suppliers such as Sigma-Aldrich Chemical Company, EMD, JT Baker, or Pharco-Aaper, and were used without further purification unless otherwise indicated. Tetrahydrofuran (THF), heptane and other organic solvents were purchased from commercial suppliers, such as Sigma-Aldrich Chemical Company, ACROS, Alfa-Aesar, Lancaster, TCI, or Maybridge, and used as received.

One skilled in the art will recognize that, where not otherwise specified, the reaction step(s) is performed under suitable conditions, according to known methods, to provide the desired product. One skilled in the art will also recognize that wherein a reaction step as disclosed herein may be carried out in a variety of solvents or solvent systems, said reaction step may also be carried out in a mixture of the suitable solvents or solvent systems. One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

The reactions set forth below were done generally under a positive pressure of nitrogen (unless otherwise stated) in "ACS grade" solvents, and the reaction flasks were typically fitted with rubber septa for the introduction of substrates and reagents via syringe or addition funnel.

Two reversed-phase high performance liquid chromatography (HPLC) systems were used for in-process monitoring and analysis, using acetonitrile and water/trifluoroacetic acid as mobile phases. One system employed an Agilent Zorbax Extend C18 column at 264 nm, while the other system (hereinafter, "TRK1PM1 HPLC") included a Waters Xbridge Phenyl Column at 268 nm. Unless otherwise specified, the former system was used. The silica for both systems was stirred in a flask with the compound, and then filtered through a polypropylene cloth before being analyzed.

Figure 7:
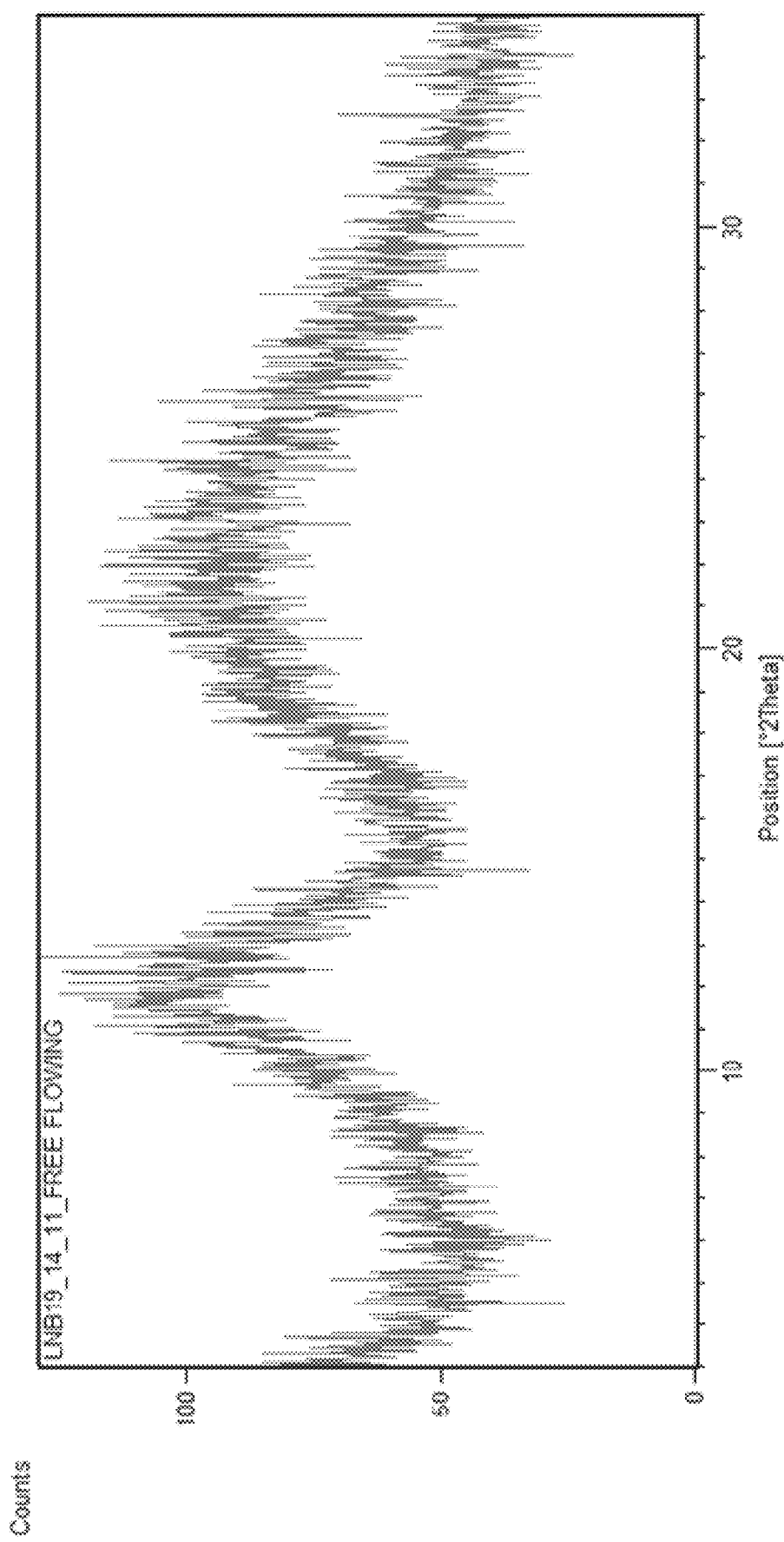
FIG. 7 illustrates an XRPD pattern of the amorphous freebase form of a compound of Formula I, according to one embodiment.

Amorphous freebase form of compound of Formula I: About 1 gram of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide is dissolved in minimum amount of water and cooled to a temperature of about −26° Celsius followed by drying in the freeze dryer for 24 hours. About 20 mg of the amorphous material obtained from the freeze dryer was weighed in a vial, to which 5 volume aliquots of an appropriate solvent system was added. The mixture was checked for dissolution and if no dissolution was apparent, the mixture was heated to about 40° Celsius and checked again. This procedure was continued until dissolution was observed or until 100 volumes of solvent had been added. The XRPD pattern of the amorphous material obtained from the freeze drying experiment is shown in FIG. 7.

Figure 28:
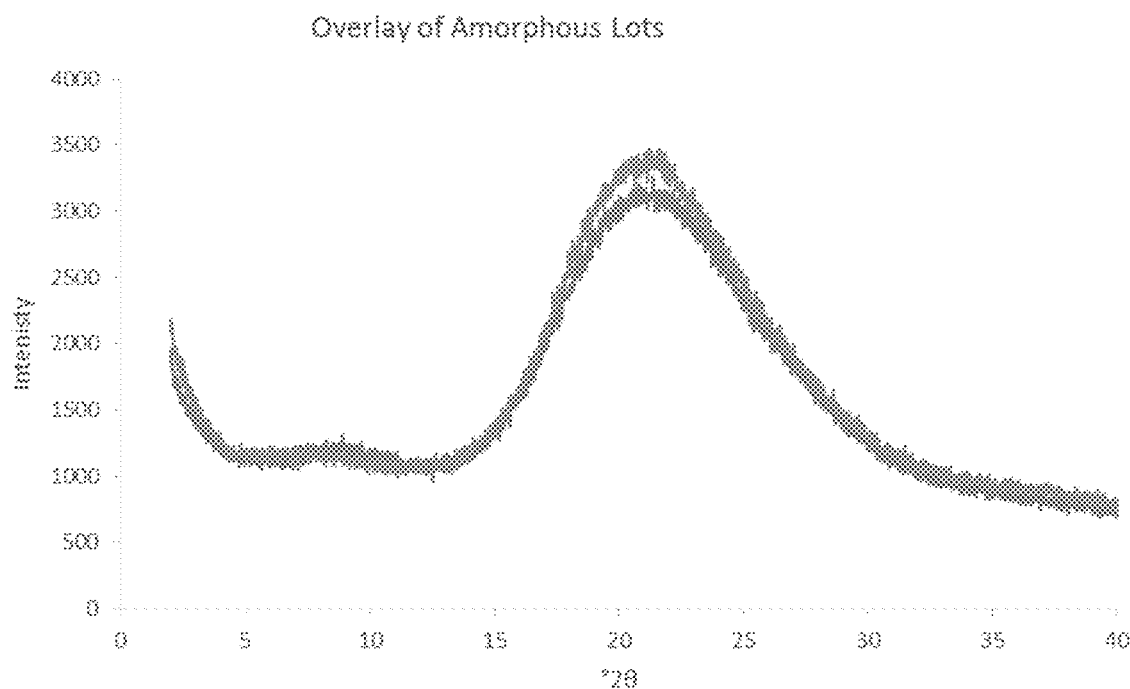
FIG. 28 illustrates an X-ray powder diffraction (XRPD) pattern of AM(HS)1 and AM(HS)2.

Amorphous hydrogen sulfate salt of compound of Formula I was prepared as described in Example 14A in WO 2010/048314 (see Example 3). The XRPD patterns of the two different lots of amorphous material prepared by this method are show in FIG. 28.

Also provided herein is a process for the preparation of crystalline form (I-HS). In some embodiments, the process comprises the steps as shown in Scheme 1.

In some embodiments, provided herein is a process for the preparation of crystalline form (I-HS), comprising:

(a) adding concentrated sulfuric acid to a solution of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide in EtOH to form the hydrogen sulfate salt of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide;

(b) adding heptane to the solution in Step (a) to form a slurry;

(c) filtering the slurry to isolate (S)—N-(5((R)-2-(2,5-difluorophenyl)pyrrolidin-1-yl)-pyrazolo[1,5-a]pyrimidin-3-yl)-3-hydroxypyrrolidine-1-carboxamide hydrogen sulfate;

(d) mixing said (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate with a 5:95 w/w solution of water/2-butanone;

(e) heating the mixture from step (d) at about 65-70° C. with stirring until the weight percent of ethanol is about 0.5% to form a slurry of the crystalline form of (S)—N-(5-((R-2-(2,5-difluorophenyl)pyrrolidin-1-yl)-pyrazolo[1,5-a]pyrimidin-3-yl)-3-hydroxypyrrolidine-1-carboxamide hydrogen sulfate; and (f) isolating the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate by filtration.

In some embodiments, the above method further comprises: (b1) seeding the solution from step (a) with (S)—N-(5((R)-2-(2,5-difluorophenyl)pyrrolidin-1-yl)-pyrazolo[1,5-a]pyrimidin-3-yl)-3-hydroxypyrrolidine-1-carboxamide hydrogen sulfate at room temperature and allowing the solution to stir until a slurry forms.

In some embodiments, provided herein is a process for the preparation of crystalline form (I-HS), comprising:

(a) reacting 5-chloro-3-nitropyrazolo[1,5-a]pyrimidine with (R)-2-(2,5-difluorophenyl)-pyrrolidin (R)2-hydroxysuccinate in the presence of a base to form (R)-5-(2-(2,5-difluorophenyl)pyrrolidin-1-yl)-3-nitropyrazolo[1,5-a]pyrimidine;

(b) treating said (R)-5-(2-(2,5-difluorophenyl)pyrrolidin-1-yl)-3-nitropyrazolo[1,5-a]pyrimidine with Zn and hydrochloric acid to form (R)-5-(2-(2,5-difluorophenyl)pyrrolidin-1-yl)pyrazolo[1,5-a]pyrimidin-3-amine;

(c) treating said (R)-5-(2-(2,5-difluorophenyl)pyrrolidin-1-yl)pyrazolo[1,5-a]pyrimidin-3-amine with a base and phenyl chloroformate to form phenyl (R)-(5-(2-(2,5-difluorophenyl)pyrrolidin-1-yl)pyrazolo[1,5-a]pyrimidin-3-yl)carbamate;

(d) reacting said phenyl (R)-(5-(2-(2,5-difluorophenyl)pyrrolidin-1-yl)pyrazolo[1,5-a]pyrimidin-3-yl)carbamate with (S)-pyrrolidin-3-ol to form (S)—N-(5-((R)-2-(2,5-difluorophenyl)pyrrolidin-1-yl)pyrazolo[1,5-a]pyrimidin-3-yl)-3-hydroxypyrrolidine-1-boxamide;

(e) adding sulfuric acid to said (S)—N-(5-((R)-2-(2,5-difluorophenyl)pyrrolidin-1-yl)pyrazolo[1,5-a]pyrimidin-3-yl)-3-hydroxypyrrolidine-1-carboxamide form (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate; and (f) isolating the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate.

In some embodiments of the above step (a), the base is an amine base, such as triethylamine.

In some embodiments of the above step (c), the base is an alkali metal base, such as an alkali metal carbonate, such as potassium carbonate.

Preparation A

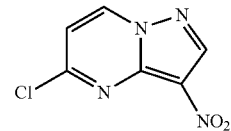 [SMILES: O=[N+]([O-])c1cnn2ccc(Cl)nc12]

Preparation of 5-chloro-3-nitropyrazolo[1,5-a]pyrimidine

Step A—Preparation of sodium pyrazolo[1,5-a]pyrimidin-5-olate

A solution of 1H-pyrazol-5-amine and 1,3-dimethylpyrimidine-2,4(1H,3H)-dione (1.05 equiv.) were charged to a round bottom flask outfitted with a mechanical stirrer, a steam pot, a reflux condenser, a J-Kem temperature probe and an $N_2$ adaptor for positive $N_2$ pressure control. Under mechanical stirring the solids were suspended with 4 vol. (4 mL/g) of absolute EtOH under a nitrogen atmosphere, then charged with 2.1 equivalents of NaOEt (21 wt % solution in EtOH), and followed by line-rinse with 1 vol. (1 mL/g) of absolute EtOH. The slurry was warmed to about 75° Celsius and stirred at gentle reflux until less than 1.5 area % of 1H-pyrazol-5-amine was observed by TRK1PM1 HPLC to follow the progression of the reaction using 20 μL of slurry diluted in 4 mL deionized water and 5 μL injection at 220 nm.

After 1 additional hour, the mixture was charged with 2.5 vol. (2.5 mL/g) of heptane and then refluxed at 70° Celsius for 1 hour. The slurry was then cooled to room temperature overnight. The solid was collected by filtration on a tabletop funnel and polypropylene filter cloth. The reactor was rinsed and charged atop the filter cake with 4 vol. (4 mL/g) of heptane with the cake pulled and the solids being transferred to tared drying trays and oven-dried at 45° Celsius under high vacuum until their weight was constant. Pale yellow solid sodium pyrazolo[1,5-a]-pyrimidin-5-olate was obtained in 93-96% yield (corrected) and larger than 99.5 area % observed by HPLC (1 mg/mL dilution in deionized water, TRK1PM1 at 220 nm).

Step B—Preparation of 3-nitropyrazolo[1,5-a]pyrimidin-5(4H)-one

A tared round bottom flask was charged with sodium pyrazolo[1,5-a]pyrimidin-5-olate that was dissolved at 40-45° Celsius in 3.0 vol. (3.0 mL/g) of deionized water, and then concentrated under high vacuum at 65° Celsius in a water-bath on a rotary evaporator until 2.4× weight of starting material was observed (1.4 vol/1.4 mL/g deionized water content). Gas chromatography (GC) for residual EtOH (30 μL of solution dissolved in ~1 mL MeOH) was performed showing less than 100 ppm with traces of ethyl nitrate fumes being observed below upon later addition of HNO$_3$. In some cases, the original solution was charged with an additional 1.5 vol. (1.5 mL/g) of DI water, then concentrated under high vacuum at 65° Celsius in a water-bath on a rotary evaporator until 2.4× weight of starting material was observed (1.4 vol/1.4 mL/g DI water content). Gas chromatograph for residual EtOH (30 μL of solution dissolved in about 1 mL MeOH) was performed showing <<100 ppm of residual EtOH without observing any ethyl nitrate fumes below upon later addition of HNO$_3$.

A round bottom vessel outfitted with a mechanical stirrer, a steam pot, a reflux condenser, a J-Kem temperature probe and an N$_2$ adaptor for positive N$_2$ pressure control was charged with 3 vol. (3 mL/g, 10 equiv) of >90 wt % HNO$_3$ and cooled to about 10° Celsius under a nitrogen atmosphere using external ice-water cooling bath under a nitrogen atmosphere. Using a pressure equalizing addition funnel, the HNO$_3$ solution was charged with the 1.75-1.95 volumes of a deionized water solution of sodium pyrazolo[1,5-a]pyrimidin-5-olate (1.16-1.4 mL DI water/g of sodium pyrazolo[1,5-a]pyrimidin-5-olate) at a rate to maintain 35-40° Celsius internal temperature under cooling. Two azeotropes were observed without any ethyl nitrate fumes. The azeotrope flask, the transfer line (if applicable) and the addition funnel were rinsed with 2×0.1 vol. (2×0.1 mL/g) deionized water added to the reaction mixture. Once the addition was complete, the temperature was gradually increased to about 45-50° Celsius for about 3 hours with HPLC showing >99.5 area % conversion of sodium pyrazolo[1,5-a]pyrimidin-5-olate to 3-nitropyrazolo[1,5-a]pyrimidin-5(4H)-one.

Step C—Preparation of 5-chloro-3-nitropyrazolo[1,5-a]pyrimidine 3-nitropyrazolo[1,5-a]pyrimidin-5(4H)-one was charged to a round bottom flask outfitted with a mechanical stirrer, a heating mantle, a reflux condenser, a J-Kem temperature probe and an N$_2$ adaptor for positive N$_2$ pressure control. Under mechanical stirring the solids were suspended with 8 volumes (8 mL/g) of CH$_3$CN, and then charged with 2,6-lutitine (1.05 equiv) followed by warming the slurry to about 50° Celsius. Using a pressure equalizing addition funnel, the mixture was dropwise charged with 0.33 equivalents of POCl. This charge yielded a thick, beige slurry of a trimer that was homogenized while stirring until a semi-mobile mass was observed. An additional 1.67 equivalents of POCl was charged to the mixture while allowing the temperature to stabilize, followed by warming the reaction mixture to a gentle reflux (78° Celsius). Some puffing was observed upon warming the mixture that later subsided as the thick slurry got thinner.

The reaction mixture was allowed to reflux until complete dissolution to a dark solution and until HPLC (20 μL diluted in 5 mL of CH$_3$CN, TRK1PM1 HPLC, 5 μL injection, 268 nm) confirmed that no more trimer (RRT 0.92) was present with less than 0.5 area % of 3-nitropyrazolo[1,5-a]pyrimidin-5(4H)-one (RRT 0.79) being observed by manually removing any interfering and early eluting peaks related to lutidine from the area integration. On a 1.9 kg scale, 0 area % of the trimer, 0.25 area % of 3-nitropyrazolo[1,5-a]pyrimidin-5(4H)-one, and 99.5 area % of 5-chloro-3-nitropyrazolo[1,5-a]pyrimidine was observed after 19 hours of gentle reflux using TRK1PM1 HPLC at 268 nm Preparation B

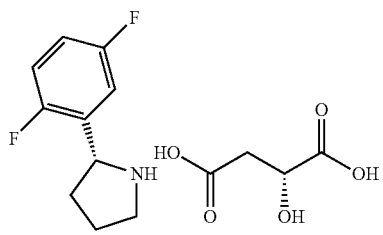

Preparation of (R)-2-(2,5-difluorophenyl)-pyrrolidine (R)-2-hydroxysuccinate

Step A—Preparation of tert-butyl (4-(2,5-difluorophenyl)-4-oxobutyl)-carbamate 2-bromo-1,4-difluorobenzene (1.5 eq.) was dissolved in 4 volumes of THF (based on weight of tert-butyl 2-oxopyrrolidine-1-carboxylate) and cooled to about 5° Celsius. A solution of 2.0 M iPrMgCl in THF (1.4 eq.) was added over 2 hours to the mixture while maintaining a reaction temperature below 25° Celsius. The solution was allowed to cool to about 5° Celsius and stirred for 1 hour (GC analysis confirmed Grignard formation). A solution of tert-butyl 2-oxopyrrolidine-1-carboxylate (1.0 eq.) in 1 volume of THF was added over about 30 min while maintaining a reaction temperature below 25° Celsius. The reaction was stirred at about 5° Celsius for 90 min (tert-butyl 2-oxopyrrolidine-1-carboxylate was confirmed to be less than 0.5 area % by HPLC). The reaction was quenched with 5 volumes of 2 M aqueous HCl while maintaining a reaction temperature below 45° Celsius. The reaction was then transferred to a reparatory funnel adding 10 volumes of heptane and removing the aqueous layer. The organic layer was washed with 4 volumes of saturated aqueous NaCl followed by addition of 2×1 volume of saturated aqueous NaCl. The organic layer was solvent-switched to heptane (<1% wt THF confirmed by GC) at a distillation temperature of 35-55° Celsius and distillation pressure of 100-200 mm Hg for 2×4 volumes of heptane being added with a minimum distillation volume of about 7 volumes. The mixture was then diluted to 10 volumes with heptane while heating to about 55° Celsius yielded a denser solid with the mixture being allowed to cool to room temperature overnight. The slurry was cooled to less than 5° Celsius and filtered through polypropylene filter cloth. The wet cake was washed with 2×2 volumes of heptane. The solids were dried under vacuum at 55° Celsius until the weight was constant, yielding tert-butyl (4-(2,5-difluorophenyl)-4-oxobutyl)-carbamate as a white solid at about 75% to 85% theoretical yield.

Step B—Preparation of 5-(2,5-difluorophenyl)-3,4-dihydro-2H-pyrrole tert-butyl (4-(2,5-difluorophenyl)-4-oxobutyl)-carbamate was dissolved in 5 vol. of toluene with 2.2 eq. of 12M HCl being added observing a mild exotherm and gas evolution. The reaction was heated to 65° Celsius for 12-24 hours and monitored by HPLC. Upon completion the reaction was cooled to less than 15° Celsius with an ice/water bath. The pH was adjusted to about 14 with 3 equivalents of 2M aqueous NaOH (4.7 vol.). The reaction was stirred at room temperature for 1-2 hours. The mixture was transferred to a separatory funnel with toluene. The aqueous layer was removed and the organic layer was washed with 3 volumes of saturated aqueous NaCl. The organic layer was concentrated to an oil and redissolved in 1.5 volumes of heptane. The resulting suspension was filtered through a GF/F filter paper and concentrated to a light yellow oil of 5-(2,5-difluorophenyl)-3,4-dihydro-2H-pyrrole with a 90% to 100% theoretical yield.

Step C—Preparation of (R)-2-(2,5-difluorophenyl)-pyrrolidine

Chloro-1,5-cyclooctadiene iridium dimer (0.2 mol %) and (R)-2-(2-(diphenylphosphino)phenyl)-4-isopropyl-4,5-dihydrooxazole (0.4 mol %) were suspended in 5 volumes of MTBE (based on 5-(2,5-difluorophenyl)-3,4-dihydro-2H-pyrrole) at room temperature. The mixture was stirred for 1 hour and most of the solids dissolved with the solution turning dark red. The catalyst formation was monitored using an HPLC/PDA detector. The reaction was cooled to less than 5° Celsius and 5-(2,5-difluorophenyl)-3,4-dihydro-2H-pyrrole (1.0 eq.) was added using a 0.5 volumes of MTBE rinse. Diphenylsilane (1.5 eq.) was added over about 20 minutes while maintaining a reaction temperature below 10° Celsius. The reaction was stirred for 30 minutes below 10° Celsius and then allowed to warm to room temperature. The reaction was stirred overnight at room temperature. The completion of the reaction was confirmed by HPLC and then cooled to less than 5° Celsius. The reaction was quenched with 5 volumes of 2M aqueous HCl maintaining temperature below 20° Celsius. After 10 minutes the ice/water bath was removed and the reaction temperature was allowed to increase to room temperature while stirring for 2 hours. The mixture was transferred to a separatory funnel with 3 volumes of MTBE. The aqueous layer was washed with 3.5 volumes of MTBE followed by addition of 5 volumes of MTBE to the aqueous layer while adjusting the pH to about 14 by adding 0.75 volumes of aqueous 50% NaOH. The organic layer was washed with 5 volumes of aqueous saturated NaCl, then concentrated to an oil, and diluted with 3 volumes of MTBE. The solution was filtered through a polypropylene filter cloth and rinsed with 1 volume of MTBE. The filtrate was concentrated to an oil of (R)-2-(2,5-difluorophenyl)-pyrrolidine with a 95% to 100% theoretical yield and with 75-85% ee.

Step D—Preparation of (R)-2-(2,5-difluorophenyl)-pyrrolidine (R)-2-hydroxy-succinate (R)-2-(2,5-difluorophenyl)-pyrrolidine (1.0 eq.) was transferred to a round bottom flask charged with 15 volumes (corrected for potency) of EtOH (200 prf). D-malic acid (1.05 eq.) was added and the mixture was heated to 65° Celsius. The solids all dissolved at about 64° Celsius. The solution was allowed to cool to RT. At about 55° Celsius the solution was seeded with (R)-2-(2,5-difluorophenyl)-pyrrolidine (R)-2-hydroxy-succinate (about 50 mg, >97% ee) and stirred at room temperature overnight. The suspension was then filtered through a polypropylene filter cloth and washed with 2×1 volumes of EtOH (200 prf). The solids were dried under vacuum at 55° Celsius, yielding (R)-2-(2,5-difluorophenyl)-pyrrolidine (R)-2-hydroxy-succinate with a 75% to 90% theoretical yield and with >96% ee.

Referring to Scheme 1, suitable bases include tertiary amine bases, such as triethylamine, and K₂CO₃. Suitable solvents include ethanol, heptane and tetrahydrofuran (THF). The reaction is conveniently performed at temperatures between 5° Celsius and 50° Celsius. The reaction progress was generally monitored by HPLC TRK1PM1.

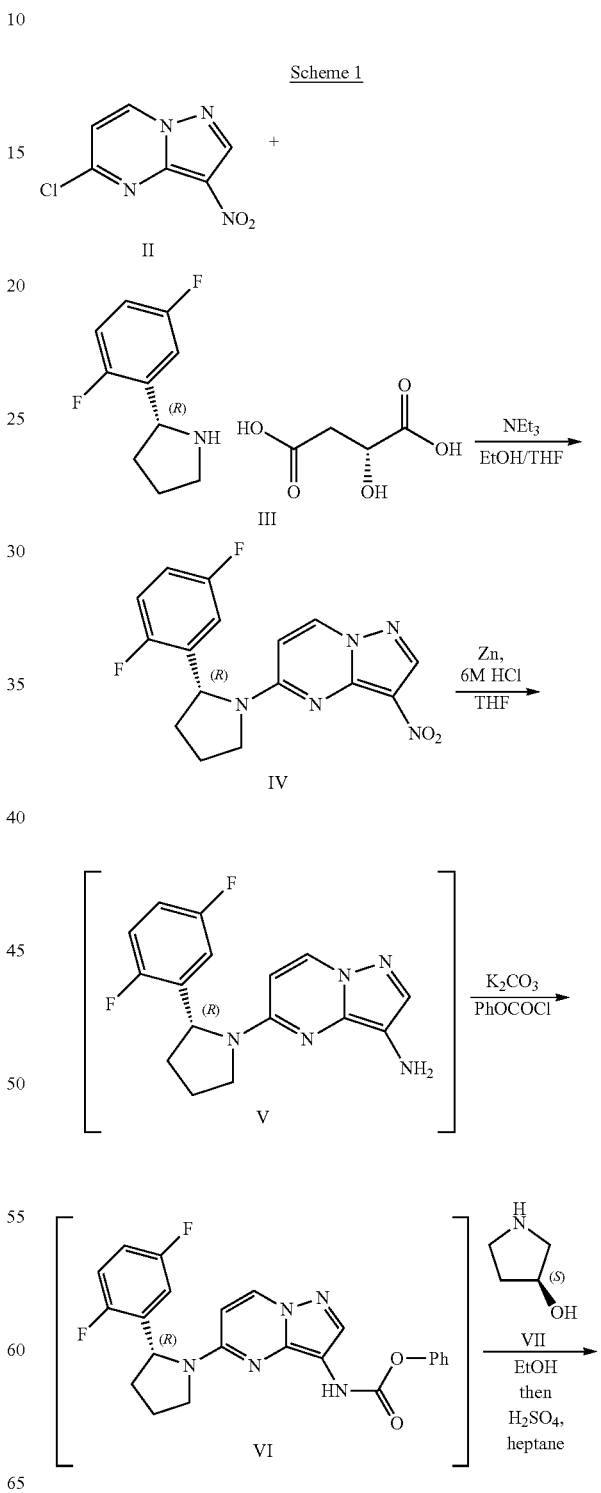

Scheme 1

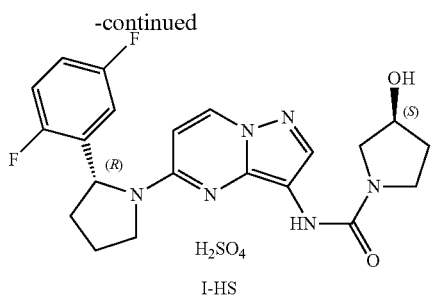

I-HS

Compounds II (5-chloro-3-nitropyrazolo[1,5-a]pyrimidine) and III ((R)-2-(2,5-difluorophenyl)pyrrolidine (R)-2-hydroxysuccinate, 1.05 eq.) were charged to a round bottom flask outfitted with a mechanical stirrer, a J-Kem temperature probe and an N₂ adaptor for positive N₂ pressure control. A solution of 4:1 EtOH:THF (10 mL/g of compound II) was added and followed by addition of triethylamine (NEt₃, 3.50 eq.) via addition funnel with the temperature reaching about 40° Celsius during addition. Once the addition was complete, the reaction mixture was heated to 50° Celsius and stirred for 0.5-3 hours to yield compound IV.

To a round bottom flask equipped with a mechanical stirrer, a J-Kem temperature probe, and an N₂ inlet compound IV was added and followed by addition of tetrahydrofuran (10 mL/g of compound IV). The solution was cooled to less than 5° Celsius in an ice bath, and Zn (9-10 eq.) was added. 6M HCl (9-10 eq.) was then added dropwise at such a rate to keep the temperature below 30° Celsius (for 1 kg scale the addition took about 1.5 hours). Once the exotherm subsided, the reaction was allowed to warm to room temperature and was stirred for 30-60 min until compound IV was not detected by HPLC. At this time, a solution of potassium carbonate (K₂CO₃, 2.0 eq.) in water (5 mL/g of compound IV) was added all at once and followed by rapid dropwise addition of phenyl chloroformate (PhOCOCl, 1.2 eq.). Gas evolution (CO₂) was observed during both of the above additions, and the temperature increased to about 30° Celsius after adding phenyl chloroformate. The carbamate formation was stirred at room temperature for 30-90 min. HPLC analysis immediately followed to run to ensure less than 1 area % for the amine being present and high yield of compound VI in the solution.

To the above solution amine VII ((S)-pyrrolidin-3-ol, 1.1 eq. based on theoretical yield for compound VI) and EtOH (10 mL/g of compound VI) was added. Compound VII was added before or at the same time as EtOH to avoid ethyl carbamate impurities from forming. The above EtOH solution was concentrated to a minimum volume (4-5 mL/g) using the batch concentrator under reduced pressure (THF levels should be <5% by GC), and EtOH (10 mL/g of compound VI) was back-added to give a total of 10 mL/g. The reaction was then heated at 50° Celsius for 9-19 hours or until HPLC shows that compound VI is less than 0.5 area %. The reaction was then cooled to room temperature, and sulfuric acid (H₂SO₄, 1.0 eq. to compound VI) was added via addition funnel to yield compound I-HS with the temperature usually exotherming at about 30° Celsius.

Example 1

Preparation of Crystalline Form (I-HS) (Method 1)

(S)—N-(5-((R)-2-(2,5-difluorophenyl)pyrrolidin-1-yl)-pyrazolo[1,5-a]pyrimidin-3-yl)-3-hydroxypyrrolidine-1-carboxamide (0.500 g, 1.17 mmol) was dissolved in EtOH (2.5 mL) and cooled to about 5° Celsius. Concentrated sulfuric acid (0.0636 mL, 1.17 mmol) was added to the cooled solution and stirred for about 10 min, while warming to room temperature. Methyl tert-butyl ether (MTBE) (2 mL) was slowly added to the mixture, resulting in the product gumming out. EtOH (2.5 mL) was then added to the mixture and heated to about reflux until all solids were dissolved. Upon cooling to room temperature and stirring for about 1 hour, some solids formed. After cooling to about 5° Celsius, the solids were filtered and washed with MTBE. After filtration and drying at air for about 15 minutes, (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate was isolated as a solid.

Example 2

Preparation of Crystalline Form (I-HS) (Method 2)

Concentrated sulfuric acid (392 mL) was added to a solution of 3031 g of (S)—N-(5-((R-2-(2,5-difluorophenyl)pyrrolidin-1-yl)-pyrazolo[1,5-a]pyrimidin-3-yl)-3-hydroxypyrrolidine-1-carboxamide in 18322 mL EtOH to form the hydrogen sulfate salt. The solution was seeded with 2 g of (S)—N-(5((R)-2-(2,5-difluorophenyl)pyrrolidin-1-yl)-pyrazolo[1,5-a]pyrimidin-3-yl)-3-hydroxypyrrolidine-1-carboxamide hydrogen sulfate and the solution was stirred at room temperature for at least 2 hours to form a slurry of the hydrogen sulfate salt. Heptane (20888 g) was added and the slurry was stirred at room temperature for at least 60 min. The slurry was filtered and the filter cake was washed with 1:1 heptane/EtOH. The solids were then dried under vacuum at ambient temperature (oven temperature set at 15° Celsius).

The dried hydrogen sulfate salt (6389 g from 4 combined lots) was added to a 5:95 w/w solution of water/2-butanone (total weight 41652 g). The mixture was heated at about 68° Celsius with stirring until the weight percent of ethanol was about 0.5%, during which time a slurry formed. The slurry was filtered, and the filter cake was washed with a 5:95 w/w solution of water/2-butanone. The solids were then dried under vacuum at ambient temperature (oven temperature set at 15° Celsius) to provide the crystalline form of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate.

Example 3

Preparation of Amorphous Form AM(HS)

To a solution of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (9.40 g, 21.94 mmol) in MeOH (220 mL) was slowly added sulfuric acid (0.1 M in MeOH, 219.4 mL, 21.94 mmol) at ambient temperature under rapid stirring. After 30 minutes, the reaction was first concentrated by rotary evaporator to near dryness, then on high vacuum for 48 h to provide amorphous form of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (11.37 g, 21.59 mmol, 98.43% yield). LCMS (apci m/z 429.1, M+H).

Example 4

Preparation of Crystalline HCl Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.554 g, 1.29 mmol) in EtOH (6 mL, 200 proof) and MTBE (10 mL) was heated to 50° C. while stirring to obtain a solution, followed by addition of hydrogen chloride (conc.) (0.108 mL, 1.29 mmol) in one portion. The reaction mixture was then allowed to cool to ambient temperature first, then cooled to about 5° C. in an ice-water bath with stirring to induce crystallization. The suspension was stirred for 4 h in the ice-water bath before it was vacuum-filtered, with the filter cake rinsed with MTBE and dried under vacuum at 55° C. to constant weight, yielding crystalline (S)—N-(5-((R)-2-(2,5-difluorophenyl)pyrrolidine-1-yl)pyrazolo[1,5-a]pyrimidin-3-yl)-3-hydroxypyrrolidine-1-carboxamide hydrochloride (0.534 g, 89% yield). LCMS (apci m/z 429.2, M+H).

Preparation of Crystalline HBr Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.505 g, 1.18 mmol) in EtOH (6 mL, 200 proof) and MTBE (10 mL) was heated to 50° C. while stirring to obtain a solution, followed by addition of hydrogen bromide (33% aq.) (0.213 mL, 1.18 mmol) in one portion. The reaction mixture was heated to reflux to obtain a mostly clear solution with small amount of oily residue on glass wall of reaction vessel. Upon cooled to ambient temperature, precipitation appeared and the oily residue solidified. The mixture was heated to 50° C. again, then allowed to cool to room temperature and stirred for overnight. The suspension was vacuum-filtered, with the filter cake rinsed with MTBE and dried under vacuum at 55° C. to constant weight, yielding crystalline (S)—N-(5-((R)-2-(2,5-difluorophenyl)pyrrolidin-1-yl)pyrazolo[1,5-a]pyrimidin-3-yl)-3-hydroxypyrrolidine-1-carboxamide hydrobromide (0.51 g, 85% yield). LCMS (apci m/z 429.3, M+H).

Preparation of Crystalline Mesylate Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.532 g, 1.24 mmol) in EtOH (2.7 mL, 200 proof) and MTBE (5.3 mL) was heated to 50° C. while stirring to obtain a solution, followed by addition of methanesulfonic acid (0.076 mL, 1.24 mmol) in one portion. The reaction mixture was heated to reflux to obtain a mostly clear solution with small amount of particulates. Upon cooled to ambient temperature, precipitation appeared along with some oily residue. Additional EtOH (0.5 mL, 200-proof) and methanesulfonic acid (0.010 mL) were added to obtain a solution. The reaction mixture was heated to 50° C. again, then allowed to cool to room temperature and stirred for 1 h. The suspension was vacuum-filtered, with the filter cake rinsed with MTBE and dried under vacuum at 55° C. to constant weight, yielding crystalline (S)—N-(5-((R)-2-(2,5-difluorophenyl)pyrrolidin-1-yl)pyrazolo[1,5-a]pyrimidin-3-yl)-3-hydroxypyrrolidine-1-carboxamide methanesulfonate (0.51 g, 78% yield). LCMS (apci m/z 429.4, M+H).

Preparation of Crystalline Camsylate Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.500 g, 1.17 mmol) and S-(+)-camphorsulfonic acid (0.271 g, 1.17 mmol) in EtOH (3 mL, 200 proof) and MTBE (5 mL) was heated to reflux while stirring to obtain a solution. Upon cooled to ambient temperature, precipitation appeared. The suspension was stirred at room temperature for overnight, then vacuum-filtered, with the filter cake rinsed with MTBE and dried under vacuum at 55° C. to constant weight, yielding crystalline (S)—N-(5-((R)-2-(2,5-difluorophenyl)pyrrolidin-1-yl)pyrazolo[1,5-a]pyrimidin-3-yl)-3-hydroxypyrrolidine-1-carboxamide ((1S,4R)-7,7-dimethyl-2-oxobicyclo[2.2.1]heptan-1-yl)methanesulfonate.

Example 5

Comparison of (S)—N-(5((R)-2-(2,5-difluorophenyl)-pyrrolidin-1-yl)-pyrazolo[1,5-a]pyrimidin-3-yl)-3-hydroxypyrrolidine-1-carboxamide salts Other salt forms of (S)—N-(5((R)-2-(2,5-difluorophenyl)-pyrrolidin-1-yl)-pyrazolo[1,5-a]pyrimidin-3-yl)-3-hydroxypyrrolidine-1-carboxamide, e.g., hydrogen chloride, hydrogen bromide, mesylate, and camsylate salts (see Example 4), were compared to crystalline form (I-HS) by determining their differential scanning calorimetry (DSC) melting point, dynamic vapor sorption (DVS) weight gain and stability on an aluminum slide at 40° Celsius and 75% relative humidity (RH). The DSC and DVS measurement were performed as described above with the results being summarized in Table 14.

TABLE 14

Physicochemical Properties of Crystalline Salts of (S)-N-(5-((R)-2-(2,5-difluorophenyl)-pyrrolidin-1-yl)-pyrazolo[1,5-a]pyrimidin-3-yl)-3-hydroxypyrrolidine-1-carboxamide

| Crystalline Salt | DSC Melting Point onset to max | DVS weight gain (outcome) | Stability at 40° Celsius/75% RH (aluminum slide) |
|---|---|---|---|
| Hydrogen Sulfate (I-HS) | 186-206° Celsius | ~1% gain at 80% RH<br>A 2% gain at 95% RH No change | 10 days<br>No form change |
| HCl | 124-134° Celsius | ~1% gain at 50% RH<br>at 50-60% RH a form change occurred | After 1 hour a form change occurred |
| HBr | 177-185° Celsius | ~3.9% gain at 80% RH<br>~25% gain at 90% RH (deliquesced) | After 2 weeks became amorphous |
| Mesylate | 183-186° Celsius | ~9% gain at 80% RH<br>~50% gain at 90% RH (crystalline) | Deliquesced overnight |
| Camsylate | 170-183° Celsius | Not Tested | Not Tested |

Example 6

TrkA and TrkB Enzyme Assay

The affinity of a compound binding to Trk kinase is measured using Invitrogen's LanthaScreen™ Eu Kinase Binding technology. Briefly, His-tagged recombinant human Trk cytoplasmic domain from Invitrogen (5 nM TRK A—Cat. No. PV3144 or 10 nM TRK B—Cat. No. PV3616)

is incubated with 5 nM Alexa-Fluor® Tracer 236 (PR9078A), 2 nM biotinylated anti-His (Cat. No. M4408), and 2 nM europium-labeled Streptavidin (Cat No. PV5899) along with test compound in a buffer consisting of 25 mM MOPS, pH 7.5, 5 mM $MgCl_2$, 0.005% Triton X-100, and 2% DMSO. The compound is typically prepared in a three-fold serial dilution in DMSO and added to the assay to give the appropriate final concentration. After a 60-minute incubation at 22° C., the reaction is measured using a PerkinElmer EnVision multimode plate reader via TR-FRET dual wavelength detection, and the percent of control (POC) calculated using a ratiometric emission factor. 100 POC is determined using no test compound and 0 POC is determined using a concentration of control compound that completely inhibits the enzyme. The POC values are fit to a 4 parameter logistic curve and the $IC_{50}$ value is point where the curve crosses 50 POC. Crystalline form (I-HS) had an averaged $IC_{50}$ of 8.4 nM when tested in this assay for TrkA and an averaged $IC_{50}$ of 4.2 when tested in this assay for TrkB.

Example 7

TRK Fusion Proteins Drive Oncogenesis and are Inhibited by the Crystalline Form (I-HS)

Figure 8:
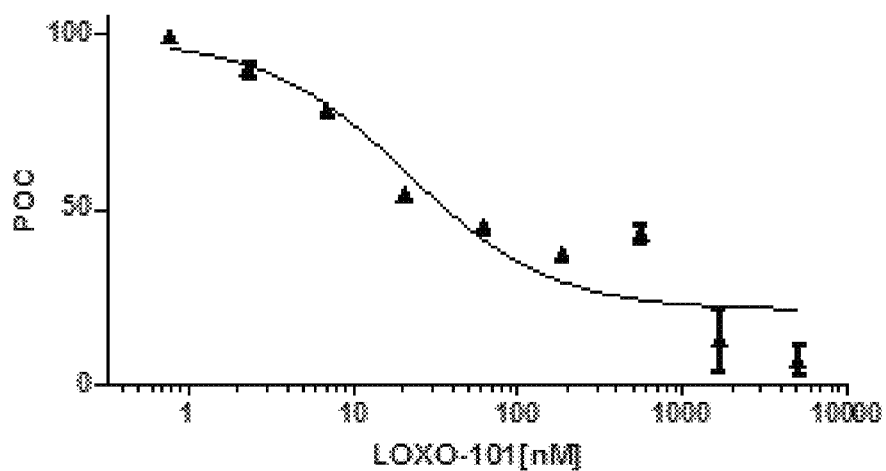
FIG. 8 is a graph showing the dose dependent inhibition of the proliferation of CUTO-3F lung adenocarcinoma cells harboring a MPRIP-NTRK1 fusion protein using the crystalline form (I-HS).
Figure 9:
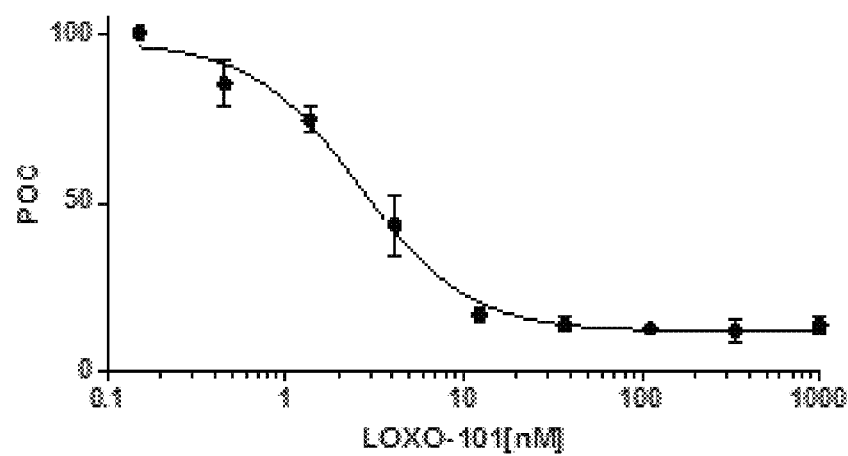
FIG. 9 is a graph showing the dose dependent inhibition of the proliferation of KM12 colorectal cancer cells harboring a TPM3-NTRK1 fusion protein using the crystalline form (I-HS).
Figure 10:
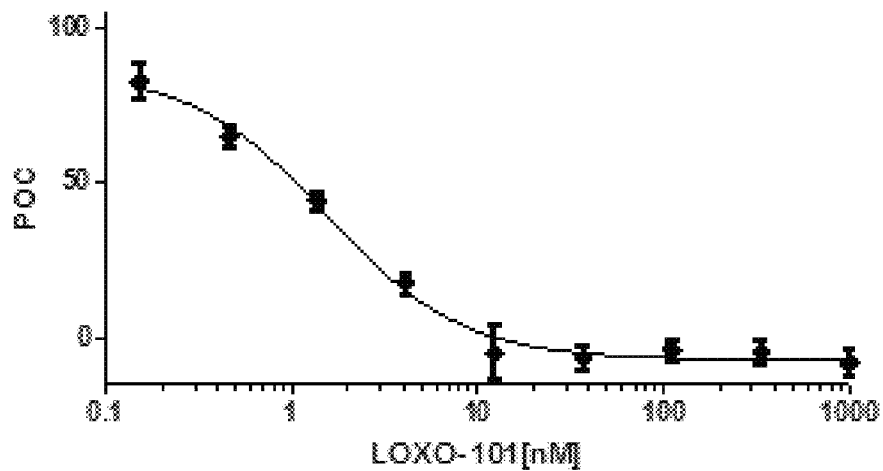
FIG. 10 is a graph showing the dose dependent inhibition of the proliferation of MO-91 acute myeloid leukemia cells harboring a ETV6-NTRK3 fusion protein using the crystalline form (I-HS).

A set of experiments were performed to determine whether the crystalline form (I-HS) would inhibit cell proliferation in three different cancer cell line models harboring different Trk gene fusions: CUTO-3F cell line, KM12 cell line, and a MO-91 cell line. The CUTO-3F cell is derived from a patient with lung adenocarcinoma harboring the MPRIP-NTRK1 gene fusion. The KM12 cell line is a colorectal cancer cell line harboring the TPM3-NTRK1 fusion (Vaishnavi et al., *Nature Med.* 19:1469-1472, 2013). The MO-91 cell line is derived from an acute myeloid leukemia patient harboring the ETV6-NTRK3 fusion (Taipale et al., *Nature Biotech.* 31:630-637, 2013). Measurement of the proliferation of the cells following treatment with the crystalline form (I-HS) demonstrated a dose-dependent inhibition of cell proliferation in all three tested cell lines (FIGS. 8-10). The $IC_{50}$ was less than 100 nm for the CUTO-3F cells (FIG. 8) and less than 10 nm for the KM12 cells and the MO-91 cells (FIGS. 9 and 10, respectively).

Figure 11:
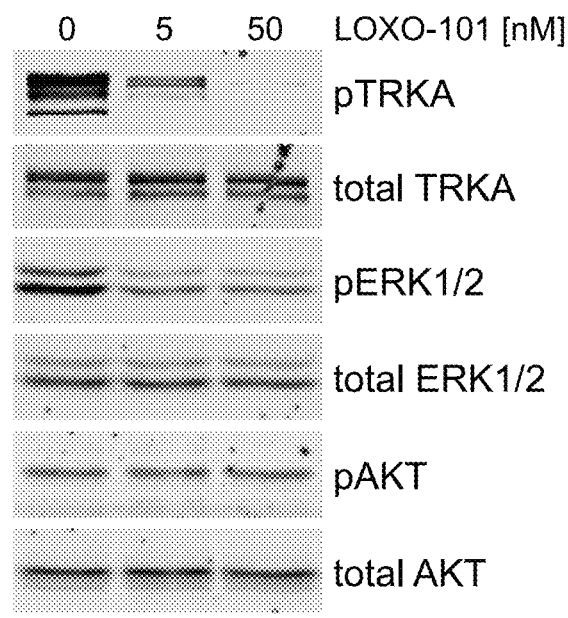
FIG. 11 is an immunoblot showing that the crystalline form (I-HS) inhibits the activation of MPRIP-TRKA kinase, ERK1/2 in CUTO-3F cells, and AKT activity in KM12 cells. The cells were treated for 2 hours with the crystalline form (I-HS) at the indicated doses.
Figure 12:
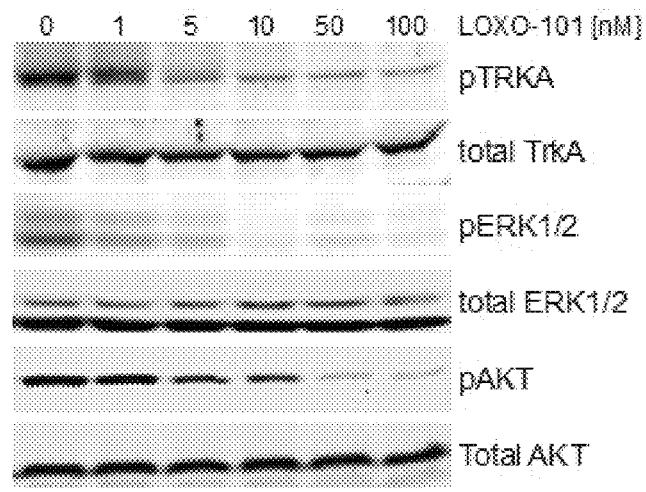
FIG. 12 is an immunoblot showing that the crystalline form (I-HS) inhibits the activation of TPM3-TRKA kinase and downstream ERK1/2 and AKT activity in KM12 cells. The cells were treated for 2 hours with the crystalline form (I-HS) at the indicated doses.
Figure 13:
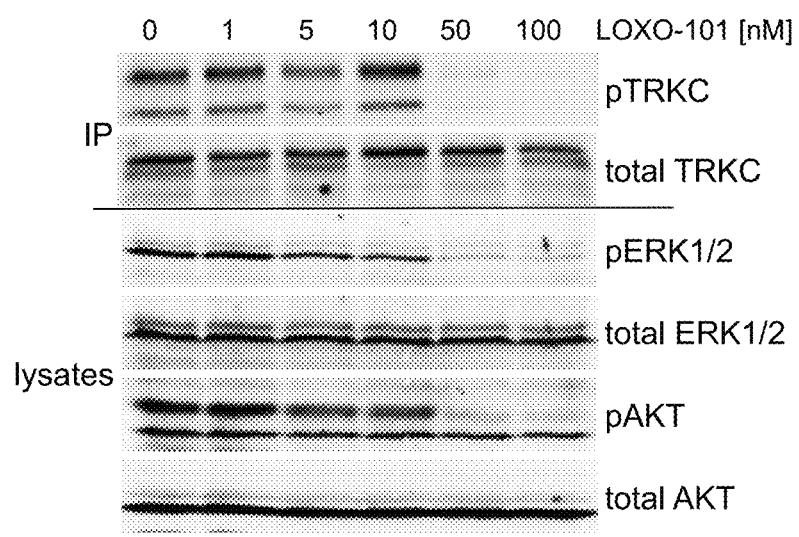
FIG. 13 is an immunoblot showing that the crystalline form (I-HS) inhibits TEL-TRKC kinase and ERK1/2 and AKT activity in MO-91 cells. The cells were treated for 2 hours with the crystalline form (I-HS) at the indicated doses.

Consistent with the inhibition of cellular proliferation, inhibition of phosphorylation of the MPRIP-TRKA oncoprotein and ERK1/2 was observed in the CUTO-3F cells using low doses of the crystalline form (I-HS) (FIG. 11), inhibition of the phorphorylation of TPM3-TRKA, pAKT, and pERK1/2 in the KM12 cells using low doses of the crystalline form (I-HS) (FIG. 12), and inhibition in the phosphorylation of the TEL-TRKC oncoprotein (encoded by ETV6-NTRK3), pAKT, and pERK1/2 in the MO-91 cells using low doses of the crystalline form (I-HS) (FIG. 13). Together these data show that Trk fusion proteins are constitutively active, and regulate critical downstream signaling pathways, such as MAPK and AKT, and are inhibited by the crystalline form (I-HS). These data also indicate that the crystalline form (I-HS) can use used to treat different cancers that express a dysregulated Trk (e.g., a constitutively active form of a Trk protein (e.g., a Trk fusion protein or a Trk point mutation)).

Example 8

The Crystalline Form (I-HS) Successfully Treated a Subject Having Undifferentiated Sarcoma A 41-year-old woman presented with a firm mass in her left groin. Initial imaging was used to confirm a 10-cm mass within the musculature of her anterior thigh. An open biopsy revealed an undifferentiated sarcoma. Initial staging scans demonstrated multiple bilateral 4-13 mm pulmonary nodules consistent with metastatic disease. The woman was enrolled on a phase 2 trial of sorafenib with chemotherapy, pre-operative radiation, and limb-sparing surgery (ClinicalTrials.gov number NCT02050919). After two weeks of sorafenib administered at 400 mg daily, the patient received epirubicin at 30 $mg/m^2$ daily and ifosfamide at 2,500 $mg/m^2$ daily with mesna for three consecutive days, with continuation of daily sorafenib. The tumor became progressively more painful during these five weeks of systemic therapy. During simulation for pre-operative radiation, extension of the tumor was noted cranially within the psoas muscle, precluding the safe administration of effective radiation doses due to predicted bowel toxicity. The patient therefore came off the protocol and proceeded to surgical resection.

Resection of the primary tumor achieved negative margins and review of the pathologic specimen confirmed 90% tumor necrosis. A restaging chest CT (shown in FIG. 21A) obtained 9 weeks after initial scans snowed worsening metastatic disease, with the largest nodule now measuring at 18 mm. The patient's post-operative course was complicated by a polymicrobial wound infection requiring repeated wound debridement and prolonged antibiotic therapy. Repeat chest CT was obtained before resumption of chemotherapy and demonstrated dramatic progression over the prior 9 weeks, with multiple pulmonary nodules greater than 3 cm, the largest nearly 7 cm, and a large left pleural effusion. After placement of a tunneled pleural drain and initiation of supplemental home oxygen, the patient received doxorubicin at 75 $mg/m^2$ once, while awaiting enrollment for treatment with the crystalline form (I-HS).

Figure 14:
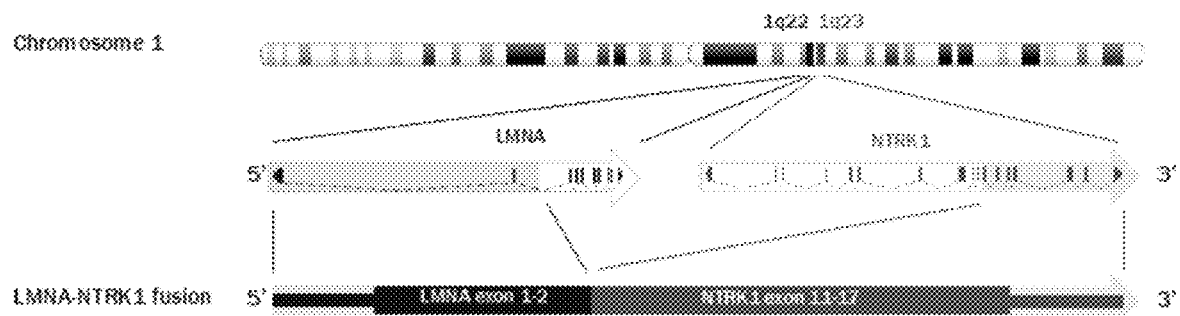
FIG. 14 is a schematic depicting the LMNA-NTRK1 gene fusion identified in the patient's tumor sample: the joining of the first two exons of LMNA (NM_170707) with exon 11-17 of NTRK1 (NM_002529).

The patient's diagnostic, open tumor biopsy was tested using the FoundationOneHeme panel (Foundation Medicine, Cambridge, Mass.). This multi-target comprehensive genomic profiling (CGP) assay using DNA and RNA sequencing of hundreds of cancer-related genes demonstrated the presence of a gene fusion encoding exons 1-2 of the lamin A/C gene (LMNA) and exons 11-17 of the NTRK1 gene resulting in the LMNA-NTRK1 fusion gene (FIG. 14). CGP also showed the loss of the tumor suppressor CDKN2A/B (not shown), but no other known oncogenic mutations.

Figure 15:
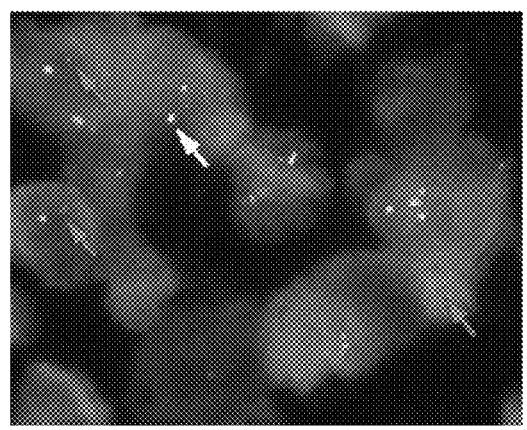
FIG. 15 is a fluorescence micrograph from the NTRK1 break-apart FISH assay, which shows both paired green (5' NTRK1) and red (3' NTRK1) signals corresponding to the normal gene (yellow arrow), and isolated red signals (red arrows) are observed in tumor nuclei (stained blue with DAPI) indicate a chromosomal deletion that leads to a NTRK1 gene fusion.
Figure 16:
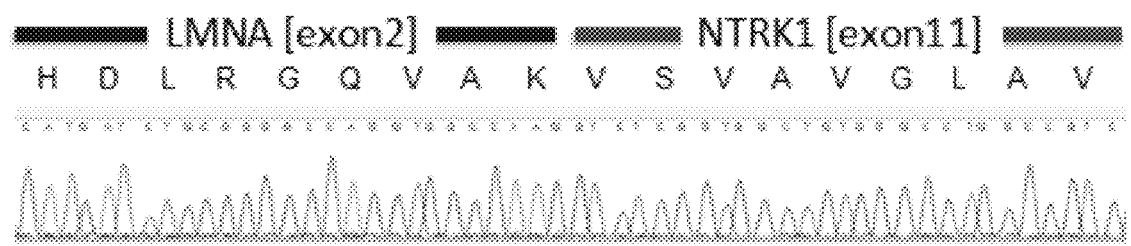
FIG. 16 is a chromatograph of DNA sequencing of the RT-PCR product using LMNA (5') and NTRK1 (3') primers indicating the fusion breakpoint between exon 2 LMNA and exon 11 of NTRK1.

Subsequently, a break-apart fluorescence in situ hybridization (FISH) assay performed on the patient's tumor sample exhibited a predominantly single 3' NTRK1 (red fluorescence signal) pattern in 64% of tumor nuclei, consistent with a genomic alteration involving the NTRK1 gene locus, most likely secondary to a genomic deletion between the two genes given the location and orientation of both LMNA and NTRK1 on the large arm of chromosome 1 (FIG. 15). mRNA expression of the novel fusion transcript from the gene fusion was confirmed by RT-PCR and sequencing (FIG. 16).

Figure 17:
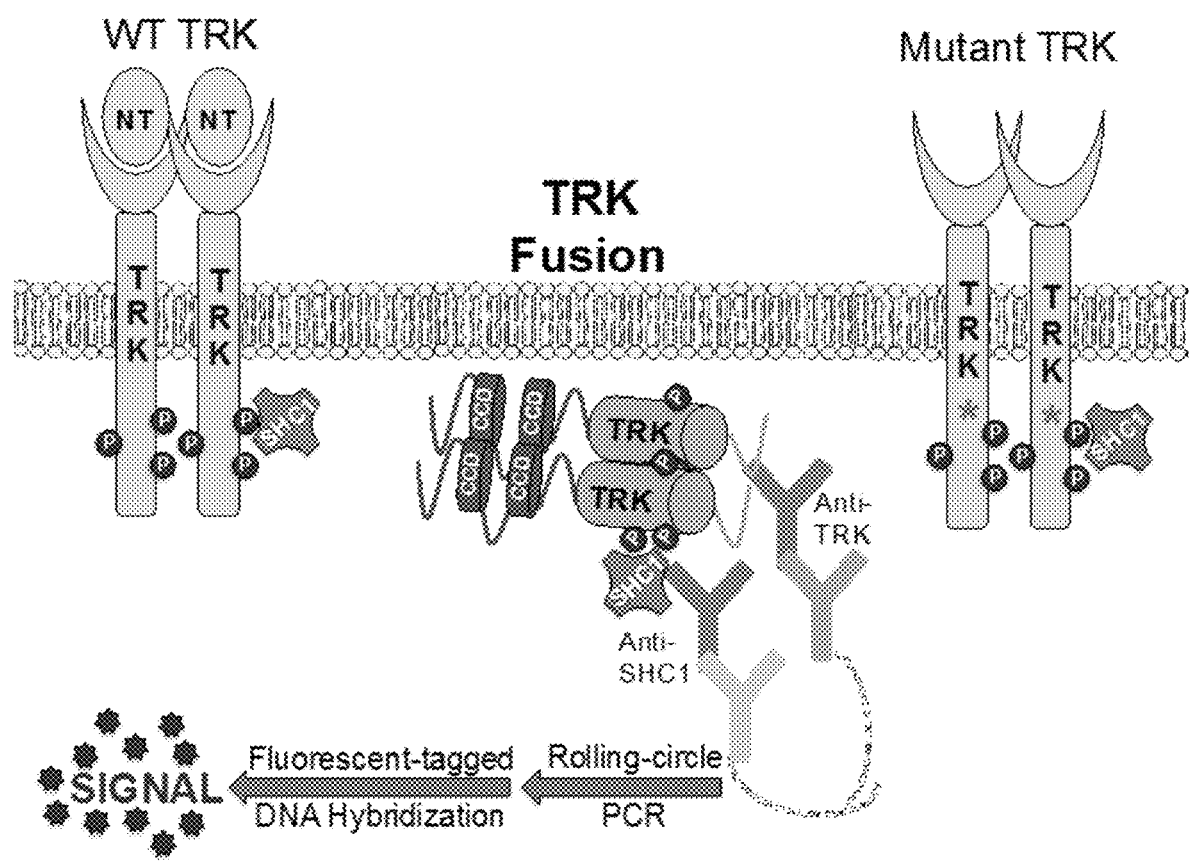
FIG. 17 is a schematic of the TRK-SHC1 proximity ligation assay (PLA). This cartoon demonstrates the detection of proximal (<40 nM) TRK and SHC1 proteins in tumor cells. The TRK antibody (rabbit) used can detect the c-terminus of TRKA (encoded by NTRK1), TRKB (NTRK2), or TRKC (NTRK3) proteins. SHC1 is detected by a SHC1 antibody (mouse). Binding of species-specific secondary antibodies with covalently attached complementary nucleotide sequences allows an in situ PCR reaction to generate DNA, which can be detected by fluorescence in situ hybridization visualized in the method as red dots. The assay has the potential to detect activated TRK regardless of mechanism of activation (gene fusion, mutation, or autocrine/paracrine activation of the wildtype) of TRK receptor family member (TRKA/B/C).
Figure 18:
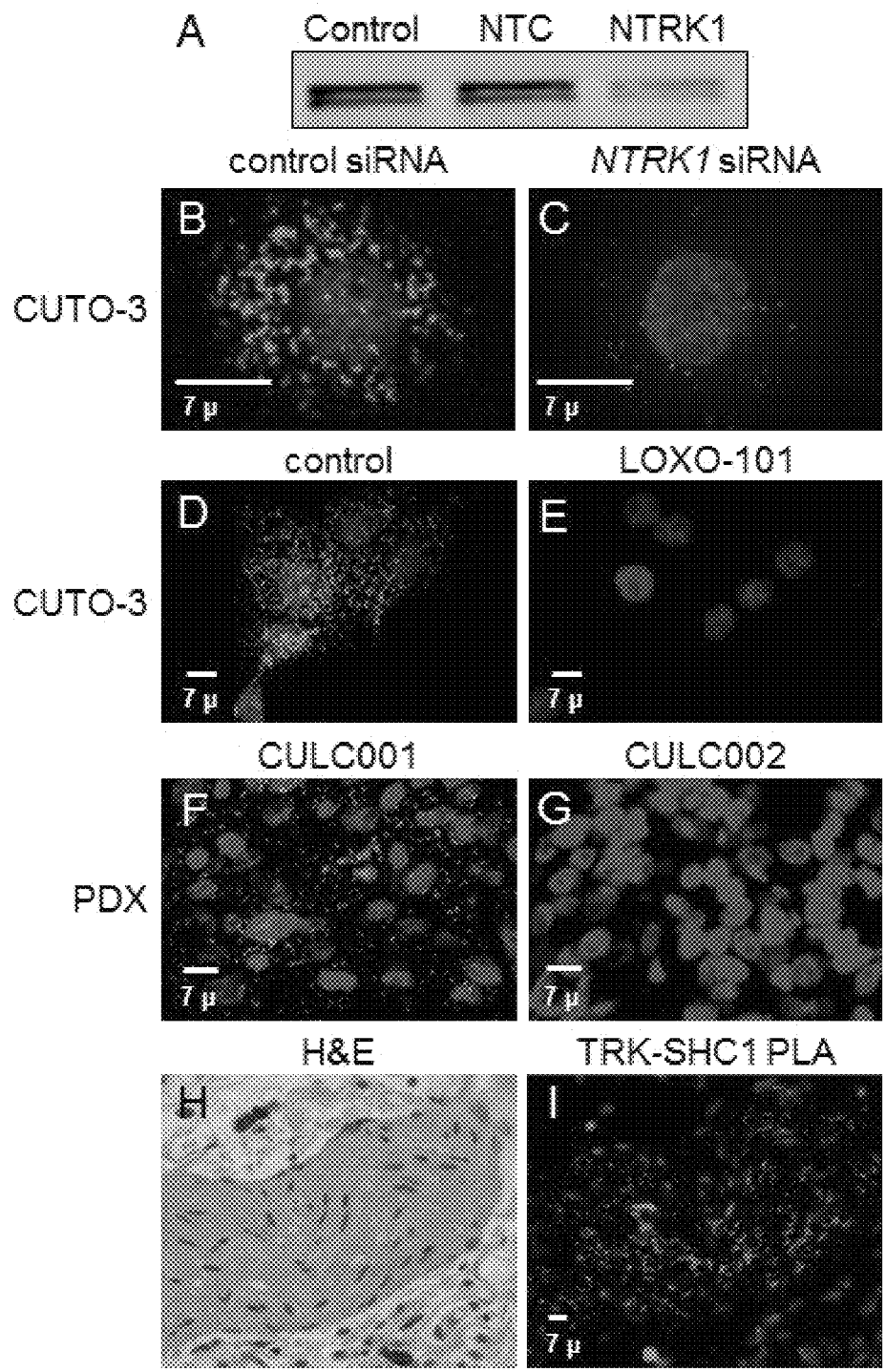
FIG. 18 is a set of data that validate the TRK-SHC1 PLA. (A) The CUTO-3 cell line, derived from a malignant pleural effusion from a patient with stage IV lung adenocarcinoma harboring the MPRIP-NTRK1 gene fusion, was transfected with a non-targeting control (NTC) siRNA, NTRK1-directed siRNA, or untreated (control) and assayed for TRKA protein expression. Western blot analysis demonstrates a marked decrease in the TRKA protein levels, and corresponds to the MPRIP-TRKA fusion protein that migrates with an apparent molecular weight of 170 kD. TRK-SHC1 PLA was performed in cells treated as in (A) demonstrating a robust positive signal in the siRNA control (B), but proportional decrease in the NTRK1 siRNA (C). CUTO-3 cells were treated with DMSO (D) or crystalline form (I-HS) at a concentration of 100 nM (E) for 2 hours demonstrating disruption of TRKA-SHC1 complexes in the crystalline form (I-HS) treated sample compared to control. CULC001 is a patient-derived tumor xenograft (PDX) derived from the same tumor as the CUTO-3 cell line and harbors the MPRIP-NTRK1 gene fusion (not shown). CULC002 is a PDX from a NSCLC patient without a known driver (ALK, ROS1, EGFR, KRAS, and BRAF negative) and is negative for an NTRK1 gene fusion by NTRK1 break-apart FISH (not shown). TRK PLA analysis demonstrates a robust signal in CULC001 (F) but no signal in CULC002 (G) tumor nuclei. Panels (H) and (I) show a nerve bundle from the CULC001 PDX. TRK-SHC1 PLA is positive only in this region of the CULC002 tumor sample and is suggestive of autocrine signaling in a TRKA, TRKB, or TRKC receptor as this family is expressed in nervous tissue and serves as internal positive control for this otherwise negative tumor sample.
Figure 19:
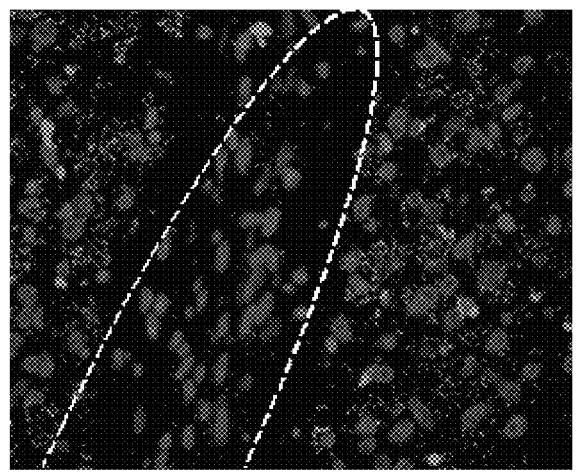
FIG. 19 is an image from a TRK SHC1 proximity ligation assay and a control. (A) The TRK-SHC1 proximity ligation assay demonstrates robust signaling in the tumor nuclei but weak signaling in the thick walled blood vessel. Nuclei were stained with DAPI (blue) and the red signals represent a positive PLA indicative of TRKA-SHC1 protein complexes. A blood vessel is indicated within the partial ellipse (dotted white line). (B) Adjacent tumor tissue section stained with hematoxylin and eosin indicating a thick-walled blood vessel (within partial ellipse indicated by dotted white line) and flanking tumor nuclei.
Figure 19:
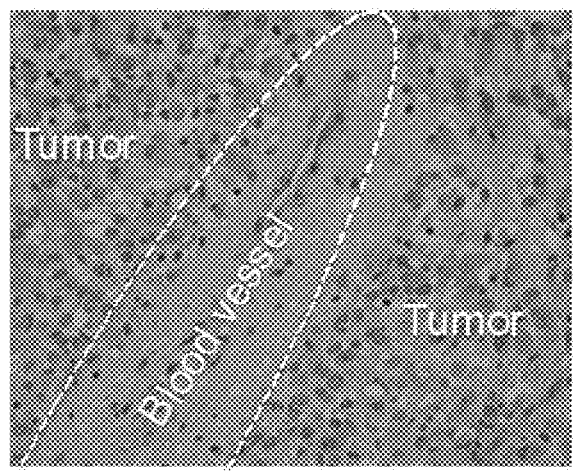
Figure 20:
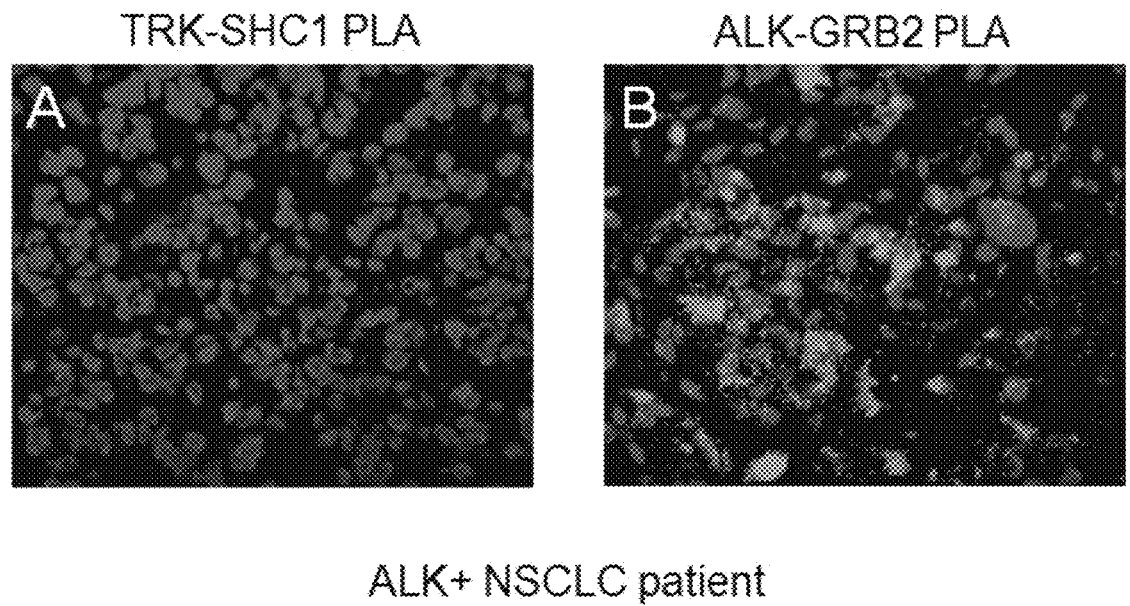
FIG. 20 are a set of images showing the TRK and ALK PLA in an ALK+ tumor sample. FFPE tumor sample from an ALK+ patient (autopsy sample) was assayed using the TRK-SHC1 PLA (A) demonstrating an absence of signal or ALK-GRB2 PLA (B) showing robust ALK signaling.

A novel proximity ligation assay (PLA) was performed using the patient's tumor sample in order to assess both protein expression and functional activity of the fusion oncoprotein. PLAs are unique because they can detect functional signaling complexes between a kinase and one of its adaptors in situ. In this assay, TRKA complexed with its preferred adaptor, SHC1, which binds to Y496 in the TRKA kinase domain, was measured (FIG. 17). The assay was validated in both human cell lines and formalin-fixed patient-derived tumor xenografts (PDX) tumor samples (FIG. 18). RNAi knockdown of NTRK1 was discovered to disrupt TRKA-SHC1 complexes in the CUTO-3 cell line harboring the MPRIP-NTRK1 fusion gene (FIG. 18A-C) as does inhibition with the crystalline form (I-HS) (FIGS. 18D and 18E). The TRK PLA detects functional signaling complexes in a FFPE tumor sample from a patient derived xenograft (PDX), CULC001, harboring the MPRIP-NTRK1 gene fusions but not the PDX CULC002, which does not harbor a known oncogenic driver mutation (FIGS. 18F and 18G). The TRK-SHC PLA can also detect non-oncogenic signaling complexes as shown by a positive signal in a region of peripheral nerve tissue of the CULC001 PDX, where the TRK family of receptors have high expression an activity mediated by the neurotrophins Application of this assay to the patient's tumor sample demonstrated robust signaling associated with tumor nuclei, but only a weak signal in the blood vessel (human endothelial cells express TRKA, consistent with oncogenic signaling by the LMNA-TRKA oncoprotein (FIGS. 19A and B). The TRK-SHC1 PLA demonstrated a negative result on a tumor sample from an ALK+ NSCLC patient, whereas the ALK-GRB2 PLA was positive (FIG. 20), further demonstrating the ability of this assay to detect oncogenic signaling in human tumor samples.

The presence of the LMNA-NTRK1 fusion detected by FoundationOneHeme assay and then validated by FISH and RT-PCR combined with the evidence of TRKA protein expression and functional activity of the TRK pathway in the patient's tumor sample suggests the patient has a TRK-driven cancer suitable for treatment with a TRK-specific inhibitor.

Figure 21:
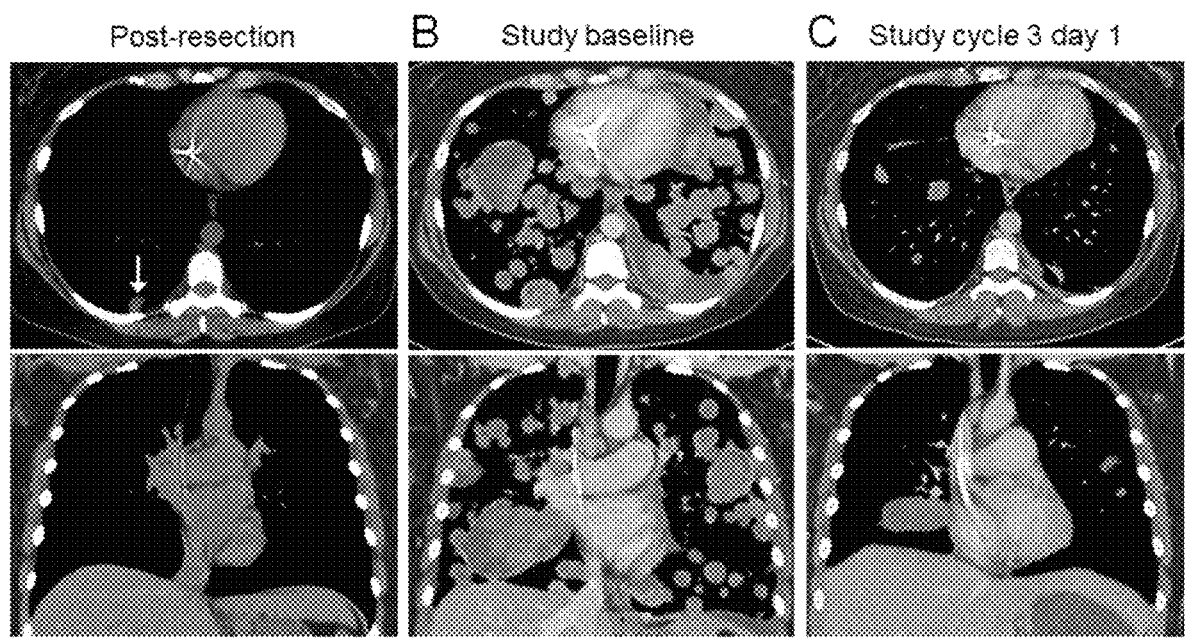
FIG. 21 is a set of three computed tomography images from a subject having undifferentiated sarcoma. CT images were obtained following pre-operative chemotherapy and primary tumor resection with arrow indicating the presence of an 18-mm right lung nodule (A), baseline imaging just prior to dosing with the crystalline form (I-HS) on study (B), and following 1 cycle (28 days) of dosing of with the crystalline form (I-HS) (C). The patient was observed to have metastatic disease only in the lungs and therefore the CT scan images show axial (top) and coronal (bottom) images focusing on the thoracic cavity. The images demonstrate an initial rapid disease progression (A-B, 13 week interval) followed by a marked tumor response with decreased size and/or resolution of the numerous pulmonary metastases (B-C, 4 week interval).
Figure 22:
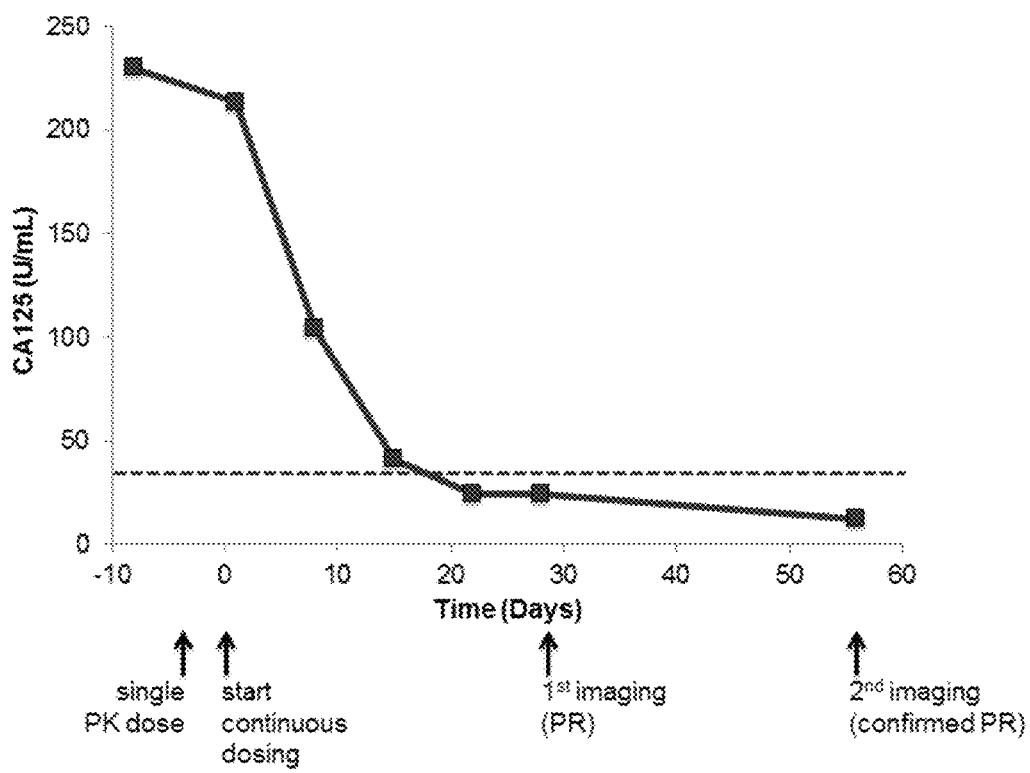
FIG. 22 is a graph showing the serum CA125 levels in a patient having undifferentiated sarcoma treated with crystalline form (I-HS) over time. Serum CA125 levels were found to be elevated in this patient, and subsequently followed as a potential indicator of activity. Serum CA125 was drawn at baseline (day −8) prior to dosing and at the indicated time point points following the initiation of dosing at day −3 through day 56 demonstrating a time-dependent decrease in this tumor marker. The dashed red line indicates the upper limit of normal (35 U/mL) of this laboratory test.

Based on multiple lines of genetic and functional biomarker data suggesting the presence of a TRK driver oncogene, the patient was referred for consideration of enrollment into the phase 1 trial of the crystalline form (I-HS). A month later, the patient was found eligible for the trial and provided written informed consent. The baseline CT scan showed continued tumor progression with multiple large pulmonary metastases in both lungs, although the pleural effusion had resolved following placement of the pleural drain (FIG. 21C). On clinical presentation the patient had significant exertional dyspnea and required 5 L of supplemental oxygen to maintain an oxygen saturation of 90%. Baseline laboratory values were notable for an elevated CA125 tumor marker level (FIG. 22). The patient received an initial dose of 100 mg of the crystalline form (I-HS) three days before the initiation of continuous dosing, followed by the same dose approximately 12 hours later on the same day, with 48 hours of pharmacokinetic and safety assessment as per the study protocol. The patient started cycle 1 day 1 three days later. The patient was seen weekly for pharmacokinetic and safety analysis. No drug-related adverse events were noted and the patient experienced weekly improvement in her exertional dyspnea during this 4-week period. The CA125 levels normalized over cycle 1. A CT was performed prior to the start of cycle 2 day 1, which demonstrated a marked improvement in multiple pulmonary metastases and was deemed a partial response by RECIST 1.1. A repeat CT was performed prior to cycle 3 day 1 and demonstrated an ongoing response and thus confirmed a partial response by RECIST 1.1 (FIG. 21C). Clinically, the patient had significantly improved exertional dyspnea and was no longer requiring supplemental oxygen with an oxygen saturation of 97% on room air. After four months of dosing, the patient did not have any adverse events that were attributed to the crystalline form (I-HS). These data show that the crystalline form (I-HS) is able to treat an undifferentiated sarcoma in a subject, as well as other cancers that have a dysregulated Trk protein (e.g., a constitutively active form of a Trk protein, e.g., Trk fusion proteins or Trk point mutations).

The LMNA-NTRK1 gene fusion has been previously reported in Spitzoid nevi and is constitutively activated when expressed in cells resulting in activation of ERK1/2, AKT and PLCγ demonstrating its oncogenicity (Taipale et al., *Nature Biotech.* 31:630-637, 2013). Foundation Medicine (FM) has previously tested 1272 soft tissue sarcoma samples with the FoundationOneHeme CGP test resulting in the detection of 8 NTRK1 or NTRK3 fusions, including the patient described in this case report (Table 15). Notably, 6 of the 8 sarcoma patients with NTRK fusions are under the age of 25 (Fisher's exact, P-value=$4\times10^{-4}$) and 4 of the 8 are under the age of 5 (Fisher's exact, P-value=$2\times10^{-5}$), indicating an increased detection rate of NTRK fusions among pediatric patients (4.1%; 95% CI 1.8%-9.3%) and particularly those under the age of 5 (14.3%; 95% CI 5.7%-31.5%). Also of interest, one of the gene fusions detected combines the majority of the NTRK3 gene (exon 1-17) to the 3' end of the HOMER2 gene (exons 2-9), which contains a dimerization domain (coiled-coil domain), and therefore represents a 3' gene fusion event that has now been described for multiple other RTK-encoding genes such as EGFR, AXL, and FGFR3 (Sleijfer et al., *Eur. J. Cancer* 46:72-83, 2010; Linch et al., *Clin. Oncol.* 11:187-202, 2014; Rutkowski et al., *J. Eur. Acad. Dermatol. Venereol.* 25:264-270, 2011).

TABLE 15

Clinical Characteristics and NTRK Fusion Gene Details of Soft Tissue Sarcoma Patients

| Histology | 5' Gene | 5' Last Exon | 3' Gene | 3' First Exon | Gender | Age |
|---|---|---|---|---|---|---|
| soft tissue sarcoma (nos)(n = 179) | LMNA | 2 | NTRK1 | 11 | F | 41 |
| soft tissue sarcoma (nos)(n = 179) | LMNA | 10 | NTRK1 | 11 | M | 22 |
| soft tissue fibrosarcoma (n = 28) | LMA | 10 | NTRK1 | 12 | M | Under 5 |
| soft tissue fibrosarcoma (n = 28) | SQSTM1 | 2 | NTRK1 | 10 | F | Under 5 |
| soft tissue schwannoma (n = 3) | TPM3 | 7 | NTRK1 | 10 | M | Under 5 |
| soft tissue hemangioma (n = 4) | ETV6 | 5 | NTRK3 | 15 | F | Under 5 |
| soft tissue solitary fibrous tumor (n = 28) | TFC | 6 | NTRK3 | 14 | M | 17 |
| soft tissue sarcoma (nos)(n = 179) | NTRK3 | 17 | HOMER2 | 2 | F | 68 |

Figure 23:
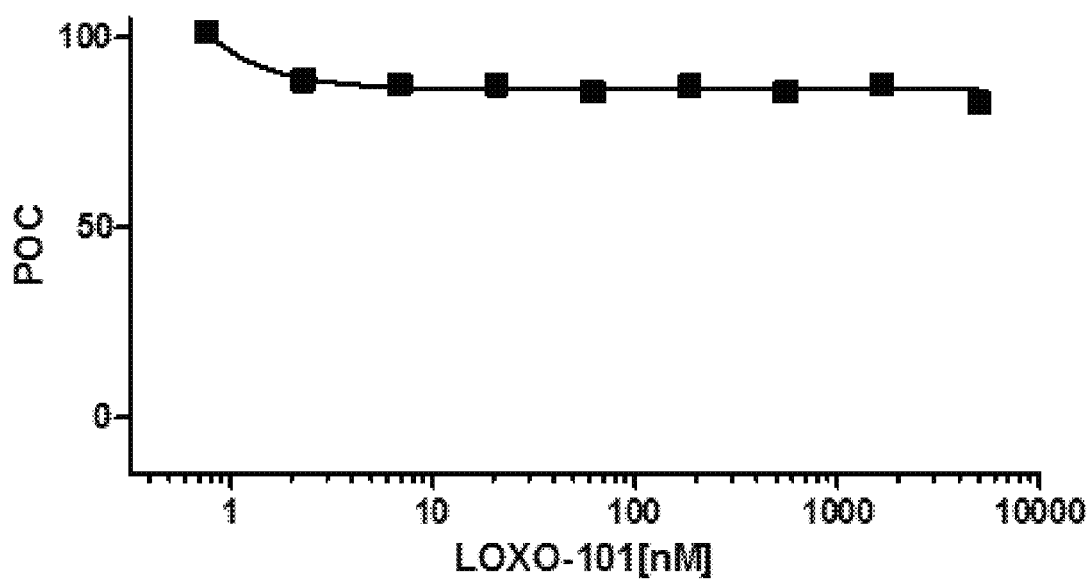
FIG. 23 is a graph showing the dose dependent inhibition of the proliferation of HCC78 cells harboring a SLC34A2-ROS1 fusion protein using the crystalline form (I-HS).
Figure 24:
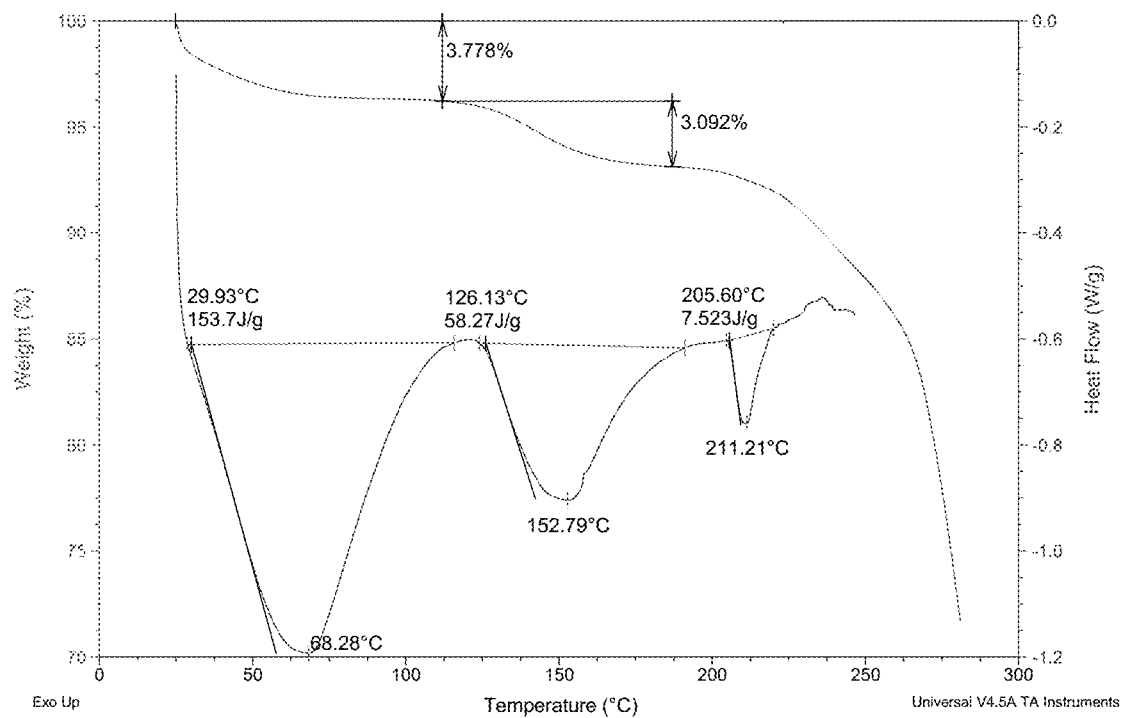
FIG. 24 is a graph showing thermographic data for AM(HS)1. The top line of the graph is a plot of the thermogravimetric analysis (TGA) for the compound, while the bottom line is a plot of the differential scanning calorimetry (DSC).
Figure 25:
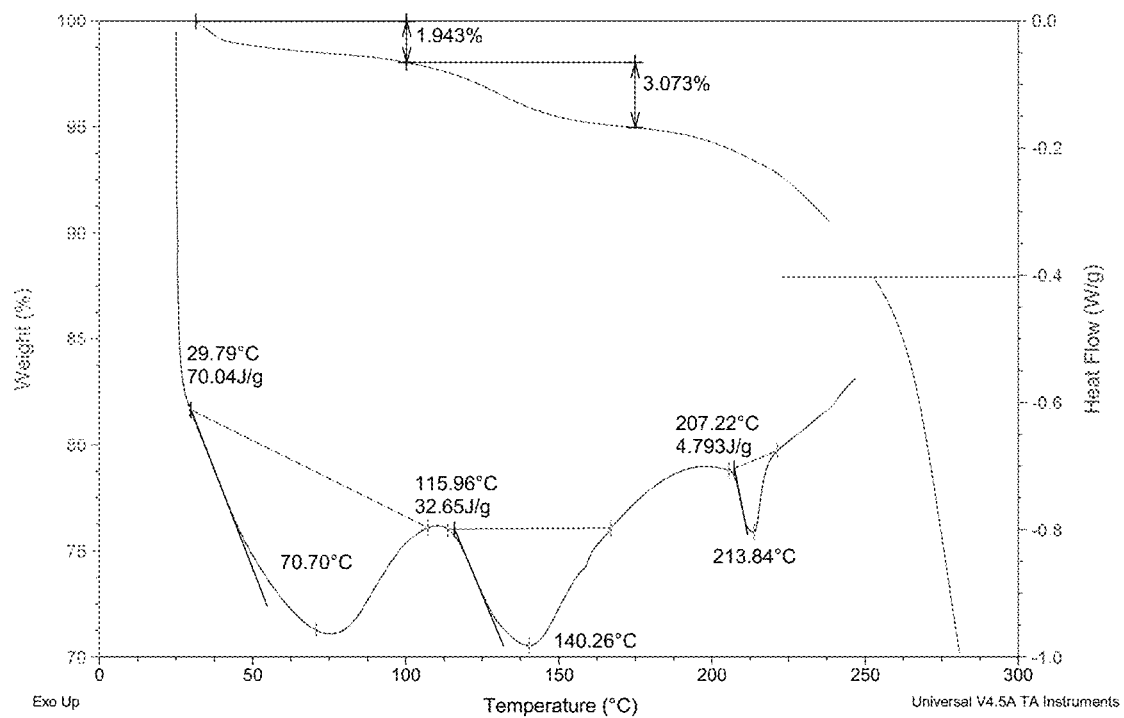
FIG. 25 is a graph showing thermographic data for AM(HS)2. The top line of the graph is a plot of the thermogravimetric analysis (TGA) for the compound, while the bottom line is a plot of the differential scanning calorimetry (DSC).

Further an experiment was performed to show that the crystalline form (I-HS) specifically inhibits the activity of a Trk kinase. For example, the crystalline form (I-HS) did not inhibit the cellular proliferation of a HCC78 cell line derived from a non-small cell lung cancer that expresses the SLC34A2-ROS1 fusion protein (FIG. 23) (Vaishnavi et al., *Nat Med.* 19:1469-72, 2013).

Materials and Methods

Clinical Trial

NCT02122913 is an ongoing multi-center phase 1 dose-escalation study evaluating the safety and pharmacokinetics of the crystalline form (I-HS), a selective pan-TRK, in unselected patients with metastatic or advanced solid tumors without standard therapy options. The study is approved by Institutional Review Boards at all institutions that enroll patients, and eligible patients provide written informed consent to participate. The crystalline form (I-HS) is provided in 100 mg capsules. Enrolled patients receive escalating doses of the crystalline form (I-HS) according to a modified 3+3 design, and receive the crystalline form (I-HS) daily or twice daily until intolerable toxicity, disease progression, or withdrawal of consent. In patients with measurable disease, efficacy is assessed per RECIST 1.1 criteria.

Next Generation Sequencing (NGS)

DNA and RNA were extracted and adaptor ligated sequencing libraries were captured by solution hybridization using custom bait-sets targeting 405 cancer-related genes and 31 frequently rearranged genes by DNA-seq, and 265 frequently rearranged genes by RNA-seq (FoundationOne Heme). All captured libraries were sequenced to high depth (Illumina HiSeq) in a CLIA-certified CAP-accredited laboratory (Foundation Medicine), averaging >500× for DNA and >6M unique pairs for RNA. Sequence data from gDNA and cDNA were mapped to the reference human genome (hg19) and analyzed through a computational analysis pipeline to call genomic alterations present in the sample, including substitutions, short insertions and deletions, rearrangements and copy-number variants.

Fluorescence In Situ Hybridization (FISH)

NTRK1 break-apart FISH was performed on 4 micron slides from formalin-fixed, paraffin embedded (FFPE) tumor samples as previously described using the Vysis LSI NTRK1 (Cen) SpectrumGreen (Cat #08N43-030) and Vysis LSI NTRK1 (Tel) SpectrumRed (Abbott Molecular, #08N43-030 and 08N43-020, respectively) (Vaishnavi et al., *Cancer Discov.* 5:25-34, 2015).

RT-PCR and DNA Sequencing

Reverse trancriptase polymerase chain reaction (RT-PCR) was performed as previously described using the forward primer to LMNA (LMNA F1, 5'gagggcgagctgcatgat'; SEQ ID NO: 1) (Weisner et al., *Nat. Comm.* 5:3116, 2014) and the reverse primer to NTRK1 (NTRK1 Y490rev, 5'cggcgcttgatgtggtgaac'; SEQ ID NO: 2). DNA sequencing of the RT-PCR product was performed using Sanger DNA Sequencing at the Pathology Core at the University of Colorado.

Cell Lines

Informed consent was obtained to derive immortal cell lines from the patient. CUTO-3 cell line and its derivatives were initiated from the malignant pleural effusion of a stage IV lung adenocarcinoma patient harboring the MPRIP-NTRK1 gene fusion as previously described (Vaishnavi et al., *Cancer Discov.* 5:25-34, 2015; Davies et al., *PLoS One* 8:e82236, 2013). KM12 and MO-91 have been previously described (Vaishnavi et al., *Nature Med.* 19:1469-1472, 2013; Taipale et al., *Nat. Biotech.* 31:630-637, 2013).

Patient-Derived Xenograft Generation

Informed consent was obtained from the patient to generate patient-derived murine xenografts. Tumor tissue from an oncogene negative lung adenocarcinoma patient (CULC001) was cut into 3×3×3 mm pieces that were transferred to DMEM supplemented with 10% fetal bovine serum (FBS) and 200 units/mL penicillin, and 200 ug/mL streptomycin. Tumor pieces were dipped in matrigel (Corning) and inserted into incisions on each flank of 5 nude mice. Pleural fluid (CULC002) from a lung adenocarcinoma patient harboring an MRPIP-NTRK1 gene fusion was centrifuged and the resulting cell pellet was suspended in 5 ml ACK buffer (Lonza) for 2 min allowing for the complete lysis of red blood cells. Lysis was halted by the addition of 20 mL PBS and centrifuging the samples. The pellet was washed twice PBS prior to being suspended in DMEM supplemented media as above. 100 μl of cells (1×10$^6$ per flank) suspended in a 1:1 mix of DMEM and matrigel (BD) were injected subcutaneously into the flanks of 5 nude mice. Propagation and maintenance of resulting xenografts was previously described (Keysar et al., *Mol. Oncol.* 7:776-790, 2013).

Proximity Ligation Assays

Cells were seeded onto glass coverslips (in a 48 well plate) or chamber slides at 25-75 k cells/well. Cells were treated with the indicated doses and times then fixed for 15 minutes by shaking at room temperature in 4% paraformaldehyde. The cells were rinsed twice in PBS, and then the Duolink® in situ PLA® kit from SigmaAldrich in mouse/rabbit (Red) was used according to the manufacturer's protocol (catalog # DUO92101). The antibody concentrations were optimized using immunofluorescence prior to PLA experiments. The FFPE tissue PLAs from mice or patients were prepared as described in histology. Additionally, samples were treated with 300 mM glycine for 15 minutes prior to the blocking step, otherwise the assay was performed according to the manufacturer's protocol. The cells were mounted using Prolong® gold anti-fade reagent (with DAPI) and cured overnight prior to imaging. The images were either taken on a Nikon standard inverted fluorescent microscope at 40×, or on the 31 Marianas spinning disc confocal in the University of Colorado Anschutz Medical Campus Advance Light Microscopy Core at 40× or 100×. The following antibodies were used: TRK (C17F1) and ALK (D5F3) from Cell Signaling, SHC1 from Novus, and Grb2 (610111) from BD.

Proliferation Assays

All proliferation assays were performed in media supplemented with 5% FBS as previously described using Cell Titer 96 MTS (Promega) (Bouhana et al., EORTC-NCI-AACR 26$^{th}$ Symposium on Molecular Targets and Cancer Therapeutics, Barcelona, Spain 2014). Cells were seeded 500-2000 cells/well and treated for 72 hours at the drug concentrations described on each graph. Each assay was performed in triplicate in at least 3 independent biological replicates. Data were plotted and IC50 values calculated using GraphPad software.

Immunoblotting

Immunoblotting was performed as previously described (Vaishnavi et al., *Nature Med.* 19:1469-1472, 2013). Briefly, cells were lysed in RIPA buffer with Halt Protease and Phosphatase Inhibitor Cocktail (Thermo Scientific) and diluted in loading buffer (LI-COR Biosciences). The membranes were scanned and analyzed using the Odyssey Imaging System and software (LI-COR). The following antibodies were used from Cell Signaling: pTRK Y490 (rabbit polyclonal, #9141), pERK1/2 XP T202/Y204 (#9101), total ERK1/2, pAKT S473 (rabbit mAb, #4060), and total AKT mouse clone D3A7 (#2920). TRK (C-14) rabbit polyclonal antibody was purchased from Santa Cruz Biotechnology. GAPDH (MAB374) and pTYR (4G10) are from Millipore.

Statistical Analysis

Confidence intervals for the detection rate of NTRK fusions in samples from sarcoma patients were calculated using the 1-sample proportions test. The disease histology classification was based on the Foundation Medicine disease ontology. The enrichment of NTRK fusions in younger patient groups was tested using Fisher's Exact Test. All statistical testing was performed in R v 3.1.3.

Example 9

Clinical Safety and Activity from a Phase 1 Study of Crystalline Form (I-HS), a Selective TRKA/B/C Inhibitor, in Solid-Tumor Patients with NTRK Gene Fusions Methods In this on-going open-label, multicenter, 3+3 dose escalation Phase I study of crystalline form (I-HS), 23 patients with solid tumors refractory to standard therapy, normal hematopoietic and major organ function have been enrolled. Crystalline form (I-HS) was administered orally as a single dose, followed by QD or BID doses for continuous 28-day cycles. Response is measured by RECIST Criteria, version 1.1. Serum is collected for pharmacokinetic analysis on Cycle 1 Day 1 and Day 8. Safety information is collected on all patients and the definition of dose-limiting toxicity applies to adverse events regardless of relationship to investigational product.

Results

To date, 23 patients were treated at each of the first five dose levels ranging from 50 mg QD-150 mg BID. Crystalline form (I-HS) has been well tolerated; the MTD has not been reached and the most common adverse events are Grade 1 and 2 fatigue (35%), dizziness (26%) and anemia (22%). Two patients had dose limiting toxicities (elevated AST, grade 3 (Dose Level 150 mg BID) and delirium, grade 3 unrelated (Dose Level 100 mg BID)).

PK analysis showed maximum plasma concentrations of crystalline form (I-HS) were reached 30-60 minutes following dosing and exposure increased in approximate proportion with dose. The unbound drug levels of crystalline form (I-HS) appear sufficient for approximately 98% inhibition of TRKA/B/C at peak concentrations at all dose levels.

Three of the 23 patients harbored NTRK-fusions and were treated at either 100 or 150 mg BID. These patients achieved a partial response: an undifferentiated sarcoma with an LMNA-NTRK1 fusion (59% decrease; 7 cycles+), a c-kit-negative GI Stromal Tumor (GIST) with an ETV6-NTRK3 fusion (30% decrease; 2 cycles+), and a mammary analogue secretory carcinoma with an ETV6-NTRK3 fusion (64% decrease; 2 cycles+). These data are supported by in vivo tumor growth inhibition and regression in xenograft mouse models of TRK-fusions.

Conclusions

Crystalline form (I-HS) has been well tolerated and has sufficient systemic exposure for robust inhibition of the NTRK-fusions as evidenced by pharmacokinetic drug levels, and the ongoing clinical responses observed in the 3 NTRK-fusion patients enrolled in this study. These data further validate this molecular target as an oncogenic driver across diverse tumor histologies.

Example 10

Comparison of Crystalline Form (I-HS) and the Amorphous Sulfate Salt

Various experiments were performed to compare properties of amorphous (S)—N-(5-((R)-2-(2,5-difluorophenyl)-pyrrolidin-1-yl)-pyrazolo[1,5-a]pyrimidin-3-yl)-3-hydroxy-pyrrolidine-1-carboxamide hydrogen sulfate and crystalline form (I-HS). These studies include impurity profiles, stability, flow properties and hygroscopicity. In the following studies, two lots of amorphous material (AM(HS)1 and AM(HS)2) were compared to a single lot of crystalline form (I-HS). AM(HS)1 and AM(HS)2 were prepared as described in Example 3. Crystalline form (I-HS) was prepared as described in Example 2.

Methods

Residual Solvents

Solutions of AM(HS)1, AM(HS)2, and crystalline form (I-HS) were analyzed using GC-MS headspace analysis.

Thermogravimetric Analysis (TGA)

Samples placed on platinum pans and subjected to 10° C./minute to 300° C.

Differential Scanning Calorimetry (DSC)

Samples were placed in crimped aluminum crucibles with a pin-hole in the lid and subjected to 10° C./minute to 250° C. under nitrogen.

X-Ray Diffraction (XRD)

Cu Kα Radiation at 44 kV, 40 mA through a Ni filter with a divergence slit of ⅔°, Divergence H. L. slit of 10 mm, Scatter slit set to "Auto" (the scatter slit is determined by the computer/instrument), Receiving slit of 0.3 mm. Continuous scan from 3° to 40° 2θ at 2°/min; sampling width (step size) of 0.02°/second, step time of 0.4 point/second. Samples were rotated on a plane parallel to sample surface at 60 rpm.

Polarized Light Microscopy (PLM)

Samples were placed on a glass microscope slide, bathed in low-viscosity oil and covered with a glass coverslip. Examined under 20× objective lens with cross-polarized lenses and a 530 nm cut-off filter. Imaging done with a PAX-It camera and processed by PAX-It software.

Dynamic Vapor Sorption (DVS)

1. The hygroscopicity was studied at 25° C. using an IGAsorp analyzer.
2. About 15 mg of sample was placed in a tared mesh sample holder at an initial ambient room humidity setting of ~35%.
3. A total wet/dry nitrogen flow rate of 250 cc/min is used throughout the study.
4. Solids were studied by performing one full cycle of the following program: 60 minutes of drying at 40° C. under dry $N_2$, followed by settings of 0, 10, 20, 30, 40, 50, 60, 70, 80, 90 and 95% RH, with exposure time at each humidity set point dependent upon 99.5% confidence in the F1 fit model or 60 minutes. The maximum time allowed at any one humidity set point was 120 min. The sample was maintained under dry $N_2$ after the cycle was completed.

Percent weight gain was calculated based on the dry weight basis.

Part One: Physical Characterization of Crystalline Form (I-HS)

AM(HS)1, AM(HS)2, and crystalline form (I-HS) were characterized by appearance, residual solvents, Thermogravimetric Analysis (TGA), Karl Fischer water content (KF), Differential Scanning Calorimetry (DSC), X-Ray Diffraction (XRD), Polarized Light Microscopy (PLM) and hygroscopicity by Dynamic Vapor Sorption (DVS). The data for the physical characterization of the three lots can be found in the Tables 16-19 and FIGS. 24-38.

TABLE 16

Appearance

| Compound | Appearance | Munsell # |
|---|---|---|
| AM(HS)1 | Yellow Powder free of aggregates | 7.5Y 9/10 |
| AM(HS)2 | Yellow Powder free of aggregates | 7.5Y 9/10 |
| Crystalline I-HS | Orange Powder free of aggregates | 2.5YR 7/10 |

TABLE 17

Residual Solvents

| | Solvents (ppm) | | | | | |
|---|---|---|---|---|---|---|
| Compound | Ethanol | Methanol | Methyl t-butyl ether | Heptane | Tetrahydrofuran | Methyl ethyl ketone |
| AM(HS)1 | not detected | 1075 | not tested | not tested | not tested | not tested |
| AM(HS)2 | 174 | 7369 | not tested | not tested | not tested | not tested |
| Crystalline I-HS | 4783 | not tested | not detected | not detected | not detected | 3046 |

TABLE 18

Thermalgravimetric and Karl Fischer (water content) Analyses

| | Thermogravimetric Analysis | | | |
|---|---|---|---|---|
| Compound | Start (° C.) | Stop (° C.) | Change (%) | KF (w/w %) |
| AM(HS)1 | 24.78 | 111.94 | 3.78 | 2.00 |
| | 111.94 | 186.94 | 3.09 | |
| AM(HS)2 | 31.53 | 100.21 | 1.94 | 0.88 |
| | 100.21 | 174.86 | 3.07 | |
| Crystalline I-HS | 23.77 | 218.58 | 6.01 | 0.28 |

TABLE 19

Differential Scanning Calorimetry Analyses

| | Differential Scanning Calorimetry | | | | | |
|---|---|---|---|---|---|---|
| Compound | Type | Start (° C.) | Onset (° C.) | Maximum (° C.) | Stop (° C.) | ΔH (J/g) |
| AM(HS)1 | endotherm | 28.7 | 29.9 | 68.3 | 115.8 | 153.7 |
| | endotherm | 124.1 | 126.1 | 152.8 | 191.0 | 58.3 |
| | endotherm | 204.7 | 205.6 | 211.2 | 220.1 | 7.5 |
| AM(HS)2 | endotherm | 29.6 | 29.8 | 70.7 | 107.2 | 70.0 |
| | endotherm | 113.7 | 116.0 | 140.3 | 167.0 | 32.7 |
| | endotherm | 205.6 | 207.2 | 213.8 | 221.3 | 4.8 |
| Crystalline I-HS | endotherm | 181.9 | 193.7 | 204.6 | 213.8 | 98.9 |

Physical Characterization Conclusion

API forms AM(HS)1 and AM(HS)2 are amorphous with no birefringence by polarized light microscopy and the XRPD pattern is also distinctly amorphous for both lots with no discernible x-ray diffraction peaks. The TGA for the amorphous compounds shows step-wise weight loss corresponding with endothermic events observed in differential scanning calorimetry. The first two endothermic events are quite broad and may indicate an evaporation and/or desolvation. The last endothermic event occurs at the approximate temperature of the melt observed in crystalline material. Both amorphous lots are rather hygroscopic with significant hysteresis upon desorption. AM(HS)1 gained greater than 13% of its original mass at 80% RH. Likewise, AM(HS)2 gained nearly 12% of its starting mass at 80% RH. Post-DVS XRPD indicates that there was no form change during the dynamic vapor sorption however it was observed that the powder deliquesced in the sample holder making removal of the deliquesced powder from the sample holder difficult.

Crystalline form (I-HS) is crystalline in nature with many diffraction peaks by x-ray diffraction and sincere birefringence by polarized light microscopy in its agglomerate-like morphology. Crystalline form (I-HS) shows a thermogravimetric weight loss of 6% corresponding with an endothermic melt onset occurring at 193.7° C. Crystalline form (I-HS) is not hygroscopic, and gained only 1% of its starting mass at 80% RH.

Part Two: Powder Properties of Crystalline Form (I-HS)

The following studies compared the crystalline hydrogen sulfate salt with the amorphous sulfate salt powder including a study of each form's flow properties which are important for manufacturing a solid oral dosage form such as a tablet or capsule. Work performed includes bulk density, tapped density, angle of repose, and compression profiles.

Blends

Blends were created according to the formulations presented in Tables 20 and 21. These blends are typical of tablet formulations that could be manufactured as a direct compression or roller compaction based tablet or formulated capsule. First API (i.e. either AM(HS) or crystalline form (I-HS)), microcrystalline cellulose (MCC), and either starch or lactose were added to a 30 cc amber glass bottle and blended on the TURBULA® Shaker-mixer at 25 rpm for 3 minutes. Then the remaining excipients were added to the bottle and blended on the TURBULA® at 25 rpm for an additional 3 minutes.

TABLE 20

Tablet Formulation with 2:1 MCC:Lactose, 50% Drug Load

| Component | Grade | Purpose | Percentage | Target Mass(g) | Crystalline Actual Mass(g) | Amorphous Actual Mass(g) |
|---|---|---|---|---|---|---|
| API | NA | Drug Substance | 50.00 | 2.500 | 2.5004 | 2.5009 |
| MCC | PH102 NF | diluent | 30.30 | 1.515 | 1.5152 | 1.5153 |
| Lactose | Fast-Flo 316 | diluent | 15.20 | 0.760 | 0.7603 | 0.7602 |
| Croscarmellose Sodium | Ac-Di-Sol | disintegrant | 3.00 | 0.150 | 0.1503 | 0.1498 |
| Silicon Dioxide | Cabosil | glidant | 1.00 | 0.050 | 0.0502 | 0.0497 |
| Mg. Stearate | USP-NF | lubricant | 0.50 | 0.025 | 0.0248 | 0.0254 |
| | | Total | 100.00 | 5.000 | 5.0012 | 5.0013 |

TABLE 21

Tablet Formulation with 1:1 MCC:Starch, 50% Drug Load

| Component | Grade | Purpose | Percentage | Target Mass(g) | Crystalline Actual Mass(g) | Amorphous Actual Mass(g) |
|---|---|---|---|---|---|---|
| API | N/A | Drug Substance | 50.00 | 2.500 | 2.4994 | 2.4998 |
| MCC | PH102 NF | diluent | 22.75 | 1.138 | 1.1385 | 1.1387 |
| Pre-gelatinized starch | StarCap 1500 | diluent | 22.75 | 1.138 | 1.1385 | 1.1376 |
| Croscarmellose Sodium | Ac-Di-Sol | disintegrant | 3.00 | 0.150 | 0.1507 | 0.1503 |
| Silicon Dioxide | Cabosil | glidant | 1.00 | 0.050 | 0.0500 | 0.0498 |
| Mg. Stearate | USP-NF | lubricant | 0.50 | 0.025 | 0.0252 | 0.0250 |
| | | Total | 100.00 | 5.000 | 5.0023 | 5.0012 |

Angle of Repose

The angle of repose is the angle formed by the horizontal base of the surface and the edge of a cone-like pile of granules. It is calculated from the following equation:

$$\theta = \tan^{-1}\left(\frac{h}{r}\right)$$

The angle of repose was measured by slowly pouring approximately 1 g of sample through a funnel with a 3/16" inner diameter of the outlet. The powder then fell 1 11/16" to land on the surface of an overturned crystallization dish on which a pile of powder formed. A picture was taken of the pile after addition of all of the material. The angle between the dish surface and the surface of the pile was measure via a protractor on the pictures. Care was taken to replicate the same positions and fall distances in the set up between different samples.

Bulk and Tap Densities

The powder was added to a pre-weighed 10 mL graduated cylinder through a funnel that was not in direct contact with the graduated cylinder to avoid transference of vibrations. Powder was added until a 10 mL volume was reached and then the graduated cylinder with powder was weighed. The bulk density was calculated by $$\text{Bulk Density} = \frac{(\text{Mass of cylinder} + \text{powder}) - \text{Mass of empty cylinder}}{10 \text{ mL}}.$$

The same sample in the graduated cylinder was tapped for the following sequence: 100, 150, 250, 250 taps. The volume was measured after each interval. The tapped density was calculated by $$\text{Tapped Density} = \frac{(\text{Mass of cylinder} + \text{powder}) - \text{Mass of empty cylinder}}{\text{Volume after 750 total taps}}.$$

The Carr's Index was calculated according to the following equation:

$$CI = \frac{\rho_{tap} - \rho_{bulk}}{\rho_{tap}} \times 100$$

The Hausner Ratio was calculated with the following equation:

$$HR = \frac{\rho_{tap}}{\rho_{bulk}}$$

Compression Profiles

Figure 39:
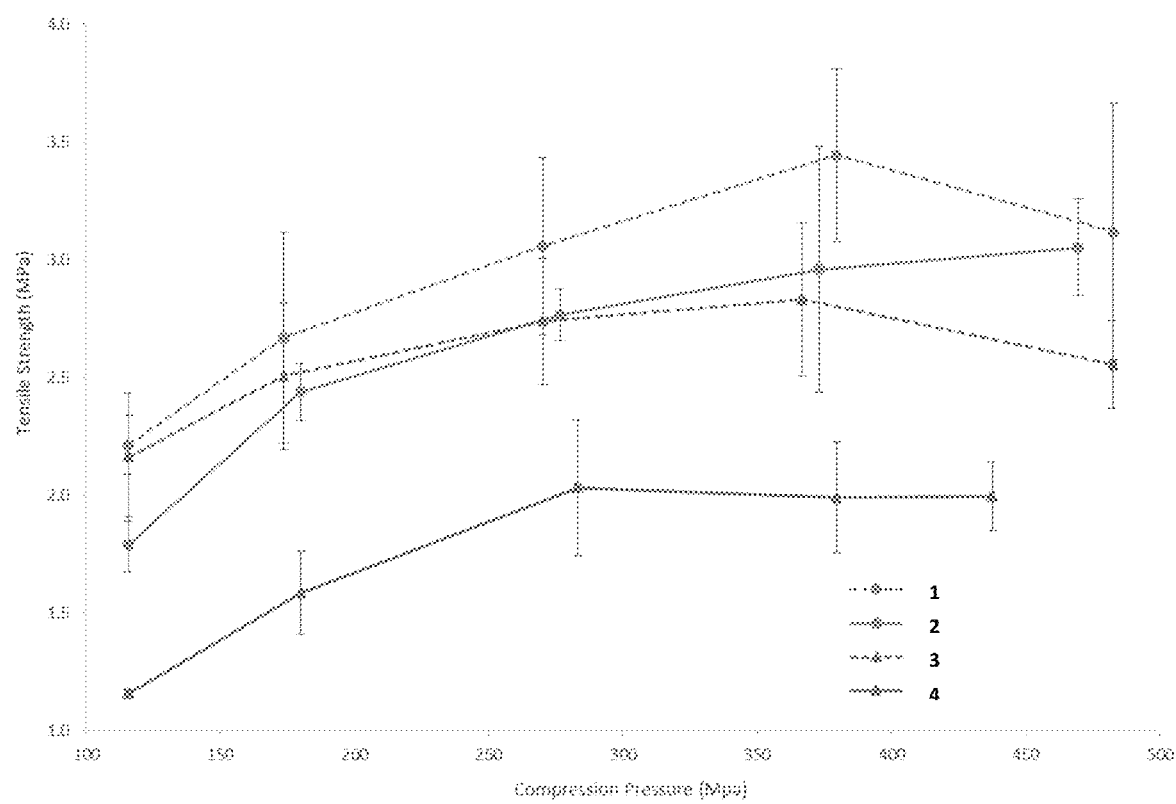
FIG. 39 is a plot of tensile strength versus compression pressure for various 200 mg direct compression blend compacts incorporating crystalline form (I-HS) or AM(HS)2. In the plot, (1) is a 2:1 MCC:lactose blend with AM(HS)2; (2) is a 2:1 MCC:lactose blend with crystalline form (I-HS); (3) is a 1:1 MCC:starch blend with AM(HS)2; (4) is a 1:1 MCC:starch blend with crystalline form (I-HS).
Figure 40:
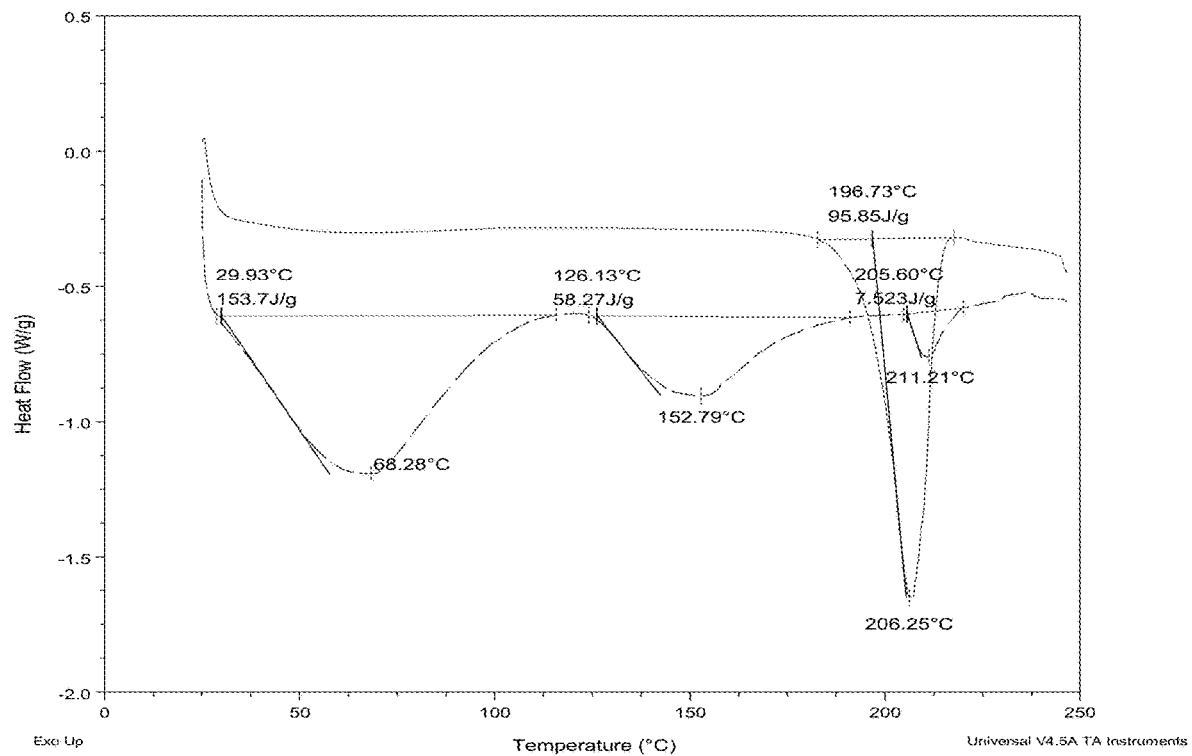
FIG. 40 is an overlay of DSC thermographs of AM(HS)1 at T0 (bottom line) and after 5 weeks at 40° C./75% RH (top line).
Figure 41:
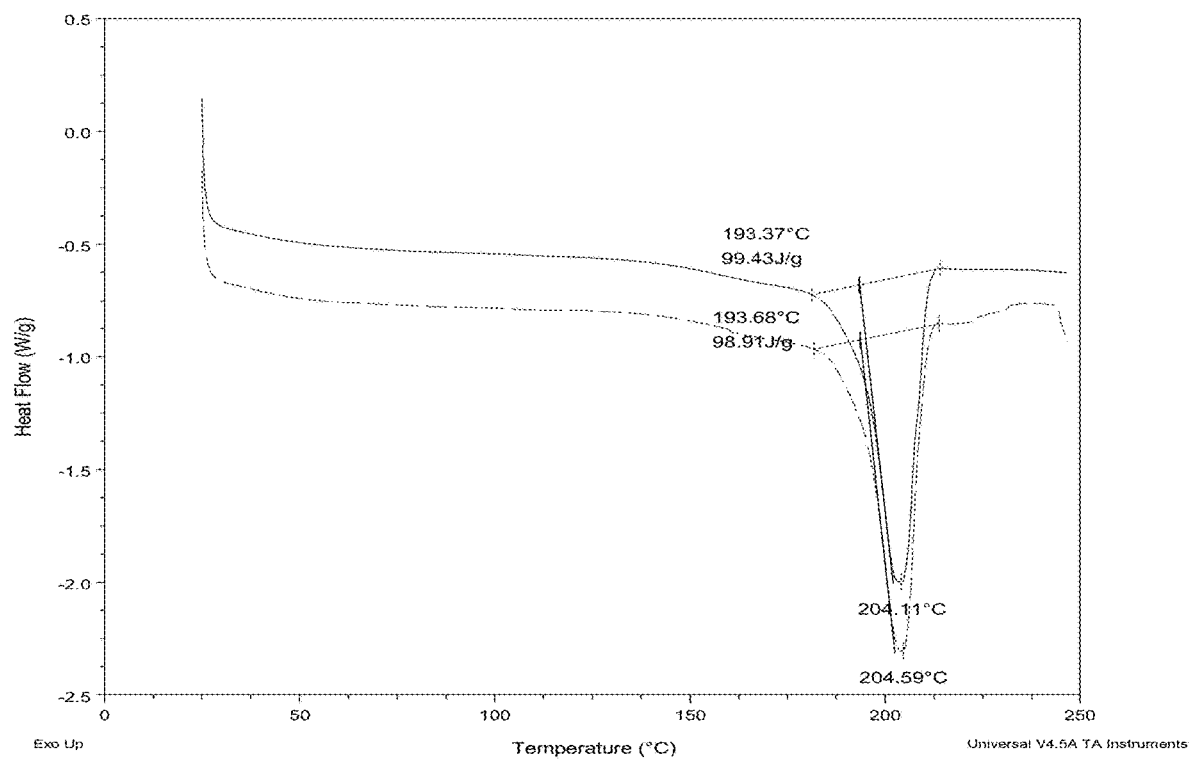
FIG. 41 is an overlay of DSC thermographs of crystalline form (I-HS) at T0 (bottom line) and after 5 weeks at 40° C./75% RH (top line).
Figure 42:
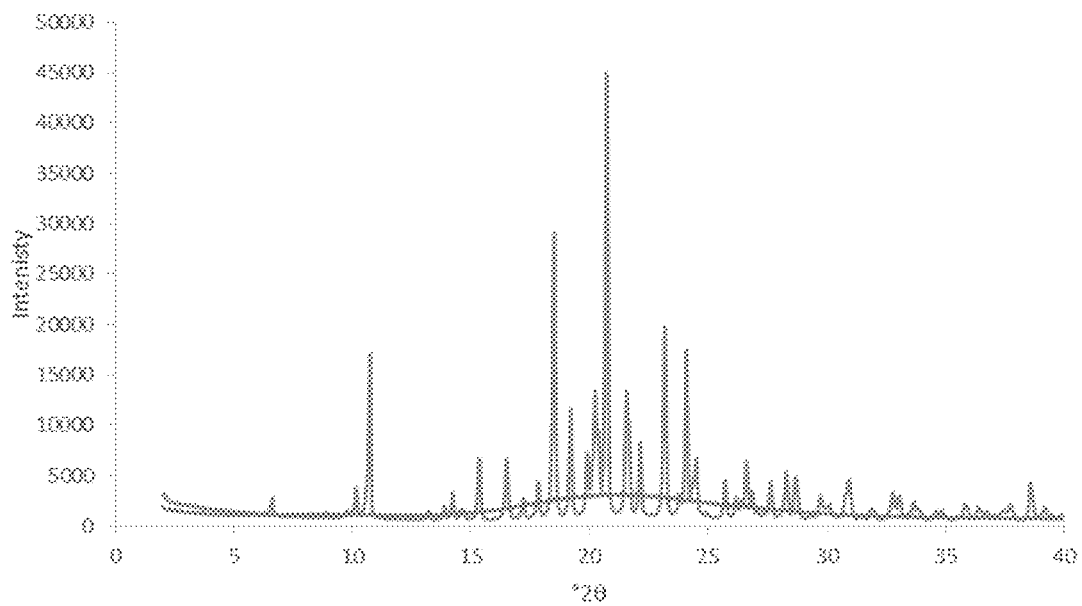
FIG. 42 illustrates an overlay of the X-ray powder diffraction (XRPD) patterns of AM(HS)1 at T0 (broad line) and after 5 weeks at 40° C./75% RH (sharp peaks).
Figure 43:
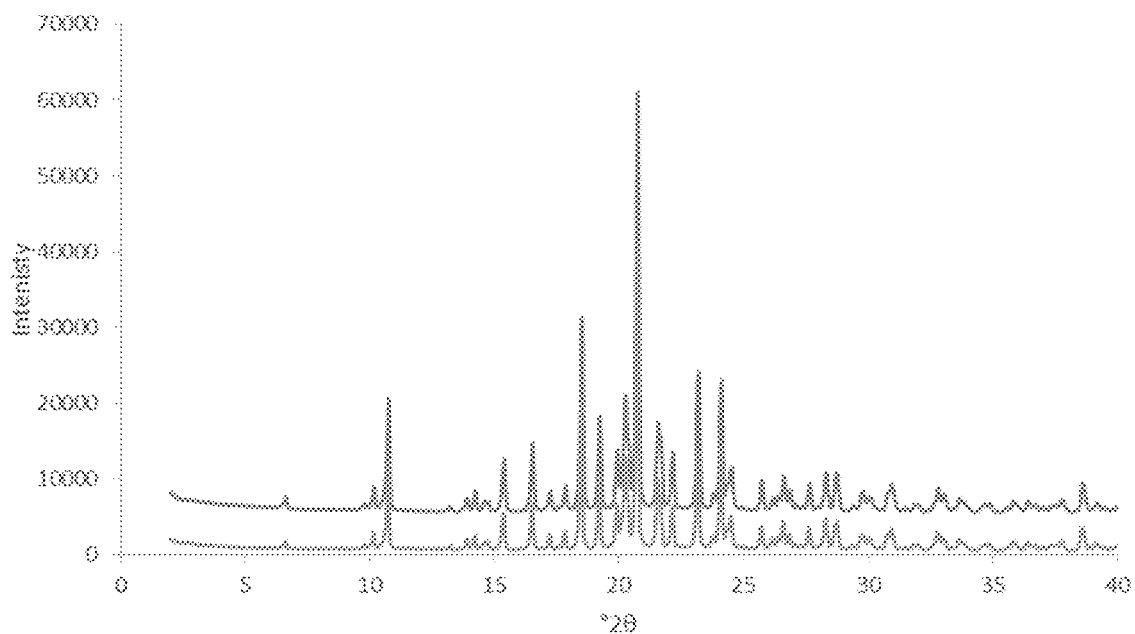
FIG. 43 illustrates an overlay of the X-ray powder diffraction (XRPD) patterns of crystalline form (I-HS) at T0 (bottom) and after 5 weeks at 40° C./75% RH (top).
Figure 44:
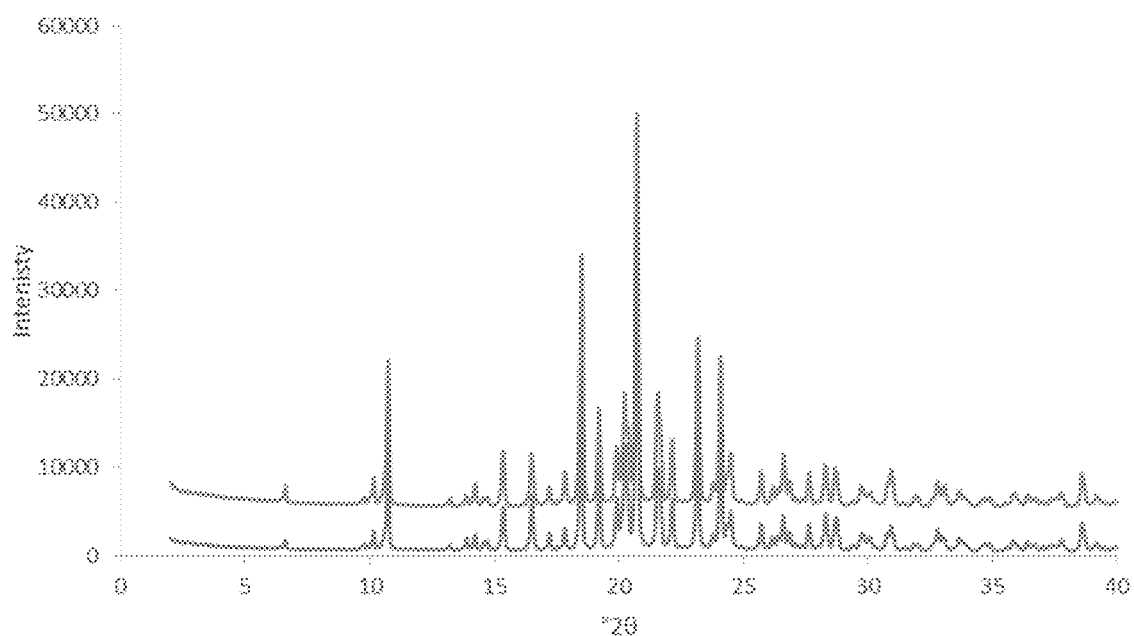
FIG. 44 illustrates an overlay of the X-ray powder diffraction (XRPD) patterns of crystalline form (I-HS) (bottom) and AM(HS)1 (top) after 5 weeks at 40° C./75% RH.

Compression profiles were generated by creating 5/16" diameter, round tablets at five different compression pressures for each blend. The press settings were 1 second dwell time and 15% pump speed. Tablets were created for all four powder blends using compression forces of 700 kg, 1000 kg, 1500 kg, and 2000 kg. The highest compression force was selected based on the results of the previous tablets. Tablet mass, dimensions, and rupture force were then measured. These data were plotted using a template resulting in a plot of compression pressure vs. tensile strength (FIG. 39).

Results

TABLE 22

| Flow Character | Angle of Repose | Hausner Ratio | Compressibility Index (%) |
|---|---|---|---|
| Excellent | 25-30° | 1.00-1.11 | ≤10 |
| Good | 31-35° | 1.12-1.18 | 11-15 |
| Fair | 36-40° | 1.19-1.25 | 16-20 |
| Passable | 41-45° | 1.26-1.34 | 21-25 |
| Poor | 46-55° | 1.35-1.45 | 26-31 |
| Very Poor | 56-65° | 1.46-1.59 | 32-27 |
| Very, Very Poor | ≥66° | ≥1.60 | ≥38 |

Results are presented in Tables 23 and 24 and FIG. 39. According to the U.S. Pharmacopeial Convention (USP), all samples fall into the passable or poor category for flow as measured by angle of repose. Larger angles indicate worse flow. The Carr's Index (Compressibility Index) and Hausner Ratio fall between passable and very poor according to USP. The crystalline API is noticeably different from the amorphous API and these differences are present in all formulation blends irrespective of the content of amorphous or crystalline API. For the crystalline API, the Hausner Ratio and the Carr's Index indicate flow properties are "Passable". The amorphous API has considerably worse flow properties, being categorized as "Very Poor" for both the Hausner ration and Carr's Index. See Table 22 for the relevant USP tables.

When creating tablets for the compression profiles, the crystalline API blends produced multiple tablets that had breakage upon ejection from the tooling. The amorphous API blends seemed to produce visually better tablets, i.e. little to no breakage.

TABLE 23

Angle of Repose

| Sample | θ(°) | φ(°) | Average(°) |
|---|---|---|---|
| L-ARR10-118 | 50.28 | 50.28 | 50.28 |
| AR00457470-33 | 47.79 | 43.6 | 45.70 |
| 2:1 MCC:Lactose L-ARR10-118 | 45.21 | 41.81 | 43.51 |
| 2:1 MCC:Lactose AR00457470-33 | 41.01 | 42.64 | 41.83 |
| 1:1 MCC:Starch L-ARR10-118 | 39.52 | 41.01 | 40.27 |
| 1:1 MCC:Starch AR00457470-33 | 40.44 | 48.59 | 44.52 |

*θ and φ are the angles on either side of the pyramid (2D).

TABLE 24

Bulk and Tap Densities

| Sample | Bulk Density (mg/mL) | Tapped Density (mg/mL) | Carr Index | Hausner Ratio |
|---|---|---|---|---|
| L-ARR10-118 | 594.8 | 762.6 | 22% | 1.28 |
| AR00457470-33 | 423.6 | 622.9 | 32% | 1.47 |
| 2:1 MCC:Lactose L-ARR10-118 | 435.3 | 621.9 | 30% | 1.43 |
| 2:1 MCC:Lactose AR00457470-33 | 408.1 | 583.0 | 30% | 1.43 |
| 1:1 MCC:Starch L-ARR10-118 | 437.9 | 625.5 | 30% | 1.43 |
| 1:1 MCC:Starch AR00457470-33 | 411.4 | 605.0 | 32% | 1.47 |

Powder Properties Conclusion

By the angle of repose the crystalline form (I-HS) formulation blends, amorphous API and amorphous API formulation blends tested have "Very Poor" flow characteristics. However, by Carr's Index and Hausner Ratio the crystalline API, crystalline form (I-HS), has "passable" flow characteristics. The significantly better flow properties here are an advantage for solid oral dosage form development and manufacturing. There was also not a large difference in the compression profile of both blends with both lots of powder. This is an indication that (5)-N-(5-((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate whether amorphous or crystalline did not positively nor negatively affect the flow of the blends at a 50% drug load.

Part Three: Stability of AM(HS)1 and Crystalline Form (I-HS)

Aliquots of powder of AM(HS)1 and crystalline form (I-HS) were placed into non-capped (open) 20 mL scintillation vials and the vials placed into an LDPE bag put into a stability chamber maintained at 40° C./75% RH for five weeks. Upon removal from the chamber, the samples were physically characterized by appearance, KF, TGA, DSC, XRD and PLM. The samples were also analyzed by HPLC for chromatographic purity, chiral integrity and potency. Where applicable, the data presented in the stability portion also includes the original T=0 data for comparison purposes. The data can be seen in Tables 25-29 and FIGS. 40-44.

TABLE 25

Appearance of Stability Samples

| Compound | Condition | Time point (wks.) | Appearance | Munsell # |
|---|---|---|---|---|
| AM(HS)1 | NA | 0 | Yellow Powder free of aggregates | 7.5Y 9/10 |
| AM(HS)1 | 40° C./75% RH | 5 | Orange Powder some aggregates | 2.5YR 7/10 |
| Crystalline form (I-HS) | NA | 0 | Orange Powder free of aggregates | 2.5YR 7/10 |
| Crystalline form (I-HS) | 40° C./75% RH | 5 | Orange Powder free of aggregates | 2.5YR 7/10 |

TABLE 26

TGA and KF of Stability Samples

| Compound | Condition | Time point (wks.) | Start (° C.) | Stop (° C.) | Change (%) | KF (w/w %) |
|---|---|---|---|---|---|---|
| AM(HS)1 | NA | 0 | 24.78 111.94 | 111.94 186.94 | 3.78 3.09 | 2.00 |
| AM(HS)1 | 40° C./75% RH | 5 | 36.27 | 217.16 | 5.32 | 0.56 |
| Crystalline form (I-HS) | NA | 0 | 23.77 | 218.58 | 6.01 | 0.28 |
| Crystalline form (I-HS) | 40° C./75% RH | 5 | 36.66 | 217.87 | 6.00 | 0.21 |

TABLE 27

DSC of Stability Samples

| Cmpd | Condition | Time point (wks.) | Type | Start (° C.) | Onset (° C.) | Maximum (° C.) | Stop (° C.) | ΔH (J/g) |
|---|---|---|---|---|---|---|---|---|
| AM(HS)1 | NA | 0 | endotherm | 28.7 | 29.9 | 68.3 | 115.8 | 153.7 |
|  |  |  | endotherm | 124.1 | 126.1 | 152.8 | 191.0 | 58.3 |
|  |  |  | endotherm | 204.7 | 205.6 | 211.2 | 220.1 | 7.5 |
| AM(HS)1 | 40° C./75% | 5 | endotherm | 182.7 | 196.7 | 206.3 | 217.7 | 95.9 |
| Crystalline form (I-HS) | NA | 0 | endotherm | 181.9 | 193.7 | 204.6 | 213.8 | 98.9 |
| Crystalline form (I-HS) | 40° C./75% RH | 5 | endotherm | 181.3 | 193.4 | 204.1 | 214.1 | 99.4 |

TABLE 28

HPLC Data of Stability Samples

| Compound | Condition | Time point (wks.) | Total Impurities (%) | Assay (%) | Chiral Potency (%) |
|---|---|---|---|---|---|
| AM(HS)1 | NA | 0 | 1.10 | 79.5 | 99.6 |
| AM(HS)1 | 40° C./75% RH | 5 | 1.16 | 80.3 | 99.6 |
| Crystalline form (I-HS) | NA | 0 | 0.14 | 79.4 | 99.6 |
| Crystalline form (I-HS) | 40° C./75% RH | 5 | 0.07 | 79.6 | 99.6 |

TABLE 29

HPLC Data: Peak Area Percent by RRT of Stability Samples

| Sample | Condition | Time point (wks.) | RRT 0.793 | RRT 0.863 | RRT 0.981 | RRT 1.000 | RRT 1.535 |
|---|---|---|---|---|---|---|---|
| AM(HS)1 | NA | 0 | 0.00 | 0.98 | 0.12 | 98.89 | 0.00 |
|  | 40° C./75% RH | 5 | 0.00 | 1.04 | 0.12 | 98.83 | 0.00 |
| Crystalline form (I-HS) | NA | 0 | 0.07 | 0.00 | 0.00 | 99.86 | 0.07 |
| (I-HS) | 40° C./75% RH | 5 | 0.07 | 0.00 | 0.00 | 99.93 | 0.00 |

Stability Conclusions

Amorphous compound AM(HS)1 was not stable in humidified conditions and tended to crystallize over a period of time. This was evidenced by the deliquescence of samples left in humidity chambers and the changed appearance both by the eye and polarized light microscopy (data not shown). The amorphous material goes from a free flowing yellow powder to an orange agglomerated non-free flowing powder. The polarized light microscopy, XRPD, DSC, TGA and KF of the amorphous API also changed significantly over the course of the accelerated stability study to become the same polymorphic form as the crystalline form (I-HS). The XRPD pattern of the amorphous compound AM(HS)1 transforms into the XRPD pattern of crystalline form (I-HS) over the course of the accelerated stability study. The polarized light microscopy goes from non-birefringent to birefringent under cross-polarized light which is indicative of a change from amorphous to crystalline API. The DSC at t=0 has two endothermic events with melt maximums at 68.3° C. and 152.8° C. that disappear at the t=5 week time point. There is only a single endothermic event remaining for the amorphous material with a melt maximum at 206° C. This melt maximum matches the thermographic profile of the crystalline API. The TGA profile of the amorphous material at t=5 weeks also changed to match the profile and weight loss of the crystalline API. Crystalline form (I-HS) exhibited no hygroscopicity nor any change in color, morphology or crystallinity after storage under accelerated conditions.

The API chemical purity did not change significantly over the course of the stability study for either the AM(HS)1 or crystalline form (I-HS). The impurity profiles of the amorphous and crystalline form (I-HS) are, however, significantly different. The amorphous material contains significantly higher levels of impurities (Tables 22 and 23) versus the crystalline form (I-HS). The reduced impurities in the crystalline form (I-HS) vs. the amorphous AM(HS)1 at relative retention times (RRT) 0.863 (0.00% vs. 0.98%) and 1.535 (0.00% vs. 0.12%) is believed to be due to the isolation of crystalline form (I-HS) via a crystallization process that rejects these impurities and is superior to the method of isolation for the amorphous AM(HS)1. The amorphous AM(HS)1 isolation process does not appear to reject these impurities as efficiently.

Overall Summary of Study
1. The crystalline form (I-HS) has better flow properties vs. the amorphous form AM(HS). The differences in flow properties will improve development of a solid oral dosage form crystalline form (I-HS) vs. the AM(HS).
2. The stability study in an LDPE bag at 40° C./75% RH for five weeks did not show significant changes in chemical impurity levels for either forms of the compound. It did, however, reveal that crystalline form (I-HS) did not have a significant change in its physicochemical properties over the course of the study. In contrast, AM(HS), converted into a crystalline form substantially similar to crystalline form (I-HS) by XRPD, DSC, TGA, KF and polarized light microscopy. Additionally, AM(HS) changed to an agglomerated powder with reduced flow properties over the course of the stability testing. A change in the amorphous AM(HS) properties to a crystalline material and/or an agglomerated powder with reduced flow ability on storage of AM(HS) would make it impossible to manufacture a solid oral dosage form for patient use based on the amorphous compound.

3. AM(HS) deliquesced when exposed to humidity. This would require significant handling precautions during storage and manufacture to prevent this occurrence whereas crystalline form (I-HS) requires no such precautions during manufacture of crystalline form (I-HS) and any solid oral dosage product prepared using crystalline form (I-HS).

4. Crystalline form (I-HS) provides a significantly improved impurity profile as compared to AM(HS). The ability to control an impurity profile is important for patient safety and required by Regulatory agencies.

Example 11

Figure 45:
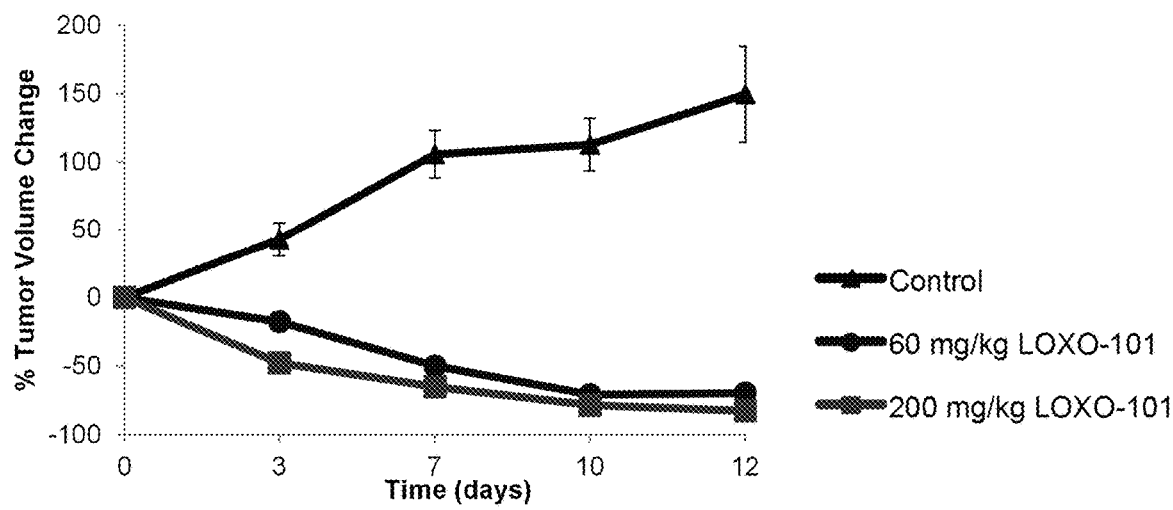
FIG. 45 is a graph showing the percentage of change in volume of a xenograph (human) tumor derived from a lung adenocarcinoma CUTO-3F cell line (CUTO-3.29) over time in mice that were treated with vehicle (triangles) or orally administered a daily dose of 60 mg/kg (circles) or 200 mg/kg (squares) of crystalline form (I-HS) following implantation of the xenograft into the mice.
Figure 46:
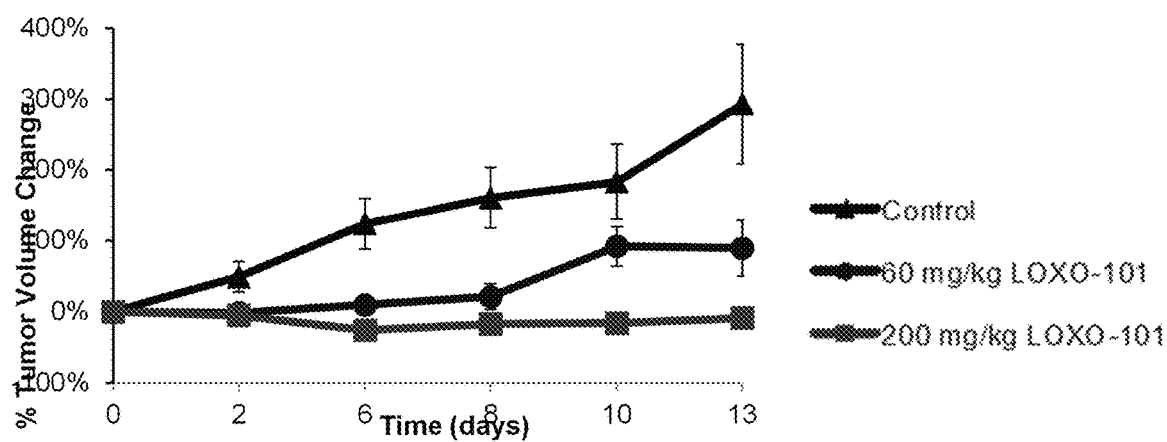
FIG. 46 is a graph showing the percentage of change in volume of a xenograph (human) tumor derived from a colorectal cancer KM12 cell line over time in mice that were treated with vehicle (triangles) or orally administered a daily dose of 60 mg/kg (circles) or 200 mg/kg (squares) of crystalline form (I-HS) following implantation of the xenograft into the mice.
Figure 47:
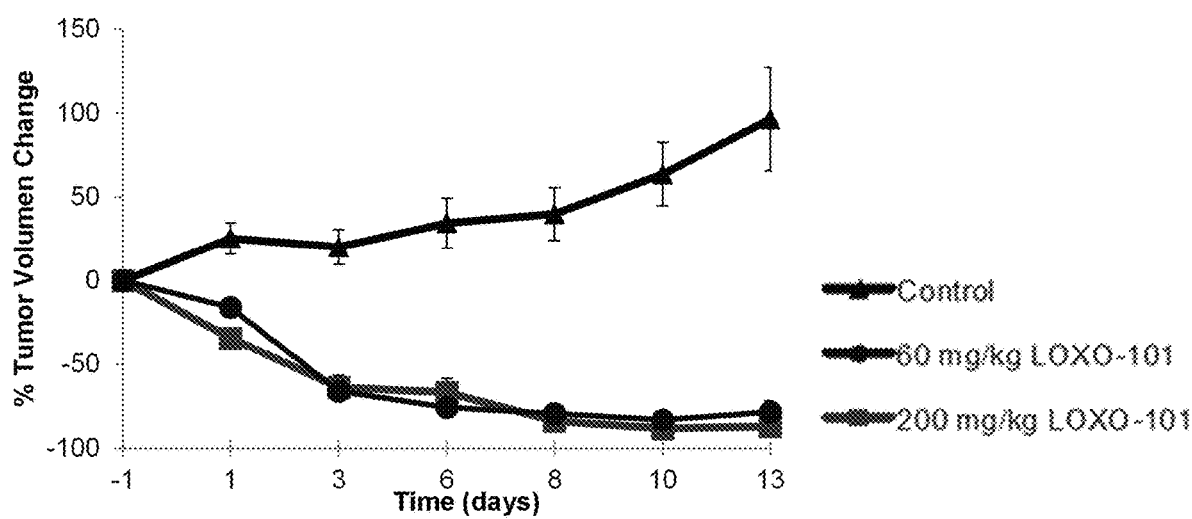
FIG. 47 is a graph showing the percentage of change in volume of a xenograph (human) tumor derived from an acute myeloid leukemia MO-91 cell line over time in mice that were treated with vehicle (triangles) or orally administered a daily dose of 60 mg/kg (circles) or 200 mg/kg (squares) of crystalline form (I-HS) following implantation of the xenograft into the mice.

The Crystalline Form (I-HS) Decreases the Growth of Tumors Characterized as Expressing a Trk Fusion Protein A set of experiments were performed to determine whether the crystalline form (I-HS) would inhibit the growth of three different xenograph (human) tumors in mice, with each xenograph tumor being derived from a cancer cell line. The three different cancer cell lines, the CUTO-3F cell line, the KM12 cell line, and the MO-91 cell line, each express a different Trk gene fusion. As described in Example 7, the CUTO-3F cell line is derived from a patient with lung adenocarcinoma harboring the MPRIP-NTRK1 gene fusion, the KM12 cell line is a colorectal cancer cell line harboring the TPM3-NTRK1 fusion (Vaishnavi et al., *Nature Med.* 19:1469-1472, 2013), and the MO-91 cell line is derived from an acute myeloid leukemia patient harboring the ETV6-NTRK3 fusion (Taipale et al., *Nature Biotech.* 31:630-637, 2013). Following implantation of one of these three different xenograph (human) tumors in mice, the change in the volume of each tumor was monitored. The resulting mice were left treated with vehicle or were orally administered a daily dose of 60 mg/kg or 200 mg/kg of crystalline form (I-HS) (FIGS. 45-47, respectively) following implantation of the xenograft.

These data show that administration of the crystalline form (I-HS) is able to effectively halt the growth, or decrease the rate of growth, of human tumors characterized by expression of an oncogenic Trk fusion protein in a mammal.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

REFERENCES

1. Wiesner et al., *Nature Comm.* 5:3116, 2014.
2. Vaishnavi et al., *Nature Med.* 19:1469-1472, 2013.
3. Greco et al., *Mol. Cell. Endocrinol.* 28:321, 2010.
4. Kim et al., *PloS ONE* 9(3):e91940, 2014.
5. Vaishnavi et al., *Nature Med.* 19:1469-1472, 2013.
6. Fernandez-Cuesta et al., "Cross-entity mutation analysis of lung neuroendocrine tumors sheds light into their molecular origin and identifies new therapeutic targets," AACR Annual Meeting 2014, Abstract, April 2014.
7. Stransky et al., *Nature Comm.* 5:4846, 2014.
8. Ross et al., *Oncologist* 19:235-242, 2014.
9. Doebele et al., *J. Clin. Oncol.* 32:5s, 2014.
10. Jones et al., *Nature Genetics* 45:927-932, 2013.
11. Wu et al., *Nature Genetics* 46:444-450, 2014.
12. WO 2013/059740
13. Zheng et al., "Anchored multiplex PCR for targeted next-generation sequencing," *Nature Med.*, published online on Nov. 10, 2014.
14. Caria et al., *Cancer Genet. Cytogenet.* 203:21-29, 2010.
15. Frattini et al., *Nature Genet.* 45:1141-1149, 2013.
16. Martin-Zanca et al., *Nature* 319:743, 1986.
17. Meyer et al., *Leukemia* 21: 2171-2180, 2007.
18. Reuther et al., *Mol. Cell. Biol.* 20:8655-8666, 2000.
19. Marchetti et al., *Human Mutation* 29(5):609-616, 2008.
20. Tacconelli et al., *Cancer Cell* 6:347, 2004.
21. Walch et al., *Clin. Exp. Metastasis* 17: 307-314, 1999.
22. Papatsoris et al., *Expert Opin. Invest. Drugs* 16(3):303-309, 2007.
23. Van Noesel et al., *Gene* 325: 1-15, 2004.
24. Zhang et al., *Oncology Reports* 14: 161-171, 2005.
25. Truzzi et al., *J. Invest. Dermatol.* 128(8):2031, 2008.
26. Kolokythas et al., *J. Oral Maxillofacial Surgery* 68(6): 1290-1295, 2010.
27. Ni et al., *Asian Pacific Journal of Cancer Prevention* 13:1511, 2012.

What is claimed:

1. A crystalline form (I-HS) having the formula:

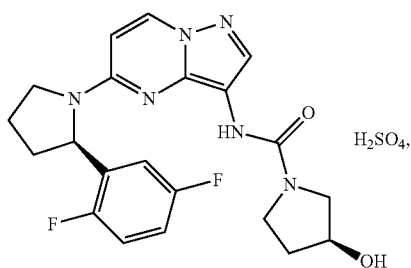

I-HS wherein the crystalline form is substantially free of the amorphous form.

2. The crystalline form according to claim 1, characterized by having XRPD diffraction peaks (2θ degrees) at 18.4±0.2, 20.7±0.2, 23.1±0.2, and 24.0±0.2.

3. The crystalline form according to claim 1, characterized by having XRPD diffraction peaks (2θ degrees) at 10.7±0.2, 18.4±0.2, 20.7±0.2, 23.1±0.2, and 24.0±0.2.

4. The crystalline form according to claim 1, characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2.

5. The crystalline form according to claim 1, characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2, 24.4±0.2, 25.6±0.2, 26.5±0.2, 27.6±0.2, 28.2±0.2, 28.7±0.2, 30.8±0.2, and 38.5±0.2.

6. The crystalline form according to claim 1, wherein the crystalline form has XRPD pattern substantially as shown in FIG. 29.

7. The crystalline form according to claim 1, wherein the crystalline form exhibits an onset to maximum of about 193 to about 205° Celsius, as measured by differential scanning calorimetry.

8. The crystalline form according to claim 1, wherein the crystalline form exhibits a heat of melting of about 2.415 mW, as measured by differential scanning calorimetry.

Figure 26:
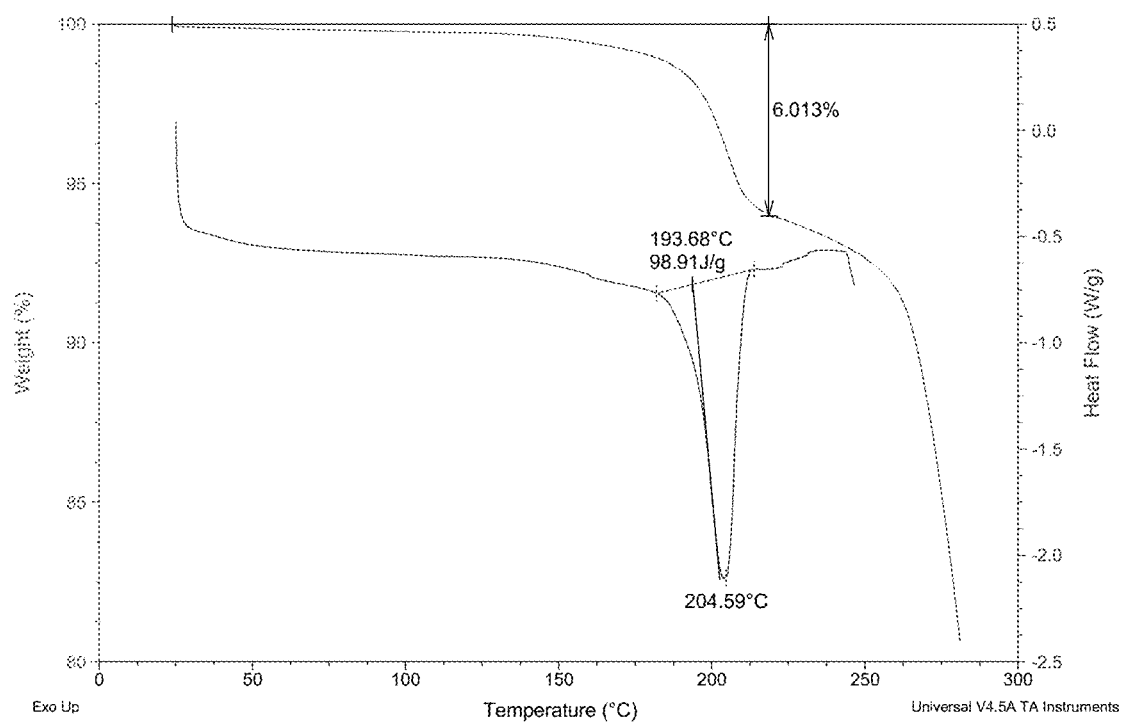
FIG. 26 is a graph showing thermographic data for crystalline form (I-HS). The top line of the graph is a plot of the thermogravimetric analysis (TGA) for the compound, while the bottom line is a plot of the differential scanning calorimetry (DSC).
Figure 27:
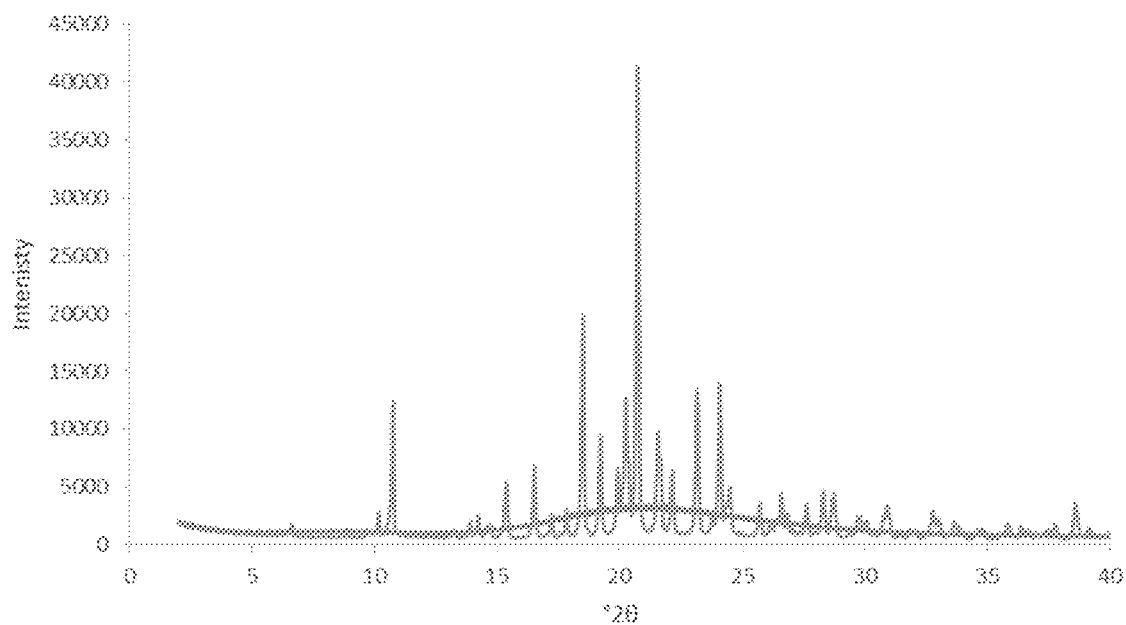
FIG. 27 illustrates an overlay of the X-ray powder diffraction (XRPD) patterns of AM(HS)1, AM(HS)2, and crystalline form (I-HS). AM(HS)1 and AM(HS)2 are the broad lines in the lower part of the figure, while crystalline form (I-HS) exhibits sharp peaks.

9. The crystalline form according to claim 1, wherein the crystalline form has a DSC thermogram substantially as shown in FIG. 26.

10. The crystalline form according to claim 1, wherein the crystalline form is non-hygroscopic.

11. A pharmaceutical composition comprising a pharmaceutically acceptable carrier and a crystalline form according to claim 1.

12. A pharmaceutical composition made by mixing a crystalline form according to claim 1 and a pharmaceutically acceptable carrier.

13. The crystalline form (I-HS) according to claim 1, prepared by a process comprising:
(a) mixing (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate having an ethanol impurity with a 5:95 w/w solution of water/2-butanone;
(b) heating the mixture from step (d) at about 65-70° C. with stirring until the weight percent of ethanol is about 0.5% to form a slurry of the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate; and
(c) isolating the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate, substantially free of the amorphous form, by filtration.

14. The crystalline form (I-HS) according to claim 13, wherein the (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate having an ethanol impurity is prepared by
(a) adding concentrated sulfuric acid to a solution of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide in ethanol to form the hydrogen sulfate salt of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide;
(b) adding heptane to the solution in Step (a) to form a slurry; and
(c) filtering the slurry to isolate (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate.

15. The crystalline form according to claim 14, made by a process further comprising:
(b1) seeding the solution from step (a) with (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate at room temperature and allowing the solution to stir until a slurry forms.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1
gagggcgagc tgcatgat                                                   18

<210> SEQ ID NO 2
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 2
cggcgcttga tgtggtgaac                                           20
```